United States Patent
Tso et al.

(10) Patent No.: US 9,951,120 B2
(45) Date of Patent: *Apr. 24, 2018

(54) METHOD OF TREATING DIABETES USING NON-GLYCOSYLATED APOLIPOPROTEIN A-IV

(71) Applicant: University of Cincinnati, Cincinnati, OH (US)

(72) Inventors: Patrick Tso, Cincinnati, OH (US); Fei Wang, Cincinnati, OH (US); Sean Davidson, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/373,259

(22) PCT Filed: Nov. 21, 2012

(86) PCT No.: PCT/US2012/066314
§ 371 (c)(1),
(2) Date: Jul. 18, 2014

(87) PCT Pub. No.: WO2013/109342
PCT Pub. Date: Jul. 25, 2013

(65) Prior Publication Data
US 2015/0011469 A1   Jan. 8, 2015

Related U.S. Application Data

(63) and a continuation of application No. PCT/US2012/021802, filed on Jan. 19, 2012.

(60) Provisional application No. 61/675,692, filed on Jul. 25, 2012.

(51) Int. Cl.
| A61K 38/00 | (2006.01) |
| A61P 3/08 | (2006.01) |
| A61P 3/10 | (2006.01) |
| A61K 38/16 | (2006.01) |
| C07K 14/00 | (2006.01) |
| C07K 14/775 | (2006.01) |
| A61K 38/17 | (2006.01) |

(52) U.S. Cl.
CPC ............ C07K 14/775 (2013.01); A61K 38/16 (2013.01); A61K 38/1709 (2013.01)

(58) Field of Classification Search
None
See application file for complete search history.

(56) References Cited

U.S. PATENT DOCUMENTS

| 9,051,394 B2 | 6/2015 | Tso et al. |
| 2010/0267052 A1 | 10/2010 | Gelber et al. |
| 2014/0005107 A1 | 1/2014 | Tso et al. |
| 2015/0011469 A1 | 1/2015 | Tso et al. |
| 2015/0182591 A1* | 7/2015 | Tso et al. ............... A61K 38/22 |

FOREIGN PATENT DOCUMENTS

| WO | 1993/015198 A1 | 8/1993 |
| WO | 1994/027629 A1 | 12/1994 |
| WO | 2003/097696 A1 | 11/2003 |
| WO | 2009/116861 A2 | 9/2009 |
| WO | 2010060387 A1 | 6/2010 |
| WO | WO 2012028522 A1 * | 3/2012 ............... C13N 1/20 |
| WO | 2014/018079 A1 | 1/2014 |
| WO | 2014/018763 A2 | 1/2014 |

OTHER PUBLICATIONS

Unverified English language machine translation of WO93/15198, European Patent Office, available online at http://translationportal.epo.org/emtp/translate/?ACTION=description-retrieval&COUNTRY=WO&ENGINE=google&FORMAT=docdb&KIND=A1&LOCALE=en_EP&NUMBER=9315198&OPS=ops.epo.org/3.1&SRCLANG=fr&TRGLANG=en (accessed on Apr. 10, 2015).*
U.S. Appl. No. 14/704,418, filed May 2015, Tso et al.*
Wang et al., Proc. Natl. Acad. Sci. 109:9641-9646 (Jun. 2012).*
Costa et al., Frontiers in Microbiol. 5:1-20 (2014).*
Perkins, EJ, "Plasmids 101: Protein tags," available online at http://blog.addgene.org/plasmids-101-protein-tags, 8 pages (2014).*
Terpe, K., Appl. Microbiol. Biotechnol. 60:523-533 (2003).*
UniProt Database, Accession No. H2Q4U2, 8 pages (first available Mar. 2012).*
UniProt Accession No. P06727, 13 pages (sequence last modified in 2006).*
Vowinkel et al., J. Clin. Invest. 114:260-269 (2004).*
Deeb et al., Human Mutation 8:319-325 (1996).*
Joslin Diabetes Center, "Goals for Blood Glucose Control," available online at http://www.joslin.org/info/Goals-for-Blood-Glucose-Control.html, 1 pages (accessed on Sep. 29, 2017).*
www.aafp.org/afp/1999/0315/p1666.html, 2 pages (1999).*
Suen, et al: "The potential of incretin-based therapies in type 1 diabetes", Drug Discovery Today, vol. 17. No. 1, (2012), pp. 89-95.
Database Biosis, [Online] (2002), "Physiology of the small intestine in the glycemic control and the treatment of diabetes mellitus".
Fujimoto, K. et al., "Suppression of Food Intake by Apoliproprotein A-IV is Mediated through the Central Nervous System in Rats," J. Clin. Invest., 9:1830-1833 (1993).

(Continued)

*Primary Examiner* — Hasan Ahmed
*Assistant Examiner* — Thea D' Ambrosio
(74) *Attorney, Agent, or Firm* — Dinsmore & Shohl LLP

(57) ABSTRACT

Methods for treating type two diabetes mellitus in a subject in need thereof and pharmaceutical compositions for the treatment of type two diabetes mellitus are disclosed, wherein the methods and compositions of the invention are based on the use of non-glycosylated apolipoprotein A-IV produced by a protein expression system, such as a bacterial expression system. Also disclosed are methods for substantially restoring glucose tolerance in a subject in need thereof to a normal level and methods for lowering blood glucose levels in a subject in need thereof based on administering non-glycosylated apolipoprotein A-IV produced by a protein expression system.

9 Claims, 24 Drawing Sheets

(56) References Cited

OTHER PUBLICATIONS

Glatzle J, et al., Apolipoprotein A-IV stimulates duodenal vagal afferent activity to inhibit gastric motility via a CCK1 pathway, Am J Physiol Regul Integr Comp Physiol. 2004;287(2):R354-9.

Okumura T, et al., Apolipoprotein A-IV acts in the brain to inhibit gastric emptying in the rat, Am J Physiol. 1996; 270(1 Pt 1):G49-53.

Okumura T, et al: "Physiology of the small intestine in the glycemic control and the treatment of diabetes mellitus", Folia Pharmacologica Japonica, 120(1), 2002, pp. 29-31

Van Belle, et al: "Type 1 diabetes: etiology, immunology, and therapeutic strategies", Physiological Reviews 91(1), 2011, pp. 79-118.

International Search Report and Written Opinion issued in PCT/US2012/066314, (dated 2013).

NCBI Database; Accession No. P06727.3; GI: 93163358, Mar. 7, 2006.

Elshourbagy et al., "The Nucleotide and Amino Acid Sequence of Human Apolipoprotein A-IV mRNA and the Close Linkage of its Gene to the Genes of Apolipoproteins A-I and C-III," J. Biol. Chem. 261:1998-2002 (1986).

Fei, Wang et al., "Apolipoprotein A-IV improves glucose homeostasis by enhancing insulin secretion", Proceedings of the National Academy of Sciences—PNAS, 109(24): 9641-9646 (2012).

Mahley et al., "Plasma Lipoproteins: apolipoprotein and function," J. Lipid Res. 25:1277-1294 (1984).

University of Cincinnati Academic Health Center, "Diabetes Drug Target Identified", Health News, May 21, 2012, URL: http://healthnews.uc.edu/pdf/UC_HealthNews_20334.pdf, the whole document.

\* cited by examiner

EVSADQVATVMWDYFSQLSNNAKEAVEHLQKSELTQQLNALFQDKLGEVNTYAGDLQ
KKLVPFATELHERLAKDSEKLKEEIGKELEELRARLLPHANEVSQKIGDNLRELQQRLEP
YADQLRTQVNTQAEQLRRQLTPYAQRMERVLRENADSLQASLRPHADELKAKIDQNVE
ELKGRLTPYADEFKVKIDQTVEELRRSLAPYAQDTQEKLNHQLEGLTFQMKKNAEELK
ARISASAEELRQRLAPLAEDVRGNLRGNTEGLQKSLAELGGHLDQQVEEFRRRVEPYGE
NFNKALVQQMEQLRQKLGPHAGDVEGHLSFLEKDLRDKVNSFFSTFKEKESQDKTLSLP
ELEQQQEQQQEQQQEQVQMLAPLES

SEQ ID NO. 1

FIG. 15

EVTSDQVANVVWDYFTQLSNNAKEAVEQFQKTDVQQLSTLFASTYADGVHNKLVPFV
VQLSGHLAQETERVKEEIKKELEDLRDRKTQTFGENMQKLQEHLKPYAVDLQDQINTQ
TQEMKLQLTPYIQRMQTTIKENVDNLHTSMMPLATNLKDKFNRNMEELKGHLTPRANE
LKATIDQNLEDLRRSLAPLTVGVQEKLNHQMEGLAFQMKKNAEELQTKVSAKIDQLQK
NLAPLVEDVQSKVKGNTEGLQKSLEDLNRQLEQQVEEFRRTVEPMGEMFNKALVQQLE
QFRQQLGPNSGEVESHLSFLEKSLREKVNSFMSTLEKKGSPDQPQALPLPEQAQEQAQE
QAQEQVQPKPLES

SEQ ID NO. 2

FIG. 16

GEVSADQVATVMWDYFSQLSNNAKEAVEHLQKSELTQQLNALFQDKLGEVNTYAGDL
QKKLVPFATELHERLAKDSEKLKEEIGKELEELRARLLPHANEVSQKIGDNLRELQQRLE
PYADQLRTQVNTQAEQLRRQLTPYAQRMERVLRENADSLQASLRPHADELKAKIDQNV
EELKGRLTPYADEFKVKIDQTVEELRRSLAPYAQDTQEKLNHQLEGLTFQMKKNAEEL
KARISASAEELRQRLAPLAEDVRGNLRGNTEGLQKSLAELGGHLDQQVEEFRRRVEPYG
ENFNKALVQQMEQLRQKLGPHAGDVEGHLSFLEKDLRDKVNSFFSTFKEKESQDKTLS
LPELEQQQEQQQEQQQEQVQMLAPLES

SEQ ID NO. 3

FIG. 17

X₁EVSADQVATVMWDYFSQLSNNAKEAVEHLQKSELTQQLNALFQDKLGEVNTYAGD
LQKKLVPFATELHERLAKDSEKLKEEIGKELEELRARLLPHANEVSQKIGDNLRELQQRL
EPYADQLRTQVNTQAEQLRRQLTPYAQRMERVLRENADSLQASLRPHADX₂LKAKIDQ
NVEELKGRLTPYADEFKVKIDQTVEELRRSLAPYAQDTQEKLNHQLEGLTFQMKKNAE
ELKARISASAEELRQRLAPLAEDVRGNLRGNTEGLQKSLAELGGHLDQQVEEFRRRVEP
YGENFNKALVQQMEQLRQKLGPHAGDVEGHLSFLEKDLRDKVNSFFSTFKEKESQDKX
₃LSLPELEQQQEQX₃QEQQQEQVQMLAPLES $X_1$ is G, A, V or absent $X_2$ is E or K $X_3$ is T or S $X_4$ is Q or H

SEQ ID NO. 4

FIG. 18

```
GTCAGTGCTGACCAGGTGGCCACAGTGATGTGGGACTACTTCAGCCAGCTGAGCAA
CAATGCCAAGGAGGCCGTGGAACATCTCCAGAAATCTGAACTCACCCAGCAACTCA
ATGCCCTCTTCCAGGACAAACTTGGAGAAGTGAACACTTACGCAGGTGACCTGCAG
AAGAAGCTGGTGCCCTTTGCCACCGAGCTGCATGAACGCCTGGCCAAGGACTCGGA
GAAACTGAAGGAGGAGATTGGGAAGGAGCTGGAGGAGCTGAGGGCCCGGCTGCTG
CCCCATGCCAATGAGGTGAGCCAGAAGATCGGGGACAACCTGCGAGAGCTTCAGCA
GCGCCTGGAGCCCTACGCGGACCAGCTGCGCACCCAGGTCAACACGCAGGCCGAGC
AGCTGCGGCGCCAGCTGACCCCCTACGCACAGCGCATGGAGAGAGTGCTGCGGGAG
AACGCCGACAGCCTGCAGGCCTCGCTGAGGCCCCACGCCGACGAGCTCAAGGCCAA
GATCGACCAGAACGTGGAGGAGCTCAAGGGACGCCTTACGCCCTACGCTGACGAAT
TCAAAGTCAAGATTGACCAGACCGTGGAGGAGCTGCGCCGCAGCCTGGCTCCCTAT
GCTCAGGACACGCAGGAGAAGCTCAACCACCAGCTTGAGGGCCTGACCTTCCAGAT
GAAGAAGAACGCCGAGGAGCTCAAGGCCAGGATCTCGGCCAGTGCCGAGGAGCTG
CGGCAGAGGCTGGCGCCCTTGGCCGAGGACGTGCGTGGCAACCTGAGGGGCAACAC
CGAGGGGCTGCAGAAGTCACTGGCAGAGCTGGGTGGGCACCTGGACCAGCAGGTGG
AGGAGTTCCGACGCCGGGTGGAGCCCTACGGGGAAAACTTCAACAAAGCCCTGGTG
CAGCAGATGGAACAGCTCAGGCAGAAACTGGGCCCCATGCGGGGGACGTGGAAG
GCCACCTGAGCTTCCTGGAGAAGGACCTGAGGGACAAGGTCAACTCCTTCTTCAGC
ACCTTCAAGGAGAAAGAGAGCCAGGACAAGACTCTCTCCCTCCCTGAGCTCGAGCA
ACAGCAGGAACAGCAGCAGGAGCAGCAGCAGGAGCAGGTGCAGATGCTGGCCCCT
TTGGAGAGC
```

SEQ ID NO. 5

FIG. 19

FIG. 20: OmpA-Apo A-IV optimised sequence

```
                         M   K   K   T   A   I   A   I   A   V   L   A   G   F   A ·
   1 AGGAGGTAAA ACATATGAAA AAGACAGCTA TCGCGATTGC AGTGGCACTG GCTGGTTTCG
     · T   V   A   Q   E   V   S   A   D   Q   V   A   T   V   M   W   D   Y   F ·
  61 CTACCGTAGC GCAGGCCGAA GTAAGCGCAG ATCAGGTAGC AACGGTAATG TGGGATTATT
     · S   Q   L   S   N   N   A   K   E   A   V   E   H   L   Q   K   S   E   L   T ·
 121 TTAGCCAATT AAGCAACAAC GCAAAAGAGG CCGTGGAGCA CTTGCAGAAG AGCGAGCTGA
     · Q   Q   L   N   A   L   F   Q   D   K   L   G   E   V   N   T   Y   A   G   D ·
 181 CCCAGCAACT GAACGCTCTG TTCCAGGACA AGTTGGGTGA GGTTAACACG TATGCGGGCG
     · L   Q   K   K   L   V   P   F   A   T   E   L   H   E   R   L   A   K   D   S ·
 241 ATCTGCAGAA GAAACTGGTG CCGTTCGCGA CCGAACTGCA CGAGCGCCTG GCGAAGGATA
     · E   K   L   E   E   I   G   K   E   L   E   E   L   R   A   R   L   L   P ·
 301 GCGAGAAACT GAAGAACAG ATCGGCAAAG AGCTGGAAGA GCTGCGTGCG CGCCTGCTGC
     · H   A   N   E   V   S   Q   K   I   G   D   N   L   R   E   L   Q   Q   R   L ·
 361 CACATGCGAA CGAGGTGAGC CAAAAGATCG GTGACAATCT GCGCGAGCTG CAGCAGCGCC
     · E   P   Y   A   D   Q   L   R   T   Q   V   N   T   Q   A   E   Q   L   R   R ·
 421 TGGAGCCGTA CGCTGACCAG CTGCGTACCC AAGTTAACAC GCAAGCCGAG CAATTGCGTC
     · Q   L   T   P   Y   A   Q   R   M   E   R   V   L   R   E   N   A   D   S   L ·
 481 GTCAACTGAC TCCGTACGCG CAGCGTATGG AGCGTGTCCT GCGTGAGAAT GCGGACAGCC
     · Q   A   S   L   R   P   H   A   D   E   L   K   A   K   I   D   Q   N   V   E ·
 541 TGCAAGCATC CCTGCGTCCT CACGCGGATG AGCTGAAGGC AAAAATCGAC CAGAATGTTG
     · E   L   K   G   R   L   T   P   Y   A   D   E   F   K   V   K   I   D   Q   T ·
 601 AAGAACTGAA AGGTCGTCTG ACCCCGTACG CAGACGAGTT CAAAGTCAAA ATTGACCAAA
     · V   E   E   L   R   R   S   L   A   P   Y   A   Q   D   T   Q   E   K   L   N ·
 661 CGGTTGAAGA GTTGCGCCGC AGCCTGGCGC CGTATGCCCA GGATACCCAA GAAAAGCTGA
     · H   Q   L   E   G   L   T   F   Q   M   K   K   N   A   E   E   L   K   A   R ·
 721 ATCATCAGCT GGAAGGCCTG ACCTTCCAGA TGAAGAAGAA TGCCGAAGAG TTGAAAGCTC
     · I   S   A   S   A   E   E   L   R   Q   R   L   A   P   L   A   E   D   V   R ·
 781 GTATTTCGGC GTCTGCGGAA GAACTGCGCC AACGTCTGGC CCCGTTGGCG GAAGATGTGC
     · G   N   L   R   G   N   T   E   G   L   Q   K   S   L   A   E   L   G   G   H ·
 841 GCGGTAATCT GCGTGGCAAC ACCGAAGGTC TGCAAAAGAG CCTGGCCGAG TTGGGTGGCC
     · L   D   Q   Q   V   E   E   F   R   R   R   V   E   P   Y   G   E   N   F   N ·
 901 ATCTGGATCA ACAGGTTGAA GAATTTCGTC GTCGTGTGGA ACCGTACGGC GAGAACTTCA
     · K   A   L   V   Q   Q   M   E   Q   L   R   Q   K   L   G   P   H   A   G   D ·
 961 ATAAGGCGCT GGTGCAGCAA ATGGAGCAGC TGCGCCAGAA GCTGGGTCCG CACGCTGGTG
     · V   E   G   H   L   S   F   L   E   K   D   L   R   D   K   V   N   S   F   F ·
1021 ACGTCGAAGG TCACCTGTCC TTTCTGGAGA AAGACTTGCG TGATAAAGTC AATAGCTTCT
     · S   T   F   K   E   K   E   S   Q   D   K   T   L   S   L   P   E   L   E   Q ·
```

```
1081 TTTCTACGTT TAAAGAGAAA GAGAGCCAAG ACAAGACCCT GTCCCTGCCG GAGCTGGAAC
      ·  Q   Q   E    Q   Q   Q     E   Q   Q   Q     E   Q   V     Q   M   L     A   P   L   E ·

1141 AGCAACAGGA GCAGCAGCAG GAGCAACAGC AAGAACAAGT TCAGATGTTG GCACCGCTGG
                 XhoI

·  S                              (SEQ ID NO:12)

1201 AAAGCTAATG ACTCGAG                 (SEQ ID NO:13)
```

FIG. 20 (Continued)

FIG. 21: PelB-Apo A-IV optimised sequence

```
                         M  K  Y  L  L  P  T  A  A  G  L  L  L  L
  1 GAAGGAGATA TACATATGAA ATACCTGCTG CCGACCGCTG CTGCTGGTCT GCTGCTCCTC
       A  A  Q  P  A  M  A  E  V  S  A  D  Q  V  A  T  V  M  W  D
 61 GCTGCCCAGC CGGCGATGGC CGAAGTAAGC GCAGATCAGG TAGCAACGGT AATGTGGGAT
       Y  F  S  Q  L  S  N  N  A  K  E  A  V  E  H  L  Q  K  S  E
121 TATTTTAGCC AATTAAGCAA CAACGCAAAA GAGGCCGTGG AGCACTTGCA GAAGAGCGAG
       L  T  Q  Q  L  N  A  L  F  Q  D  K  L  G  E  V  N  T  Y  A
181 CTGACCCAGC AACTGAACGC TCTGTTCCAG GACAAGTTGG GTGAGGTTAA CACGTATGCG
                PstI
       G  D  L  Q  K  K  L  V  P  F  A  T  E  L  H  E  R  L  A  K
241 GGCGATCTGC AGAAGAAACT GGTGCCGTTC GCGACCGAAC TGCACGAGCG CCTGGCGAAG
       D  S  E  K  L  E  E  I  G  K  E  L  E  E  L  R  A  R  L
301 GATAGCGAGA AACTGAAAGA AGAGATCGGC AAAGAGCTGG AAGAGCTGCG TGCGCGCCTG
                                                          PstI
       L  P  H  A  N  E  V  S  Q  K  I  G  D  N  L  R  E  L  Q  Q
361 CTGCCACATG CGAACGAGGT GAGCCAAAAG ATCGGTGACA ATCTGCGCGA GCTGCAGCAG
       R  L  E  P  Y  A  D  Q  L  R  T  Q  V  N  T  Q  A  E  Q  L
421 CGCCTGGAGC CGTACGCTGA CCAGCTGCGT ACCCAAGTTA ACACGCAAGC CGAGCAATTG
       R  R  Q  L  T  P  Y  A  Q  R  M  E  R  V  L  R  E  N  A  D
481 CGTCGTCAAC TGACTCCGTA CGCGCAGCGT ATGGAGCGTG TCCTGCGTGA GAATGCGGAC
       S  L  Q  A  S  L  R  P  H  A  D  E  L  K  A  K  I  D  Q  N
541 AGCCTGCAAG CATCCCTGCG TCCTCACGCG GATGAGCTGA AGGCAAAAAT CGACCAGAAT
       V  E  E  L  K  G  R  L  T  P  Y  A  D  E  F  K  V  K  I  D
601 GTTGAAGAAC TGAAAGGTCG TCTGACCCCG TACGCAGACG AGTTCAAAGT CAAAATTGAC
       Q  T  V  E  E  L  R  R  S  L  A  P  Y  A  Q  D  T  Q  E  K
661 CAAACGGTTG AAGAGTTGCG CCGCAGCCTG GCGCCGTATG CCCAGGATAC CCAAGAAAAG
       L  N  H  Q  L  E  G  L  T  F  Q  M  K  K  N  A  E  E  L  K
721 CTGAATCATC AGCTGGAAGG CCTGACCTTC CAGATGAAGA AGAATGCCGA AGAGTTGAAA
       A  R  I  S  A  S  A  E  E  L  R  Q  R  L  A  P  L  A  E  D
781 GCTCGTATTT CGGCGTCTGC GGAAGAACTG CGCCAACGTC TGGCCCCGTT GGCGGAAGAT
       V  R  G  N  L  R  G  N  T  E  G  L  Q  K  S  L  A  E  L  G
841 GTGCGCGGTA ATCTGCGTGG CAACACCGAA GGTCTGCAAA AGAGCCTGGC CGAGTTGGGT
       G  H  L  D  Q  Q  V  E  E  F  R  R  R  V  E  P  Y  G  E  N
901 GGCCATCTGG ATCAACAGGT TGAAGAATTT CGTCGTCGTG TGGAACCGTA CGGCGAGAAC
       F  N  K  A  L  V  Q  M  E  Q  L  R  Q  K  L  G  P  H  A
961 TTCAATAAGG CGCTGGTGCA GCAAATGGAG CAGCTGCGCC AGAAGCTGGG TCCGCACGCT
       G  D  V  E  G  H  L  S  F  L  E  K  D  L  R  D  K  V  N  S
```

```
1021 GGTGACGTCG AAGGTCACCT GTCCTTTCTG GAGAAAGACT TGCGTGATAA AGTCAATAGC
      F  F  S  T    F  K  E    K  E  S    Q  D  K  T    L  S  L    P  E  L

1081 TTCTTTTCTA CGTTTAAAGA GAAAGAGAGC CAAGACAAGA CCCTGTCCCT GCCGGAGCTG
      E  Q  Q  Q    E  Q  Q    Q  E  Q    Q  Q  E  Q    V  Q  M    L  A  P

1141 GAACAGCAAC AGGAGCAGCA GCAGGAGCAA CAGCAAGAAC AAGTTCAGAT GTTGGCACCG
                      XhoI
      L  E  S                              (SEQ ID NO:14)

1201 CTGGAAAGCT AATGACTCGA G               (SEQ ID NO:15)
```

FIG. 21 (Continued)

FIG. 22: ENX-Apo A-IV optimised sequence

```
                          M  F  K  F  K  N  F  L  V

```
         L   S   L   P     E   L   E     Q   Q   Q     E   Q   Q   Q     E   Q   Q     Q   E   Q
~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
1141 CTGTCCCTGC CGGAGCTGGA ACAGCAACAG GAGCAGCAGC AGGAGCAACA GCAAGAACAA
                                              XhoI
         V   Q   M   L     A   P   L     E   S                                    (SEQ ID NO:16)
~~~~~~~~~~~~~~~~~~~~~~~~~~~~~~~~~~~~~~
1201 GTTCAGATGT TGGCACCGCT GGAAAGCTAA TGACTCGAG                                   (SEQ ID NO:17)
```

FIG. 22 (Continued)

FIG. 23: Apo A-IV optimised sequence

```
                              M   E   V   S   A   D   Q   V   A   T   V   M   W   D   Y   F  ·
  1 AGGAGGTAAA ACATATGGAA GTAAGCGCAG ATCAGGTAGC AACGGTAATG TGGGATTATT
    ·  S   Q   L   S   N   N   A   K   E   A   V   E   H   L   Q   K   S   E   L   T  ·
 61 TTAGCCAATT AAGCAACAAC GCAAAAGAGG CCGTGGAGCA CTTGCAGAAG AGCGAGCTGA
    ·  Q   Q   L   N   A   L   F   Q   D   K   L   G   E   V   N   T   Y   A   G   D  ·
121 CCCAGCAACT GAACGCTCTG TTCCAGGACA AGTTGGGTGA GGTTAACACG TATGCGGGCG
       PstI
    ·  L   Q   K   K   L   V   P   F   A   T   E   L   H   E   R   L   A   K   D   S  ·
181 ATCTGCAGAA GAAACTGGTG CCGTTCGCGA CCGAACTGCA CGAGCGCCTG GCGAAGGATA
    ·  E   K   L   K   E   E   I   G   K   E   L   E   E   L   R   A   R   L   L   P  ·
241 GCGAGAAACT GAAAGAAGAG ATCGGCAAAG AGCTGGAAGA GCTGCGTGCG CGCCTGCTGC
                                                               PstI
    ·  H   A   N   E   V   S   Q   K   I   G   D   N   L   R   E   L   Q   Q   R   L  ·
301 CACATGCGAA CGAGGTGAGC CAAAAGATCG GTGACAATCT GCGCGAGCTG CAGCAGCGCC
    ·  E   P   Y   A   D   Q   L   R   T   Q   V   N   T   Q   A   E   Q   L   R   R  ·
361 TGGAGCCGTA CGCTGACCAG CTGCGTACCC AAGTTAACAC GCAAGCCGAG CAATTGCGTC
    ·  Q   L   T   P   Y   A   Q   R   M   E   R   V   L   R   E   N   A   D   S   L  ·
421 GTCAACTGAC TCCGTACGCG CAGCGTATGG AGCGTGTCCT GCGTGAGAAT GCGGACAGCC
    ·  Q   A   S   L   R   P   H   A   D   E   L   K   A   K   I   D   Q   N   V   E  ·
481 TGCAAGCATC CCTGCGTCCT CACGCGGATG AGCTGAAGGC AAAAATCGAC CAGAATGTTG
    ·  E   L   K   G   R   L   T   P   Y   A   D   E   F   K   V   K   I   D   Q   T  ·
541 AAGAACTGAA AGGTCGTCTG ACCCCGTACG CAGACGAGTT CAAAGTCAAA ATTGACCAAA
    ·  V   E   E   L   R   R   S   L   A   P   Y   A   Q   D   T   Q   E   K   L   N  ·
601 CGGTTGAAGA GTTGCGCCGC AGCCTGGCGC CGTATGCCCA GGATACCCAA GAAAAGCTGA
    ·  H   Q   L   E   G   L   T   F   Q   M   K   K   N   A   E   E   L   K   A   R  ·
661 ATCATCAGCT GGAAGGCCTG ACCTTCCAGA TGAAGAAGAA TGCCGAAGAG TTGAAAGCTC
    ·  I   S   A   S   A   E   E   L   R   Q   R   L   A   P   L   A   E   D   V   R  ·
721 GTATTTCGGC GTCTGCGGAA GAACTGCGCC AACGTCTGGC CCCGTTGGCG GAAGATGTGC
    ·  G   N   L   R   G   N   T   E   G   L   Q   K   S   L   A   E   L   G   G   H  ·
781 GCGGTAATCT GCGTGGCAAC ACCGAAGGTC TGCAAAAGAG CCTGGCCGAG TTGGGTGGCC
    ·  L   D   Q   V   E   E   F   R   R   R   V   E   P   Y   G   E   N   F   N  ·
841 ATCTGGATCA ACAGGTTGAA GAATTTCGTC GTCGTGTGGA ACCGTACGGC GAGAACTTCA
    ·  K   A   L   V   Q   Q   M   E   Q   L   R   Q   K   L   G   P   H   A   G   D  ·
901 ATAAGGCGCT GGTGCAGCAA ATGGAGCAGC TGCGCCAGAA GCTGGGTCCG CACGCTGGTG
    ·  V   E   G   H   L   S   F   L   E   K   D   L   R   D   K   V   N   S   F   F  ·
961 ACGTCGAAGG TCACCTGTCC TTTCTGGAGA AAGACTTGCG TGATAAAGTC AATAGCTTCT
    ·  S   T   F   K   E   K   E   S   Q   D   K   T   L   S   L   P   E   L   E   Q  ·
```

```
1021 TTTCTACGTT TAAAGAGAAA GAGAGCCAAG ACAAGACCCT GTCCCTGCCG GAGCTGGAAC
      .  Q  Q  E    Q  Q  Q    E  Q  Q  Q    E  Q  V    Q  M  L    A  P  L  E  .
     ~~~~~~~~~~~~~~~~~~~~~~~~~~~~~~~~~~~~~~~~~~~~~~~~~~~~~~~~~~~~~~~~~~~~~~~~~~
1081 AGCAACAGGA GCAGCAGCAG GAGCAACAGC AAGAACAAGT TCAGATGTTG GCACCGCTGG
                      XhoI
                    ~~~~~~
                      AvaI
                    ~~~~~~
       .  S                          (SEQ ID NO:18)
     ~~~~
1141 AAAGCTAATG ACTCGAG              (SEQ ID NO:19)
```

FIG. 23 (Continued)

Output for 'Native'

```
Name: Native  Length: 396
MFLKAVVLTLALVAVAGARAEVSADQVATVMWDYFSQLSNNAKEAVEHLQKSELTQQLNALFQDKLGEVNTYAGDLQKKL      80
VPFATELHERLAKDSEKLKEEIGKELEELRARLLPHANEVSQKIGDNLRELQQRLEPYADQLRTQVNTQAEQLRRQLDPL     160
AQRMERVLRENADSLQASLRPHADELKAKIDQNVEELKGRLTPYADEFKVKIDQTVEELRRSLAPYAQDTQEKLNHQLEG     240
LTFQMKKNAEELKARISASAEELRQRLAPLAEDVRGNLKGNTEGLQKSLAELGGHLDQQVEEFRRRVEPYGENFNKALVQ     320
QMEQLRQKLGPHAGDVEGHLSFLEKDLRDKVNSFFSTFKEKESQDKTLSLPELEQQQEQQQEQQQEQVQMLAPLES
.............................................................................      80
.............................................................................     160
.............................................................................     240
.............................................................................     320
............................................................................      400

(Threshold=0.5)

No sites predicted in this sequence.
```

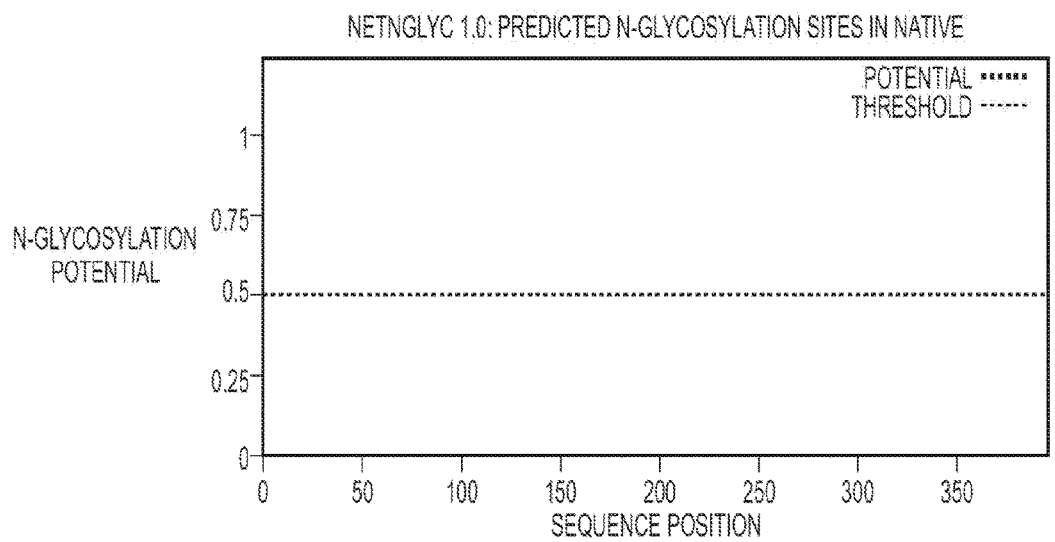

Figure 24A

```
Name:  1Missense_Pro_P__to_His_H__393   Length:  396
MFLKAVVLTLALVAVAGARAEVSADQVATVMWDYFSQLSNNAKEAVEHLQKSELTQQLNALFQDKLGEVNTYAGDLQKKL      80
VPFATELHERLAKDSEKLKEEIGKELEELRARLLPHANEVSQKIGDNLRELQQRLEPYADQLRTQVNTQAEQLRRQLDPL     160
AQRMERVLRENADSLQASLRPHADELKAKIDQNVEELKGRLTPYADEFKVKIDQTVEELRRSLAPYAQDTQEKLNHQLEG     240
LTFQMKKNAEELKARISASAEELRQRLAPLAEDVRGNLKGNTEGLQKSLAELGGHLDQQVEEFRRRVEPYGENFNKALVQ     320
QMEQLRQKLGPHAGDVEGHLSFLEKDLRDKVNSFFSTFKEKESQDKTLSLPELEQQQEQQQEQQQEQVQMLAHLES
.............................................................................      80
.............................................................................     160
.............................................................................     240
.............................................................................     320
...........................................................................       400

(Threshold=0.5)

No sites predicted in this sequence.
```

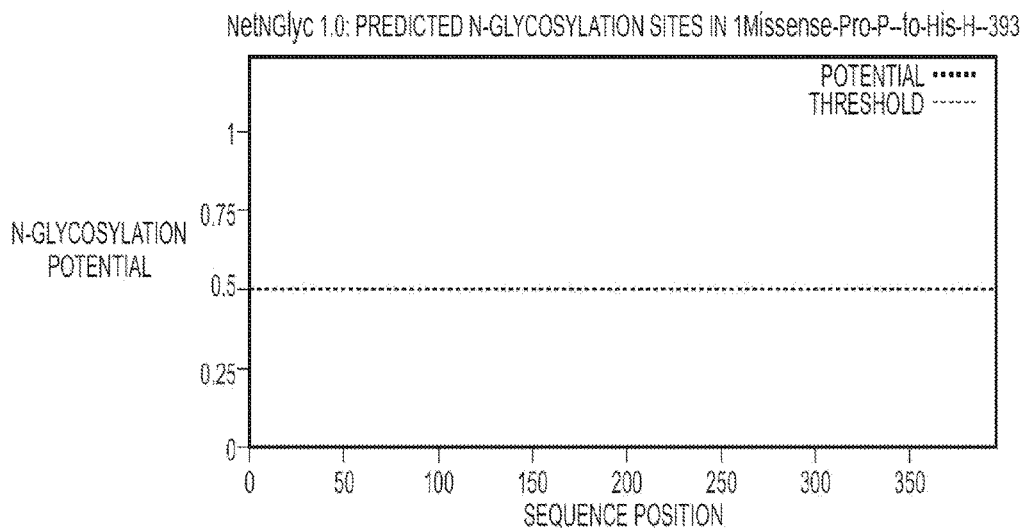

Figure 24B

METHOD OF TREATING DIABETES USING NON-GLYCOSYLATED APOLIPOPROTEIN A-IV

RELATED APPLICATIONS

This application claims priority to PCT Appln. No. PCT/US2012/066314, filed on Nov. 21, 2012. This application also claims priority to U.S. Provisional Patent Appln. No. 61/675,692, filed on Jul. 25, 2012. The entire contents of the priority applications are incorporated herein by reference in their entirety.

TECHNICAL FIELD

The present disclosure relates to a method of treating diabetes using non-glycosylated apolipoprotein A-IV (apoA-IV). More particularly, the present disclosure relates to a method of treating type two diabetes mellitus by administering an effective amount of non-glycosylated apoA-IV which is produced by a protein expression system.

BACKGROUND

The occurrence of diabetes is widespread, with approximately 8% of the population in the United States suffering from diabetes. Diabetes is a chronic disease characterized by high blood sugar due to the body's inability to effectively produce and/or use insulin. Diabetes can lead to a variety of physical complications, including but not limited to renal failure, blindness, nerve damage, heart disease, sleep apnea, and celiac disease. For example, in the United States, diabetes is the leading cause of renal failure, blindness, amputation, stroke, and heart attack. Also in the United States, diabetes is the sixth leading cause of death and has been shown to reduce the life expectancy of middle-aged adults by about five to ten years.

The most common form of diabetes is type 2 diabetes mellitus (also referred to as "T2DM" or "type 2 diabetes"). Type 2 diabetes is characterized by hyperglycemia, insulin resistance, β-cell dysfunction, and dysregulated hepatic gluconeogenesis. Persons suffering from type 2 diabetes experience a loss of glucose-stimulated insulin secretion related to the impaired release of stored insulin granules from β-cells in the first phase of insulin secretion. In the second phase of insulin secretion, persons suffering from type 2 diabetes experience a gradual loss of the ability to actively synthesize insulin in response to glucose stimuli.

The prevalence of type 2 diabetes is increasing and in 2002, type 2 diabetes resulted in greater than $130 billion in health care expenses. As such, new therapies for effectively treating type 2 diabetes are needed.

SUMMARY

The invention is based on the surprising discovery that the apolipoprotein A-IV (apoA-IV) protein is non-glycosylated in humans. Prior to the present disclosure, it was known in the art that the apoA-IV protein was glycosylated. Weinberg and Scanu ((1983) *J of Lipid Res* vol. 24:52) reported that apoA-IV was a glycoprotein containing 6% carbohydrate by weight (mannose 1.8%, galactose 1.55%, N-acetyl glucosamine 1.55%, sialic acid 1.1%). As such, apoA-IV is commonly described as a glycoprotein (see, for example, Gomaraschi et al. (2010) *Biochem Biophys Res Commun.* 393(1):126-30). In contrast, as described in Example 13 below, apoA-IV is a non-glycosylated protein.

Thus, in one embodiment, the invention provide methods of treating type 2 diabetes using non-glycosylated (also referred to as unglycosylated) apoA-IV protein. The method comprises administering to the subject an effective amount of a non-glycosylated apoA-IV protein, or a biologically active analogue or fragment thereof having at least 90, 95, 96, 97, 98 or 99% identity to the apoA-IV protein.

In one embodiment, non-glycosylated apoA-IV is produced using an expression system which lacks the ability to glycosylate. For example, a bacterial expression system, such as *Escherichia coli*, may be used to make non-glycosylated apoA-IV.

In another embodiment, cell expression systems that may be used to make non-glycosylated apoA-IV include, but are not limited to, mammalian cell expression systems, yeast expression systems and baculovirus expression systems. In another embodiment, a cell free expression system may be used to make non-glycosylated apoA-IV protein.

In another embodiment, a pharmaceutical composition comprising non-glycosylated apoA-IV protein is disclosed. The pharmaceutical composition comprises non-glycosylated apoA-IV protein having at least 90, 95, 96, 97, 98 or 99% identity to the apoA-IV protein, or a biologically active fragment thereof. The pharmaceutical composition may be formulated for administration to a subject for the treatment of type 2 diabetes.

In one embodiment, the invention provides a pharmaceutical composition comprising a non-glycosylated apoA-IV protein comprising an amino acid sequence as set forth in any one of SEQ ID NOs: 1, 3, 4, or 20 to 64 (or a sequence that is at least 90, 95, 96, 97, 98 or 99% identical to SEQ ID NO: 1, 3, 4, or 20-64), or a biologically active fragment thereof. In one embodiment, the invention provides a pharmaceutical composition comprising non-glycosylated apolipoprotein A-IV protein comprising an amino acid sequence as set forth in any one of SEQ ID NOs: 1, 3, 4, or 20-64, or an amino acid sequence which is at least 95% identical to any one of SEQ ID NOs: 1, 3, 4, or 20-64, or a biologically active fragment thereof. In another embodiment, the invention provides a pharmaceutical composition having an apolipoprotein A-IV protein comprising an amino acid sequence which is at least 96% identical to any one of SEQ ID NOs: 1, 3, 4, or 20-64, or a biologically active fragment thereof. In another embodiment, the invention provides a pharmaceutical composition having an apolipoprotein A-IV protein comprising an amino acid sequence which is at least 97% identical to any one of SEQ ID NOs: 1, 3, 4, or 20-64, or a biologically active fragment thereof. In another embodiment, the invention provides a pharmaceutical composition having an apolipoprotein A-IV protein comprising an amino acid sequence which is at least 98% identical to any one of SEQ ID NOs: 1, 3, 4, or 20-64, or a biologically active fragment thereof. In another embodiment, the invention provides a pharmaceutical composition having an apolipoprotein A-IV protein comprising an amino acid sequence which is at least 99% identical to any one of SEQ ID NOs: 1, 3, 4, or 20-64, or a biologically active fragment thereof.

In one embodiment, the pharmaceutical composition comprises a pharmaceutically acceptable carrier or diluent.

In another embodiment, the pharmaceutical composition is selected from the group consisting of a liquid formulation, an aqueous formulation, and a lyophilized formulation.

In one embodiment, the invention provides a method of treating type 2 diabetes comprising administering to a subject having type 2 diabetes a non-glycosylated apoA-IV protein, or a biologically active analogue or fragment thereof, having an amino acid sequence comprising an amino acid sequence as set forth in any one of SEQ ID NOs: 1, 3, 4, or 20 to 64 (or a sequence that is at least 90, 95, 96, 97, 98 or 99% identical to SEQ ID NO: 1, 3, 4, or 20-64). In a further embodiment, the apoA-IV protein is produced using a prokaryotic expression system, e.g., bacterial expression system such as E. coli.

In yet another embodiment, a method for substantially restoring glucose tolerance in a subject in need thereof to a normal level is disclosed. The method comprises administering to the subject an effective amount of non-glycosylated apoA-IV or a biologically active analogue or fragment thereof, having at least 90, 95, 96, 97, 98 or 99% identity to an apoA-IV protein, for example, by systemic administration of the non-glycosylated apoA-IV or the biologically active analogue or fragment thereof. In one embodiment, the invention provides a method for substantially restoring glucose tolerance in a subject in need thereof to a normal level, said method comprising administering an effective amount of a non-glycosylated apoA-IV protein (or a biologically active analogue or fragment thereof) having an amino acid sequence as set forth in any one of SEQ ID NOs: 1, 3, 4, or 20 to 64 (or an amino acid sequence that is at least 90, 95, 96, 97, 98 or 99% identical to SEQ ID NO: 1, 3, 4, or 20-64.

In yet still another embodiment, a method for lowering blood glucose level in a subject in need thereof is disclosed. The method comprises administering to the subject an effective amount of non-glycosylated apoA-IV or a biologically active analogue or fragment thereof having at least 90, 95, 96, 97, 98 or 99% identity to the non-glycosylated apoA-IV to the subject in need, for example, by systemic administration. In one embodiment, the invention provides a method for lowering blood glucose level in subject a subject in need thereof, the method comprising administering to the subject an effective amount of non-glycosylated apoA-IV (or a biologically active analogue or fragment thereof) comprising an amino acid sequence set forth in SEQ ID NOs: 1, 3, 4, or 20 to 64 (or a sequence that is at least 90, 95, 96, 97, 98 or 99% identical to SEQ ID NO: 1, 3, 4, or 20-64).

An "effective amount" is as described below and may include about 0.25 to 2 µg/g of the apoA-IV or the biologically active analogue thereof. In one embodiment the effective amount is about 0.1 mg/kg to 25 mg/kg. In another embodiment, the effective amount is a fixed dose of about 1 to 1000 mg. In a further embodiment, the effective amount is a fixed dose of about 1 to 10 mg.

These and other features and advantages of these and other various embodiments according to the present disclosure will become more apparent in view of the drawings, detailed description, and claims provided herein.

BRIEF DESCRIPTION OF THE DRAWINGS

The following detailed description of the embodiments of the present disclosure can be better understood when read in conjunction with the following drawings, where like structure is indicated with like reference numerals, and in which:

FIG. 15 is a protein with the amino acid sequence of full length wild type human apoA-IV (SEQ ID NO. 1).

FIG. 16 is a protein with the amino acid sequence of full length wild type mouse apoA-IV (SEQ ID NO. 2).

FIG. 17 is a protein having the amino acid sequence of full length wild type human apoA-IV with the addition of glycine at the N-terminus (SEQ ID NO. 3).

FIG. 18 is a protein with the amino acid sequence of human apoA-IV showing polymorphic substitutions T347S, Q360H, and/or E165K and the optional addition of glycine, alanine or valine to the N-terminus (SEQ ID NO. 4).

FIG. 19 is a polynucleotide (SEQ ID NO. 5) encoding full length wild type human apolipoprotein A-IV.

FIG. 20 includes the amino acid sequence and optimized nucleotide coding sequence of the Omp-Apo A-IV construct for periplasmic expression in E. coli.

FIG. 21 includes the amino acid sequence and optimized nucleotide coding sequence of PelB-Apo A-IV construct for periplasmic expression in E. coli.

FIG. 22 includes the amino acid sequence and optimized nucleotide coding sequence of ENX-Apo A-IV construct for periplasmic expression in E. coli.

FIG. 23 includes the amino acid sequence and optimized nucleotide coding sequence of Apo A-IV construct for cytoplasmic expression in E. coli.

FIGS. 24A and B show N-glycosylation prediction results for the human wild type apoA-IV (SEQ ID NO:65) (FIG. 24A) and variant P393H (SEQ ID NO: 20) (FIG. 24B).

Figure 1:
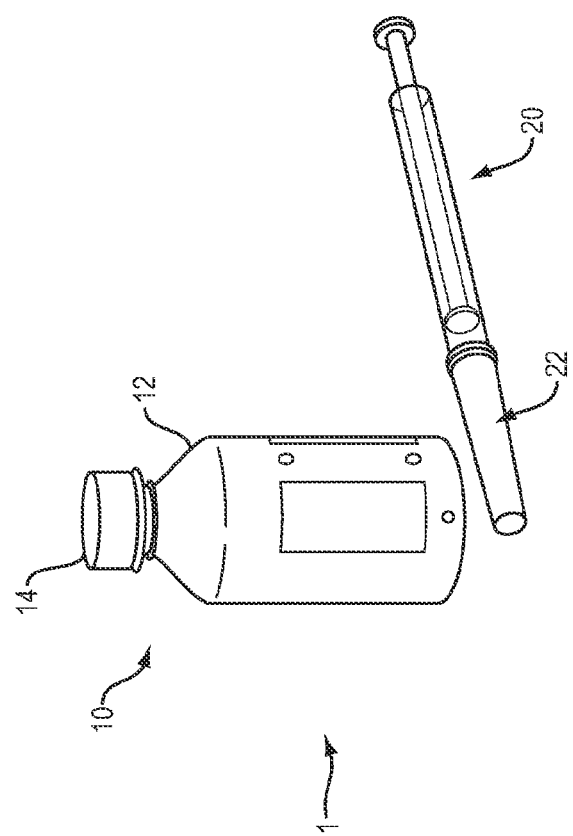
FIG. 1 is a side perspective view of a device having a reservoir of a pharmaceutical composition and a syringe according to an embodiment of the present disclosure.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present disclosure.

DETAILED DESCRIPTION

The following terms are used in the present application:

As used herein, the term "non-glycosylated" or "unglycosylated" means a protein without observable N-linked glycosylation and/or O-linked glycosylation, within the limits of detection, for example, by isoelectric focusing, PNGase F digestion and/or MALDI analysis. In one embodiment, the term "non-glycosylated" or "unglycosylated" means without observable N-linked glycosylation and without observable O-linked glycosylation. In another embodiment, the term "non-glycosylated" or "unglycosylated" means without observable N-linked glycosylation. In another embodiment, the term "non-glycosylated" or "unglycosylated" means without observable O-linked glycosylation.

As used herein, the term "protein expression system" refers to a cell-based or non-cell-based expression system that is used to produce a protein of interest, e.g., apoA-IV. Given that apoA-IV has been surprisingly found to lack glycosylation, expression systems that lack glycosylation machinery may be used to produce the protein for use in the treatment of type II diabetes. In one embodiment, cell-based expression systems which do glycosylate, such as mammalian cells, may be used to produce non-glycosylated apoA-IV. In one embodiment, the protein expression system used to make apoA-IV includes either a bacterial expression system, a mammalian cell expression system, a baculovirus (insect) cell expression system, or a yeast expression system.

The term "recombinant host cell" (or simply "host cell"), as used herein, refers to a cell that has been transformed, or is capable of being transformed, with a nucleic acid sequence and thereby expresses a gene of interest, e.g., apoA-IV. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Host cells may be prokaryotic or eukaryotic cells that are capable of expressing exogenous nucleic acid sequences. Examples of host cells include bacteria such as E. coli, yeast, plant cells, Chinese hamster ovary (CHO) cells, human embryonic kidney (HEK)-293 cells and insect cells.

The term "isolated" as it is used in reference to a protein, is a protein, polypeptide or antibody that by virtue of its origin or source of derivation: (1) is not associated with naturally associated components that accompany it in its native state; (2) is free of other proteins from the same species; (3) is expressed by a cell from a different species; or (4) does not occur in nature. Thus, a polypeptide that is, e.g., chemically synthesized or synthesized in a cellular system different from the cell from which it naturally originates will be "isolated" from its naturally associated components. A protein may also be rendered substantially free of naturally associated components by isolation, using any suitable protein purification technique. In one embodiment, the apoA IV protein used in the compositions and methods of the invention is an isolated protein obtained from a recombinant host cell, e.g., a bacterial cell.

The phrase "percent identical" or "percent identity" refers to the similarity (e.g., 95%, 96%, 97%, 98%, or 99%) between at least two different sequences. This percent identity can be determined by standard alignment algorithms, for example, the Basic Local Alignment Search Tool (BLAST) described by Altshul et al. ((1990) J. Mol. Biol. 215:403-10); the algorithm of Needleman et al. ((1970) J. Mol. Biol. 48:444-53); or the algorithm of Meyers et al. ((1988) Comput. Appl. Biosci. 4:11-17). A set of parameters may be, for example, the Blosum 62 scoring matrix with a gap penalty of 12, a gap extend penalty of 4, and a frameshift gap penalty of 5. The percent identity between two amino acid or nucleotide sequences can also be determined using the algorithm of Meyers and Miller ((1989) CABIOS 4:11-17), which has been incorporated into the ALIGN program (version 2.0), using a PAM120 weight residue table, a gap length penalty of 12, and a gap penalty of 4.

The term "recombinant protein" refers to a protein molecule that is expressed from recombinant DNA. For example, a recombinant ApoA-IV protein is one that is expressed in a recombinant host cell. Preferably, the ApoA-IV protein used in the methods and compositions of the invention is a recombinant ApoA-IV protein.

As used herein, the term "effective amount" describes the amount necessary or sufficient to realize a desired biologic effect. The effective amount for any particular application may vary depending on a variety of factors, including but not limited to the particular composition being administered, the size of the subject, and/or the severity of the disease and/or condition being treated. In one embodiment, an "effective amount" is a dose of about 0.25 to 10 µg/g of a non-glycosylated apoA-IV or biologically active analogue thereof. Alternatively, an "effective amount of a non-glycosylated apoA-IV or a biologically active analogue thereof is about 1 to 10 µg/g, about 0.25 to 2 µg/g, about 1 µg/g, or 0.1 mg/kg to 25 mg/kg. In another embodiment, the effective amount is a fixed dose of about 1 to 1000 mg. In a further embodiment, the effective amount is a fixed dose of about 1 to 10 mg.

Non-glycosylated apoA-IV or a biologically active analogue is administered one time daily. Alternatively, non-glycosylated apoA-IV or a biologically active analogue thereof is administered about 2 times per day. In yet another alternative, non-glycosylated apoA-IV or a biologically active analogue thereof is administered more than twice a day, for example, three times per day. In yet another alternative, non-glycosylated apoA-IV is administered once every second, third, fourth, fifth or sixth day, or once weekly.

As used herein, the term "desired biologic effect" describes reducing the effects of, counteracting, and/or eliminating a disease or condition. For example, in the context of type 2 diabetes, desired biologic effects include, but are not limited to lowering blood glucose, improving glucose tolerance, substantially restoring glucose tolerance to a normal level, improving insulin secretion, and/or substantially restoring insulin secretion to a normal level.

As used herein, the term "normal level" describes a level that is substantially the same as the level in a subject who is not in need of treatment. For example, in the context of treating type 2 diabetes, a normal level of blood glucose is from about 70 mg/dL to about 130 mg/dL before meals and less than about 180 mg/dL about one to two hours after meals, or from about 70 mg/dL to about 100 mg/dL before meals and less than about 140 mg/dL about one to two hours after meals. In another example in the context of treating type 2 diabetes, a normal level of glucose tolerance describes the ability of the subject to metabolize carbohydrates such that the level of blood glucose is from about 70 mg/dL to about 130 mg/dL before meals and less than about 180 mg/dL about one to two hours after meals, or from about 70 mg/dL to about 100 mg/dL before meals and less than about 140 mg/dL about one to two hours after meals. In still another example in the context of treating type 2 diabetes, the normal level of insulin secretion is the amount required to maintain a normal level of glucose tolerance, wherein the level of insulin secretion is greater than about 1 ng/mL about fifteen hours after meals. In a further embodiment, a normal level of blood glucose is from about 70 mg/dl to 100 mg/dl for a morning fasting blood sugar test.

In the context of blood glucose level, the term "restore" describes changing the blood glucose level of a subject to a normal level. Similarly, in the context of glucose tolerance, the term "restore" describes changing the glucose tolerance of a subject to a normal level. Also, in the context of insulin secretion, "restore" describes changing the insulin secretion of a subject to a normal level.

In the context of non-glycosylated apoA-IV, the term "biologically active fragment" describes a fragment of non-glycosylated apoA-IV which is capable of realizing a desired biologic effect in a subject with type 2 diabetes. The term "biologically active analogue" describes an analogue of non-glycosylated apoA-IV which is capable of realizing a desired biologic effect in a subject with type 2 diabetes. In one example, a desired biological effect is to restore glucose tolerance in apoA-IV knockout mice as described in Example 2. Another example of a desired biological effect is to cause a statistically significant lowering of abnormal glucose levels in an animal model of type 2 diabetes, such as the mouse model described in Example 7.

As used herein, the term "obese" describes a condition in which a subject is well above a normal weight. In one specific example, the term obese describes a condition in which a subject is more than about 20% over their ideal weight and/or has a body mass index of about thirty or greater than about thirty. In one embodiment, the subject being treated is obese; in another embodiment, the subject being treated is not obese; and in yet another embodiment, the subject being treated has a normal body weight.

Embodiments of the present disclosure relate to methods for treating type 2 diabetes in a subject in need thereof and pharmaceutical compositions for the treatment of type 2 diabetes. In one embodiment, a method of treating diabetes is disclosed. In one particular embodiment, a method of treating type 2 diabetes in a subject in need thereof is disclosed, wherein the method comprises administering an effective amount of non-glycosylated apolipoprotein A-IV (hereinafter "apoA-IV") or a biologically active analogue or fragment thereof to the subject.

In one embodiment, the method of treating type 2 diabetes is effective to lower blood glucose level of a subject. In one particular embodiment, the method is effective to lower blood glucose level of a subject by about 20 to 50%. In a further embodiment, the method is effective to lower the blood glucose level of a subject by about 40%. In a further embodiment, the method is effective to lower the blood glucose level of a subject by about 70%. In still a further embodiment, the method is effective to substantially restore blood glucose level to a normal level.

In one embodiment, the method of treating type 2 diabetes results in a lower blood glucose level of a subject. In one particular embodiment, the method is effective to lower blood glucose level of a subject by about 1 mg/dl, 2 mg/dl, 3 mg/dl, 4 mg/dl, 5 mg/dl, 6 mg/dl, 7 mg/dl, 8 mg/dl, 9 mg/dl, 10 mg/dl, 11 mg/dl, 12 mg/dl, 13 mg/dl, 14 mg/dl, 15 mg/dl, 16 mg/dl, 17 mg/dl, 18 mg/dl, 19 mg/dl, 20 mg/dl, 40 mg/dl, 60 mg/dl, 80 mg/dl, 100 mg/dl, 120 mg/dl, 140 mg/dl, 160 mg/dl, 180 mg/dl, 200 mg/dl, 220 mg/dl, or 240 mg/dl, from a baseline level over the course of the dosing interval.

In another embodiment, the method of treating type 2 diabetes is effective to substantially restore glucose tolerance of a subject to a normal level. In one particular embodiment, the method is effective to substantially restore glucose tolerance of a subject to a normal level within about two hours after administration of a dose of non-glycosylated apoA-IV or a biologically active analogue thereof. In another embodiment, the method is effective to substantially restore glucose tolerance of a subject to a normal level within about three hours or within about four hours after administration of a dose of an apoA-IV or a biologically active analogue thereof. In another embodiment, the glucose tolerance of a subject is substantially restored to a normal level for about eight to twelve hours.

In yet another embodiment, the treatment is effective to substantially restore insulin secretion to a normal level. In one particular embodiment, the treatment is effective to substantially restore insulin secretion to a normal level within about two hours after the administration of a dose of non-glycosylated apoA-IV or a biologically active analogue or fragment thereof. In another embodiment, insulin secretion is substantially restored to a normal level for about eight to twelve hours. In still another embodiment, the treatment is effective to lower the level of C-reactive protein.

In one embodiment, non-glycosylated apoA-IV or a biologically active analogue thereof is administered systemically. Systemic administration of the non-glycosylated apoA-IV or the analogue thereof is selected from the group consisting of oral, subcutaneous, intravenous, intramuscular, and intraperitoneal administration.

In another embodiment, a pharmaceutical composition is disclosed. In one particular embodiment, the pharmaceutical composition comprises non-glycosylated apoA-IV or a biologically active analogue or fragment thereof. In another embodiment, the non-glycosylated apoA-IV or analogue thereof is formulated for administration to a subject for the treatment of type 2 diabetes. In this particular embodiment, a method for treating type 2 diabetes in a subject in need thereof is also provided, wherein the method comprises administering an effective amount of the pharmaceutical composition to the subject.

An "apolipoprotein A-IV" refers to mammalian apoA-IV and includes full-length apoA-IV and biologically active fragments of apoA-IV. The full-length human apoA-IV protein is a 376 amino acid protein (SEQ ID NO: 1), the amino acid sequence of which is shown in FIG. 15 and the molecular weight of which is 43.4 kDa. The amino acid sequence of full length mouse apoA-IV protein (SEQ ID NO. 2) is shown in FIG. 16. Also encompassed by the term "apolipoprotein A-IV" is the known analogue in which a glycine is added to N-terminus of the apoA-IV of the full length human sequence (SEQ ID NO. 3, as shown in FIG. 17), and analogues thereof having conservative substitutions for the N-terminal glycine (such as alanine and valine). An "apolipoprotein A-IV" also includes polymorphic forms thereof, including T347S, Q360H, or E165K substitutions to the human sequence represented by SEQ ID NO. 1 or the corresponding positions of SEQ ID NO. 3. As such, "apolipoprotein A-IV" includes the protein of SEQ ID NO. 4, shown in FIG. 18. In addition, human "apolipoprotein A-IV" includes variants (SEQ ID NOs: 20-64) each with a missense mutation: P393H, Q385K, Q381K, Q380H, Q377P, T367S, S353A, N352Y, V336M, D335H, G311R, V307L, R305C, R304Q, E291G, V274M, V274A, R264Q, A260T, E250K, N235S, Q231K, R220C, Q214H, E207K, T202M, R200C, D191N, D184N, P181L, A172T, R169W, A161S, R154W, T148M, S147N, A139E, N127K, S95L, R90C, T85A, Q77H, G74S, V13M, or V6M, as shown below in Table 1. SEQ ID NOs: 20-65 include the signal sequence. In one embodiment, the methods and compositions described herein include the mature forms of the proteins described in SEQ ID NOS: 20-65.

In one embodiment, the methods and compositions described herein use a non-glycosylated ApoA-IV protein comprising an amino acid sequence selected from the group consisting of 1, 3, 4, or 20-64, or a biologically active fragment thereof. Alternatively, the methods and compositions described herein use a non-glycosylated ApoA-IV protein comprising an amino acid sequence having at least 95%, 96%, 97%, 98%, or 99% identity to a sequence selected from the group consisting of 1, 3, 4, or 20-64, or a biologically active fragment thereof.

A biologically active analogue of apoA-IV has at least 90, 95, 96, 97, 98 or 99% identity to an apoA-IV. As described in the previous paragraph, an apoA-IV includes full length mammalian apoA-IV (e.g., human or mammalian) (human is described in SEQ ID NO: 1), polymorphic forms thereof, the protein of SEQ ID NOS. 3 and 4, and biologically active fragments of any of the foregoing Amino acid variations in the biologically active analogues preferably have conservative substitutions relative to the wild type sequences. A "conservative substitution" is the replacement of an amino acid with another amino acid that has the same net electronic charge and approximately the same size and shape. Amino acid residues with aliphatic or substituted aliphatic amino acid side chains have approximately the same size when the total number of carbon and heteroatoms in their side chains differs by no more than about four. They have approximately the same shape when the number of branches in their side chains differs by no more than one. Amino acid residues with phenyl or substituted phenyl groups in their side chains are considered to have about the same size and shape. Listed below are five groups of amino acids. Replacing an amino acid residue with another amino acid residue from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidine substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

An apoA-IV or a biologically active analogue thereof is preferably unglycosylated. The preparation of recombinant unglycosylated human and mouse apoA-IV is described in Example 12. The polynucleotide sequence of full length wild type human apolipoprotein (SEQ ID NO. 1) is shown as SEQ ID NO. 5 in FIG. 19.

ApoA-IV used in Examples 1-10 is unglycosylated. Non-glycosylated apoA-IV may be prepared according to standard methods known in the molecular biology field. For example, non-glycosylated apoA-IV may be prepared via traditional molecular cloning techniques.

In one embodiment, apoA-IV is prepared according to the methods described in Tubb et al. (2009) *J of Lipid Res* 50:1497, where the authors expressed recombinant apoA-IV with an affinity tag (Histidine (His) tag) in a bacterial expression system, i.e., *E. coli*. Tubb et al. describe the use of the tobacco etch virus (TEV) protease as a means for cleaving the His tag from the apoA-IV protein. Thus, the apoA-IV protein may be expressed in a recombinant host cell, e.g., *E. coli*, using a His tag which is cleaved by the TEV protease. Alternatively, the apoA-IV protein may be expressed in a recombinant host cell, e.g., *E. coli*, using a glutatione S-transferase (GST) tag which is cleaved by the TEV protease. In one embodiment, the TEV protease is used to cleave an affinity tag from the apoA-IV protein.

In one embodiment, a bacterial host may be used to produce unglycosylated apoA-IV. Examples of bacterial hosts include, but are not limited to, *E. coli* BL-21, BL-21 (DE3), BL21-AI™, BL21(DE3)pLysS, BL21(DE3)pLysE, BL21 Star™ (DE3), and BL21 Star™ (DE3)pLysS, (Invitrogen). *Corynebacterium* may also be used as a host cell for expressing apoA-IV. Prior to transformation into the bacterial host, the DNA segment encoding ApoA-IV or its analogue may be incorporated in any of suitable expression vectors for transformation into the bacterial host. Suitable expression vectors include plasmid vectors, cosmid vectors, and phage vectors variously known to those of skill in the art, for example, as described in Sambrook, et al., Molecular Cloning Manual, 2d Edition, 1989. Examples of the expression vector include pET Vectors (Invitrogen), pDEST vectors (Invitrogen), pRSET vectors (Invitrogen), and pJexpress Vector (DNA2.0 Inc.). In one embodiment, *E. Coli* BL-21 (DE3) is transformed with pET30 expression vector which contains the gene encoding the ApoA-IV.

In addition to prokaryotes, eukaryotic microbes such as filamentous fungi or yeast are suitable cloning or expression hosts for apoA-IV-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K.*

*drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of apoA-IV may also be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

Another suitable host cell for production of apoA-IV protein is a vertebrate cell. Examples of useful mammalian host cell lines include, but are not limited to, monkey kidney CV1 line transformed by SV40 (COS-7, ATCC CRL 1651); human embryonic kidney line (e.g., 293 or 293 cells subcloned for growth in suspension culture, Graham et al., J. Gen Virol. 36:59 (1977)); baby hamster kidney cells (BHK, e.g., ATCC CCL 10); Chinese hamster ovary cells/-DHFR (CHO, Urlaub et al., Proc. Natl. Acad. Sci. USA 77:4216 (1980)), including, but not limited to CHO K1, CHO pro3.sup.−, CHO DG44, CHO DUXB11, Lec13, B-Ly1, and CHO DP12 cells, preferably a CHO DUX (DHFR−) or subclone thereof (herein called "CHO DUX"); C127 cells, mouse L cells; Ltk.sup.-cells; mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse myeloma cells; NS0; hybridoma cells such as mouse hybridoma cells; COS cells; mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with expression or cloning vectors for production of the apoA-IV protein, and cultured in conventional nutrient media modified as appropriate for inducing promoters, selecting transformants, or amplifying the genes encoding the desired sequences.

ApoA-IV knockout mice used in the examples were generated according to procedures disclosed in *J Lipid Res.* 1997 September; 38(9):1782-94, the entire teachings of which are incorporated herein by reference.

Also included in the methods of the invention are combination therapies for treating type 2 diabetes. Examples of additional therapeutic agents that may be used in combination with apolipoprotein A-IV include, but are not limited to, sulfonylureas, meglitinides, biguanides, thiazolidinediones, alpha-glucosidase inhibitors, DPP-4 inhibitors, incretin mimetics, and insulin. An additional therapeutic agent may be administered prior to, concurrently with, or subsequent to administration of apoA-IV to the subject in need thereof.

The effective amount or apoA-IV administered to a subject for the treatment of type 2 diabetes may, for example, be a weight-based dose (e.g., mg/kg) or, in another example, be a fixed dose (non-weight dependent). In one embodiment, about 1 to 10 mg/kg, about 0.25 to 2 mg/kg, about 1 mg/kg, or 0.1 mg/kg to 25 mg/kg of apoA-IV is administered to a subject in need thereof. In another embodiment, the effective amount of apoA-IV administered to a subject in need thereof is a fixed dose of about 1 to 1000 mg. In a further embodiment, the effective amount is a fixed dose of apoA-IV administered to a subject in need thereof, is about 1 mg, 2 mg, 3 mg, 4 mg, 5 mg, 6 mg, 7 mg, 8 mg, 9 mg, 10 mg, 11, mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 40 mg, 50 mg, 60 mg, 70 mg, 80 mg, 90 mg, 100 mg, 120 mg, 140 mg, 160 mg, 180 mg, 200 mg, 250 mg, 300 mg, 350 mg, 400 mg, 450 mg, 500 mg, 550 mg 600 mg, 650 mg, 700 mg, 750 mg, 800 mg, 850 mg, 900 mg, 950 mg, or 1000 mg.

In one particular embodiment, the pharmaceutical composition may further comprise a pharmaceutically acceptable carrier. Pharmaceutically acceptable carriers include a wide range of known diluents (i.e., solvents), fillers, extending agents, binders, suspending agents, disintegrates, surfactants, lubricants, excipients, wetting agents and the like commonly used in this field. The pharmaceutical composition is preferably aqueous, i.e., is a liquid formulation, and preferably comprises pyrogen free water. These carriers may be used singly or in combination according to the form of the pharmaceutical preparation. The resulting preparation may incorporate, if necessary, one or more solubilizing agent, buffers, preservatives, colorants, perfumes, flavorings and the like that are widely used in the field of pharmaceutical preparation.

The non-glycosylated apoA-IV or biologically active analogue thereof may be formulated into a dosage form selected from the group consisting of tablets, capsules, granules, pills, injections, solutions, emulsions, suspensions, and syrups. The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

The pharmaceutical composition of the invention for treating type 2 diabetes may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The proportion of the active ingredient to be contained in the pharmaceutical composition of the invention for treating type 2 diabetes can be suitably selected from a wide range.

In one particular embodiment, the subject in need of treatment of type 2 diabetes is a mammal. The mammal may be selected from the group consisting of humans, non-human primates, canines, felines, murines, bovines, equines, porcines, and lagomorphs. In one specific embodiment, the mammal is human. In another embodiment, non-glycosylated apoA-IV or a biologically active analogue thereof may be administered to a subject for the treatment of type 2 diabetes wherein the subject is obese. Alternatively, non-glycosylated apoA-IV may be administered to a subject for the treatment of type 2 diabetes wherein the subject is not obese.

Referring to FIG. 1, in yet another embodiment, a device 1 is disclosed. In one embodiment, the device 1 comprises a reservoir 10 of the pharmaceutical composition previously discussed above. In a further embodiment, the reservoir 10 comprises a vial 12. The vial 12 may be formed of any material that does not inhibit the function of the pharmaceutical composition. For example, the vial 12 may comprise glass and/or plastic. Additionally, the vial 12 may comprise a pierceable septum 14 through which the pharmaceutical composition may be removed. In use, the septum 14 of the vial is pierced by the needle 22 of a syringe 20, the pharmaceutical composition is removed by the syringe 20 from the vial 12, and the pharmaceutical composition is administered via injection to a subject in need.

EXAMPLES

The following non-limiting examples illustrate the methods of the present disclosure.

Example 1: Glucose Intolerance of ApoA-IV Knockout Mice

Experimental Protocol.

Male apoA-IV knockout ("hereinafter "KO") mice were obtained. Wild-type (hereinafter "WT") mice served as controls. ApoA-IV KO and WT mice were obtained from a colony kept at the University of Cincinnati (Cincinnati, Ohio). ApoA-IV KO and WT mice were fed a chow diet. Prior to performing the glucose tolerance tests, ApoA-IV KO mice and WT mice were fasted for five hours. In the glucose tolerance tests, the apoA-IV KO mice and WT mice were injected intraperitoneally with a dose of about 2 mg/g body weight of glucose and plasma glucose was measured at about 0, 15, 30, 60, and 120 minutes following the injection of glucose. The glucose tolerance tests were performed twice, once at three months of age and again at sixteen months of age.

Experimental Results.

Figure 2:
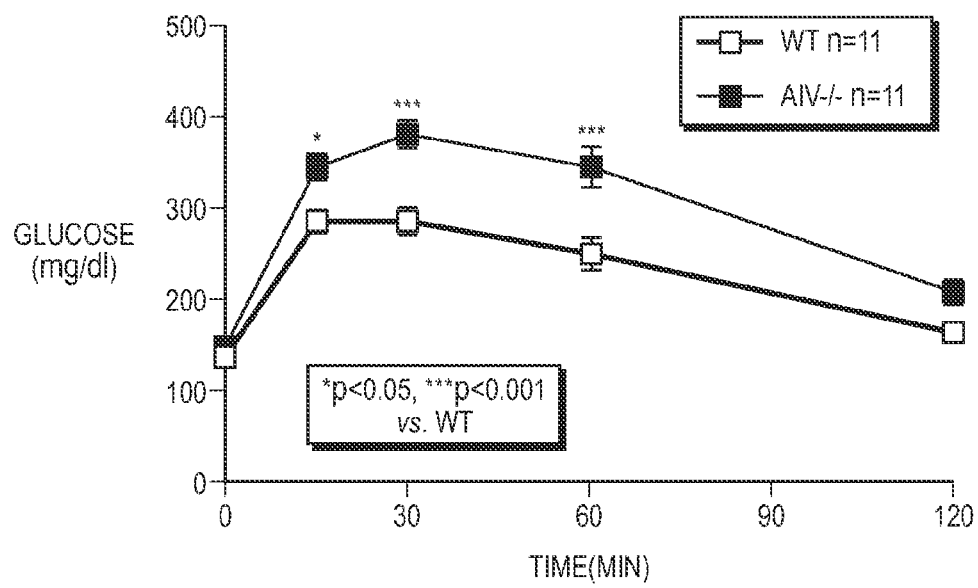
FIG. 2 is a graph of plasma glucose (mg/dL) in male apoA-IV knockout and wild-type mice with respect to time (min) for an intraperitoneal glucose tolerance test.
Figure 3:
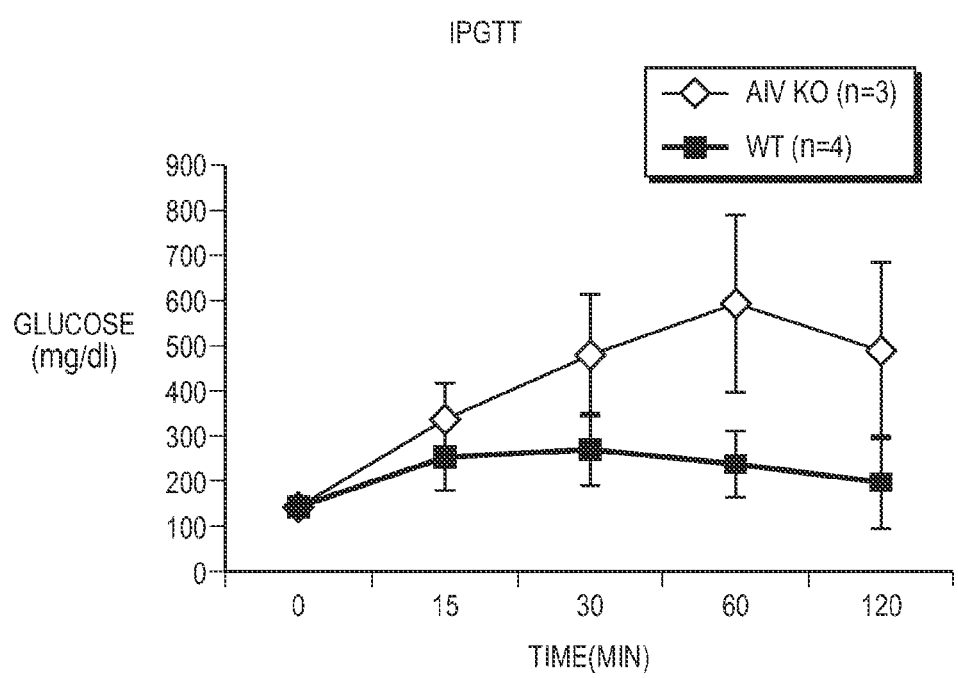
FIG. 3 is a graph of plasma glucose (mg/dL) with respect to time (min) for an intraperitoneal glucose tolerance test in apoA-IV wild-type and knockout animals at 16 months of age.

As shown in FIG. 2, apoA-IV KO mice were glucose intolerant relative to the WT mice. Specifically, FIG. 2 shows that plasma glucose levels in WT mice were lower than plasma glucose levels in apoA-IV KO mice for two hours following intraperitoneal injection with glucose. While not being bound by the theory, the implication of these studies was that apoA-IV is necessary for normal glucose homeostasis (at least in males). Moreover, as shown in FIG. 3, apoA-IV KO mice demonstrated an increased glucose intolerance when tested at sixteen months of age. Specifically, FIG. 3 shows that plasma glucose levels in apoA-IV KO mice tested at sixteen months of age were higher than the plasma glucose levels in apoA-IV KO tested at three months of age. While not being bound by the theory, the implication of these studies was that glucose tolerance of apoA-IV KO mice worsens with age.

Experiment with Female Wild Type and ApoA-IV Knockout Mice

Figure 11:
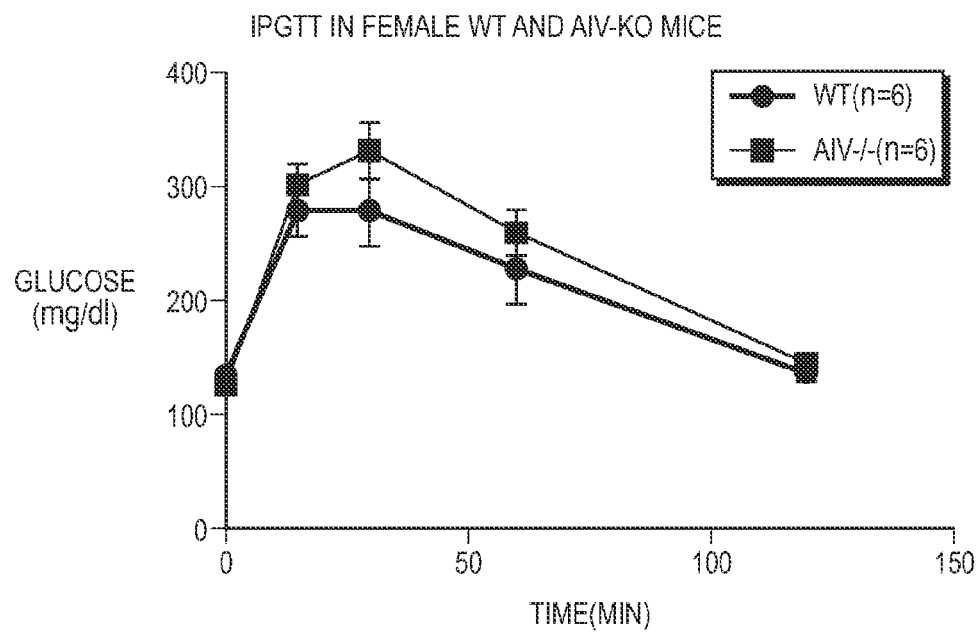
FIG. 11 is a graph of plasma glucose (mg/dL) in female apoA-IV knockout and wild-type mice with respect to time (min) during an intraperitoneal glucose tolerance test (IP-GTT).

Female ApoA-IV wildtype and knockout mice were subjected to the same intraperitoneal glucose tolerance test as was used for the male apoA-IV KO and WT mice, as described earlier in this Example 1. The results are shown in FIG. 11. Female apoA-IV$^{-/-}$ mice, when challenged intraperitoneally with glucose, have increased plasma glucose levels compared with female WT animals, but there is no statistical significant difference. On the other hand, the males have a significant difference between WT and KO animals.

Example 2: Restoration of Glucose Tolerance in ApoA-IV Knockout Mice

Experimental Protocol.

Upon demonstrating that apoA-IV KO mice are glucose intolerant, a series of extensive studies were performed to determine whether administration of apoA-IV to apoA-IV KO mice would restore glucose tolerance to a normal level. Specifically, a series of studies were performed to determine not only the amount of apoA-IV to be administered but also the optimal time in which to administer apoA-IV prior to conducting glucose tolerance tests.

ApoA-IV male KO mice were injected intraperitoneally with doses of about 0.25, 0.5, 1, and 2 μg/g by weight of apoA-IV. ApoA-IV KO mice were also injected intraperitoneally with saline solution to serve as a control. Following injection with mouse apoA-IV or saline solution, glucose tolerance tests were conducted at three months of age as previously discussed. Specifically, glucose tolerance tests were conducted about two hours following injection with apoA-IV or saline solution. Experimental results indicated that the optimal time to restore glucose tolerance in apoA-IV KO mice was to administer apoA-IV about two hours prior to conducting glucose tolerance tests.

Experimental Results.

Figure 4:
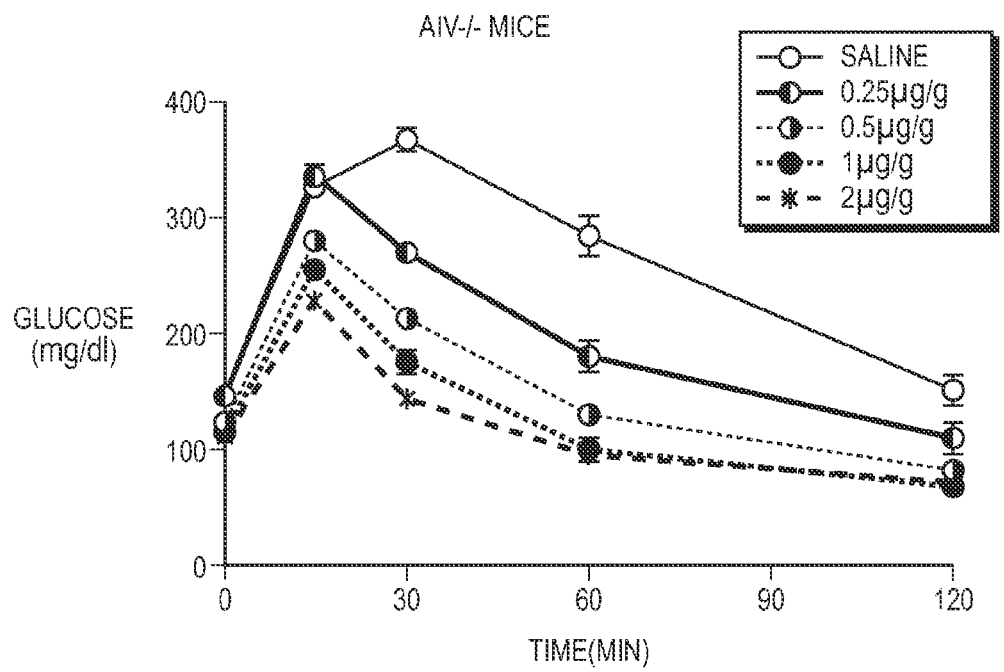
FIG. 4 is a graph of plasma glucose (mg/dL) with respect to time (min) in male apoA-IV knockout mice following the intraperitoneal administration of recombinant apoA-IV (µg/g) or saline solution for an intraperitoneal glucose tolerance test.

As shown in FIG. 4, the administration of apoA-IV to apoA-IV KO mice restored glucose tolerance to a normal level. Specifically, FIG. 4 shows that plasma glucose levels in apoA-IV KO mice injected with apoA-IV were lower than plasma glucose levels in apoA-IV KO mice injected with saline solution. Moreover, as shown in FIG. 4, plasma glucose levels in apoA-IV KO mice injected with apoA-IV were the lowest in the apoA-IV KO mice injected with the highest dosage of apoA-IV; similarly, plasma glucose levels in apoA-IV KO mice injected with apoA-IV were the highest in the apoA-IV KO mice injected with the lowest dosage of apoA-IV. Accordingly, it was discovered that the degree of improvement of glucose tolerance was dependent on the dose of apoA-IV administered, with higher doses resulting in improved glucose tolerance.

Example 3: Specificity of ApoA-IV in Restoring Glucose Tolerance in ApoA-IV Knockout Mice Experimental Protocol.

In order to assess the specificity of apoA-IV, we administered apolipoprotein AI (hereinafter "apoA-I") to apoA-IV KO mice. ApoA-I is a protein made by the small intestinal epithelial cells which also produce apoA-IV. ApoA-I shares many of the functions of apoA-IV. ApoA-IV KO mice were injected intraperitoneally with a dose of 1 µg/g by weight of apoA-I. ApoA-IV KO mice were also injected intraperitoneally with saline solution to serve as a control. Following injection with apoA-I or saline solution, glucose tolerance tests were conducted at three months of age as previously discussed. Specifically, glucose tolerance tests were conducted about two hours following injection with apoA-I or saline solution.

Experimental Results.

Figure 5:
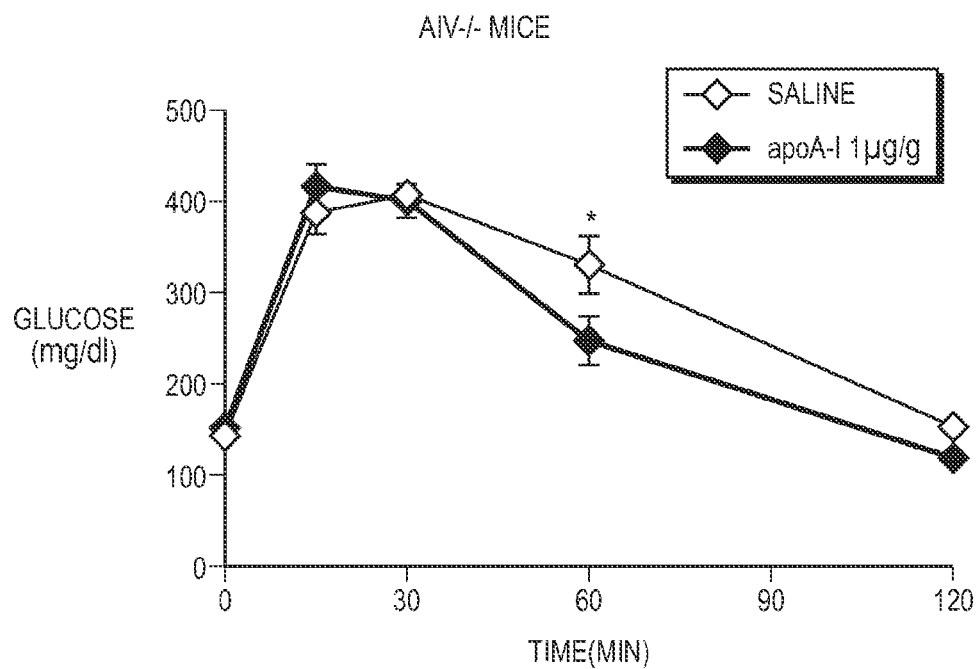
FIG. 5 is a graph of plasma glucose (mg/dL) with respect to time (min) in apoA-IV knockout mice following the intraperitoneal administration of recombinant apoA-I or saline solution for an intraperitoneal glucose tolerance test.

As shown in FIG. 5, the administration of apoA-I to apoA-IV KO mice failed to restore or improve glucose tolerance.

Example 4: Mechanism of Restoration of Glucose Tolerance in ApoA-IV Knockout Mice Experimental Protocol. In order to assess the mechanism by which ApoA-IV improves glucose tolerance in apoA-IV KO mice, we measured glucose-induced insulin secretion in apoA-IV KO mice. More specifically, we measured glucose-induced insulin secretion during glucose tolerance tests at three months of age as previously discussed. In this study, apoA-IV KO mice were injected intraperitoneally with a dose of about 1 µg/g by weight of mouse apoA-IV two hours prior to conducting the glucose tolerance tests. ApoA-IV KO mice were injected with saline solution about two hours prior to conducting glucose tolerance tests to serve as a control.

Experimental Results.

Figure 6:
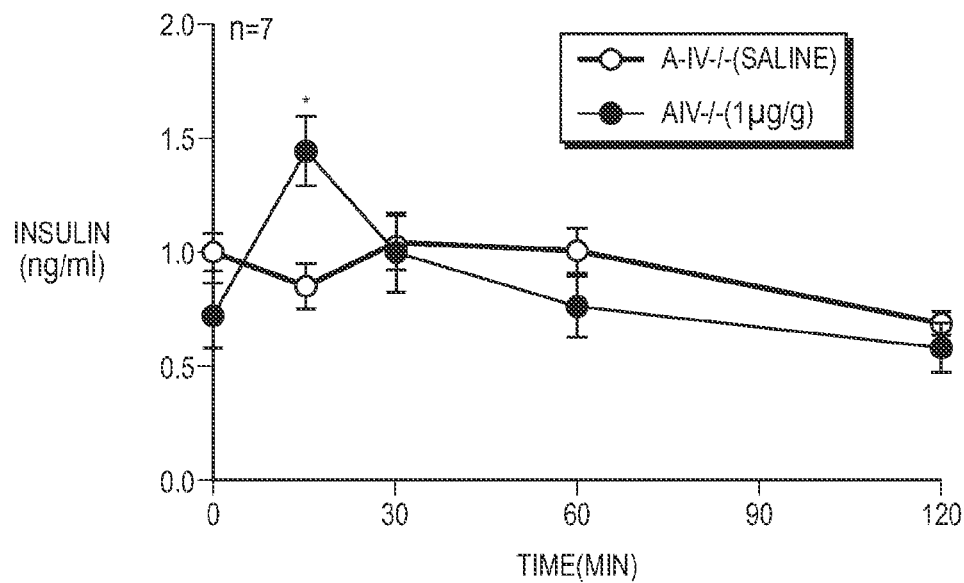
FIG. 6 is a graph of insulin secretion (ng/mL) with respect to time (min) in apoA-IV knockout mice following the intraperitoneal administration of recombinant apoA-I or saline solution.

As shown in FIG. 6, phase I insulin secretion was absent in apoA-IV KO mice injected with saline solution. However, as shown in FIG. 6, phase I insulin secretion was restored in apoA-IV KO mice when apoA-IV was injected intraperitoneally two hours prior to performing the glucose tolerance tests.

Example 5: Efficacy of ApoA-IV in ApoA-IV Knockout and Wild-Type Mice on High Fat Diets Experimental Protocol.

ApoA-IV KO and WT mice were chronically fed a high-fat semi-purified, nutritionally complete experimental diets (AIN-93M) purchased from Dyets (Bethlehem, Pa.) for 10 weeks. The high-fat diets contain about 20 g of fat (i.e. about 19 g of butter fat and 1 g of soybean oil to provide essential fatty acids) per 100 g of diet. The apoA-IV KO and WT mice were housed in individual tub cages with corncob bedding in a temperature-(about 22±1° C.) and light-(about 12 h light/12 dark) controlled vivarium. Glucose tolerance tests were performed at three months of age as previously discussed. Prior to performing the glucose tolerance tests, apoA-IV KO mice and WT mice were fasted for five hours. In the glucose tolerance tests, the apoA-IV KO mice and WT mice were injected intraperitoneally with a dose of about 2 mg/g body weight of glucose.

Experimental Results.

Figure 7:
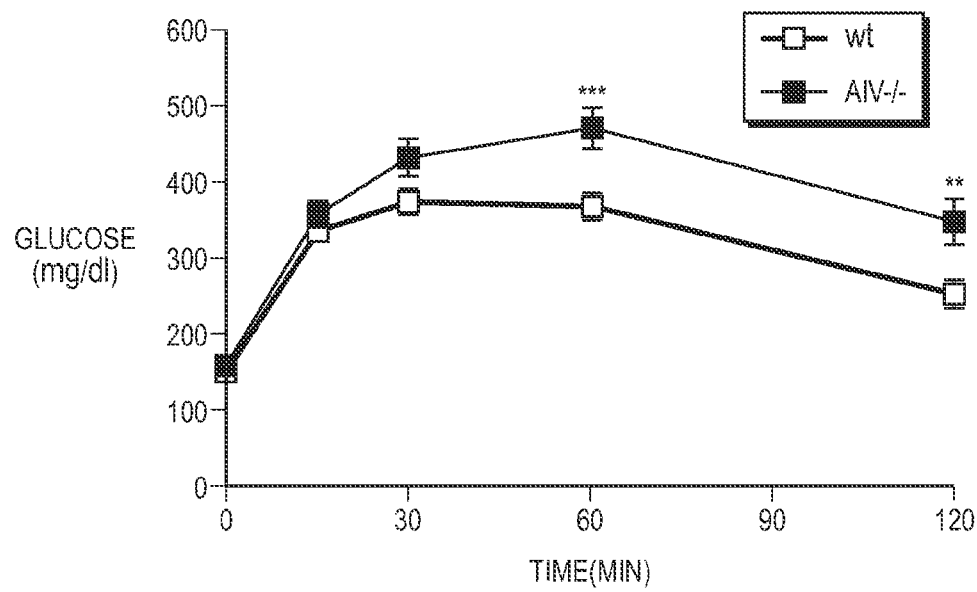
FIG. 7 is graph of plasma glucose (mg/mL) with respect to time (min) in apoA-IV knockout and wild-type mice on a chronically high-fat diet for an intraperitoneal glucose tolerance test.

As shown in FIG. 7, apoA-IV KO mice displayed greater glucose intolerance relative to the WT mice. Specifically, FIG. 7 shows that plasma glucose levels in WT mice were lower than plasma glucose levels in apoA-IV KO mice for two hours following intraperitoneal injection with glucose.

Example 6: Restoration of Glucose Tolerance in ApoA-IV Knockout and Wild-Type Mice on High Fat Diets Experimental Protocol.

A series of studies were performed related to the administration of apoA-IV to apoA-IV KO and WT mice on high-fat diets for 14 weeks at three months of age (20% by weight of fat, 19% of butter fat and 1% of safflower oil). Specifically, apoA-IV KO and WT mice were injected intraperitoneally with a dose of about 1 µg/g body weight of mouse apoA-IV. ApoA-IV KO and WT mice were also injected intraperitoneally with saline solution to serve as a control. Following injection with apoA-IV or saline solution, glucose tolerance tests were conducted. Specifically, glucose tolerance tests were conducted two hours following injection with apoA-IV or saline solution.

Experimental Results.

Figure 8:
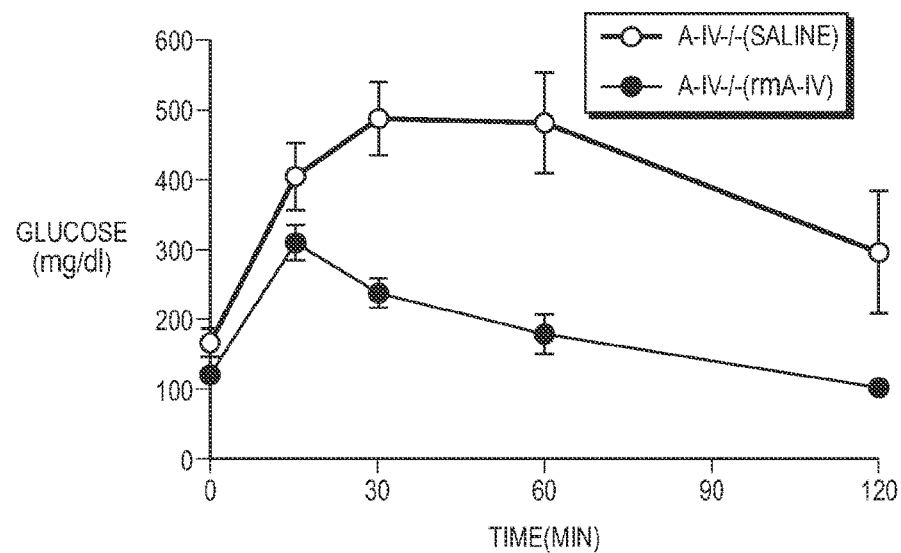
FIG. 8 is a graph of plasma glucose (mg/mL) with respect to time (min) in apoA-IV knockout mice on a chronically high-fat diet following the intraperitoneal administration of recombinant mouse apoA-IV (1 µg/g) or saline solution for an intraperitoneal glucose tolerance test.

As shown in FIG. 8, the administration of apoA-IV in apoA-IV KO mice significantly improved glucose tolerance. Specifically, FIG. 8 shows that plasma glucose levels in apoA-IV KO mice injected with apoA-IV were lower than plasma glucose levels in apoA-IV KO mice injected with saline solution. [the previous sentence is redundant since the next sentence describes the same thing. Although the data is not included herein, it was also discovered that the administration of apoA-IV in WT mice fed chronically a high fat diet also significantly improved glucose tolerance.

Example 7: Restoration of Glucose Tolerance in Mice with Type 2 Diabetes

Experimental Protocol.

In order to confirm that apoA-IV is effective in promoting glucose tolerance in animals with type 2 diabetes, heterozygous KK Cg-A/J (hereinafter "Cg-A/J") mice were obtained from Jackson Laboratories (Bar Harbor, Me.). Cg-A/J mice develop hyperglycemia, hyperinsulinemia, obesity, and glucose intolerance by eight weeks of age. The main cause of diabetes in these mice is insulin resistance produced by the polygenic interactions with the $A^y$ mutation, which encodes the agouti related protein and antagonist of the melanocortin-IV receptor. The Cg-A/J mice were fed chow diet. Additionally, there was a marked increase in blood glucose from ten to fourteen weeks of feeding the chow diet.

At fourteen weeks of age, the Cg-A/J mice were administered either mouse apoA-IV (about 1 µg/g body weight) or saline solution (to serve as a control) via intraperitoneal injection. Plasma glucose was then determined at about 0, 0.5, 1, 2, 3, 4, 5, 7, 11, and 24 hours.

Experimental Results.

Figure 9:
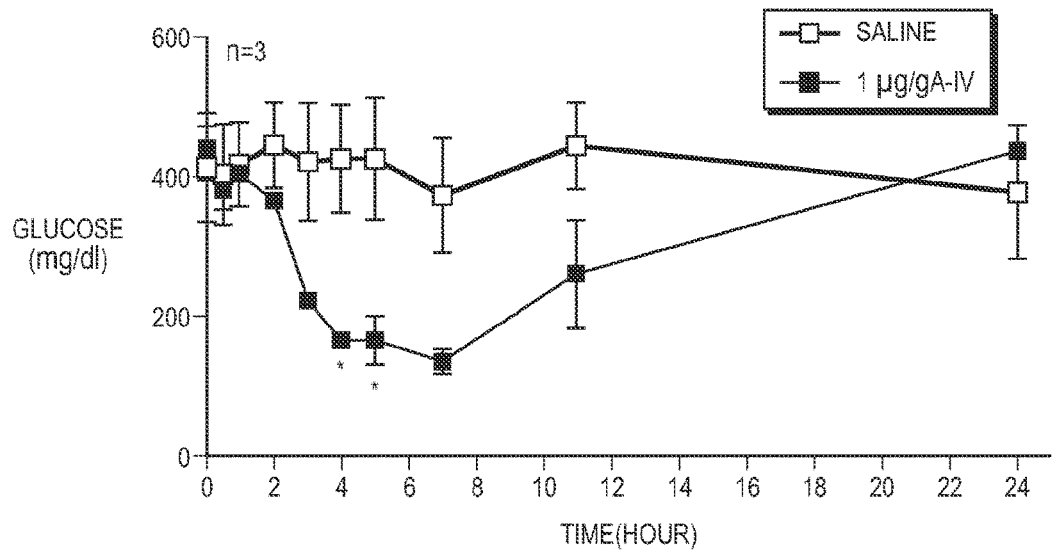
FIG. 9 is a graph of plasma glucose (mg/dL) with respect to time (h) in diabetic mice following the intraperitoneal administration of recombinant mouse apoA-IV (1 µg/g) or saline solution for an intraperitoneal glucose tolerance test.

As shown in FIG. 9, apoA-IV has a marked effect in lowering the blood sugar level of the Cg-A/J mice relative to the saline control. While the Cg-A/J mice injected with saline solution maintained a steady plasma glucose level throughout the 24 hour period of study, the Cg-A/J mice injected with apoA-IV experienced a decrease in plasma glucose for over 10 hours, and, during most of this period, the plasma glucose level was comparable to the C57BL/6J animals we have been studying. From this study, we conclude that the administration of apoA-IV is effective in lowering the plasma glucose in Cg-A/J mice.

Example 8: Level of Serum Amyloid P Component in ApoA-IV KO, ApoA-I KO, and WT Mice Experimental Protocol.

A series of studies were performed in related to determining the level of serum amyloid A protein component (hereinafter "SAP") in apoA-IV KO, apoA-I KO, and WT mice on atherogenic diets. The apoA-IV KO, apoA-I KO, and WT mice were obtained from the University of Cincinnati. SAP is a serum form of amyloid P component (hereinafter "AP"), a 25 kDa pentameric protein first identified as the pentagonal constituent of in vivo pathological deposits called amyloid. SAP behaves like C-reactive protein in humans. Specifically, the level of plasma SAP in apoA-IV KO, apoA-I KO, and WT mice was determined in apoA-IV KO, apoA-I KO, and WT mice after 12 weeks on an atherogenic diet. The level of plasma SAP was determined via Western blot analysis.

Experimental Results.

Figure 10:
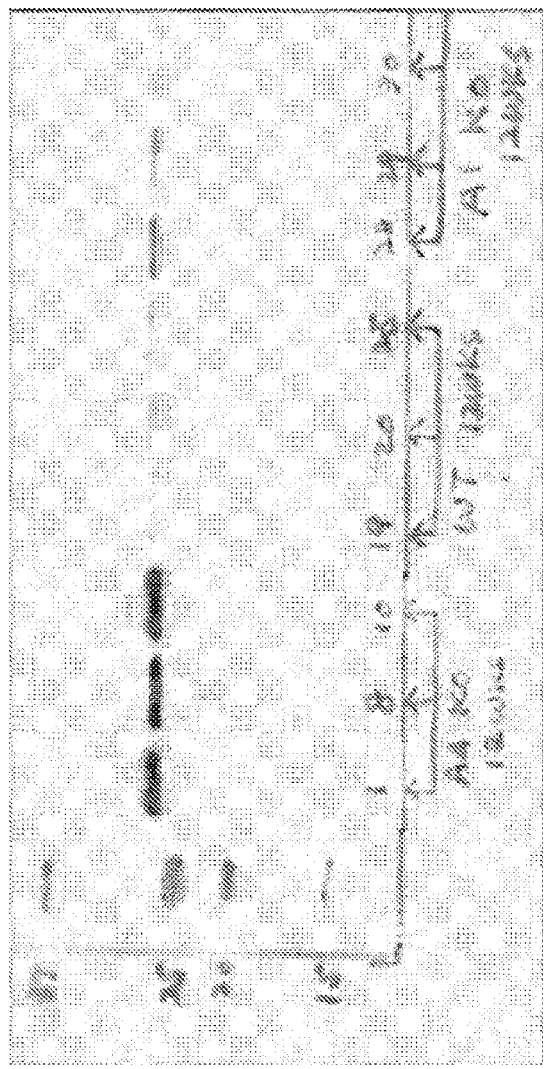
FIG. 10 depicts the results of a Western blot analysis of the level of serum amyloid A protein component in apoA-IV knockout mice, wild-type mice, and apoA-I knockout mice.

As shown in FIG. 10, the level of SAP in apoA-IV KO mice (corresponding to mouse numbers 1, 8, and 10) increased relative to the level of SAP in apoA-I KO mice (corresponding to mouse numbers 28, 29, and 30) and WT mice (corresponding to mouse numbers 19, 20, and 25).

For the purposes of describing and defining the present disclosure it is noted that the terms "about" and "substantially" are utilized herein to represent the inherent degree of uncertainty that may be attributed to any quantitative comparison, value, measurement, or other representation. The terms "about" and "substantially" are also utilized herein to represent the degree by which a quantitative representation may vary from a stated reference without resulting in a change in the basic function of the subject matter at issue.

The above description and drawings are only to be considered illustrative of exemplary embodiments, which achieve the features and advantages of the present disclosure. Modification and substitutions the features and steps described can be made without departing from the intent and scope of the present disclosure. Accordingly, the disclosure is not to be considered as being limited by the foregoing description and drawings, but is only limited by the scope of the appended claims.

Example 9: Human ApoA-IV Lowers Blood Glucose Levels in Wild-Type Mice Undergoing Intraperitoneal Glucose Tolerance Testing Experimental Protocol.

Studies were performed to determine whether administration of human apoA-IV to wild type mice would affect blood glucose levels in mice undergoing glucose tolerance testing.

Three month old wild type mice were injected intraperitoneally with doses of about 1 µg/g by weight of human apoA-IV. As a control, another group of wild type mice was injected intraperitoneally with saline solution. Following injection with human apoA-IV or saline solution, glucose tolerance tests were conducted. Specifically, glucose tolerance tests were conducted about two hours following injection with apoA-IV or saline solution and after five hours of fasting. Tail blood was collected and measure by glucometer.

Experimental Results.

Figure 12:
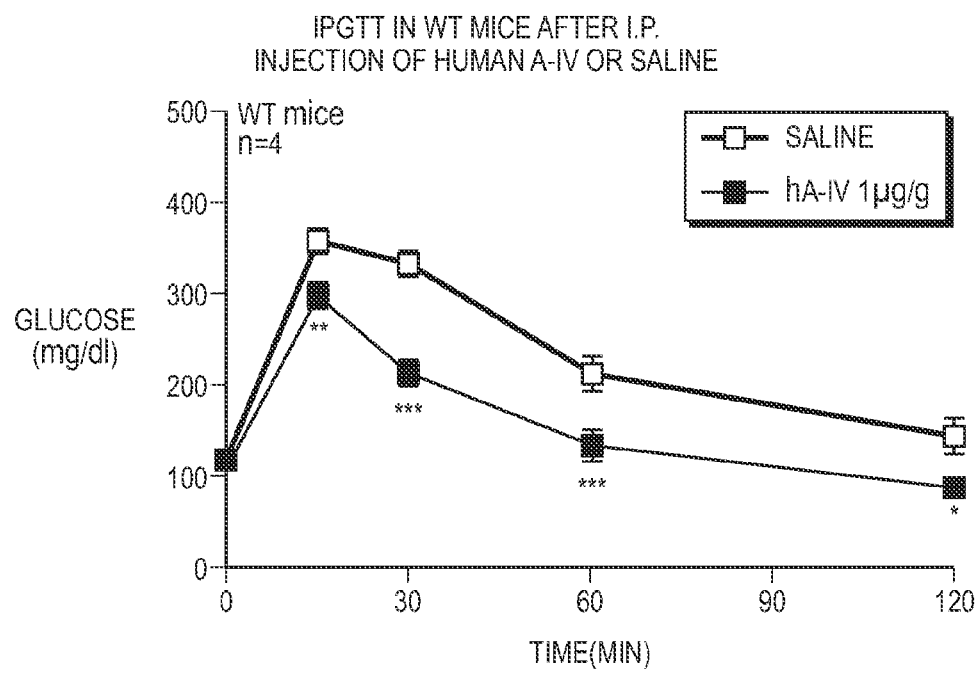
FIG. 12. is a graph of plasma glucose (mg/dL) with respect to time (min) in wild type mice following the intraperitoneal administration of 1.0 µg/g human apoA-IV or saline solution during an intraperitoneal glucose tolerance test.

As shown in FIG. 12, human apoA-IV was effective in lowering blood glucose in wild type mice undergoing glucose tolerance testing.

Example 10: Effect of Mouse ApoA-IV in Wild-Type Female Mice Undergoing Intraperitoneal Glucose Tolerance Testing Experimental Protocol.

Studies were performed to determine whether administration of mouse apoA-IV to female wild type mice would affect blood glucose levels in mice undergoing glucose tolerance testing.

Three month old female wild type mice were injected intraperitoneally with doses of about 1 µg/g by weight of mouse apoA-IV. As a control, another group of female wild type mice were injected intraperitoneally with saline solution. Following injection with human apoA-IV or saline solution, glucose tolerance tests were conducted. Specifically, glucose tolerance tests were conducted about two hours following injection with apoA-IV or saline solution and after five hours of fasting. Tail blood was collected and measure by glucometer.

Experimental Results.

Figure 13:
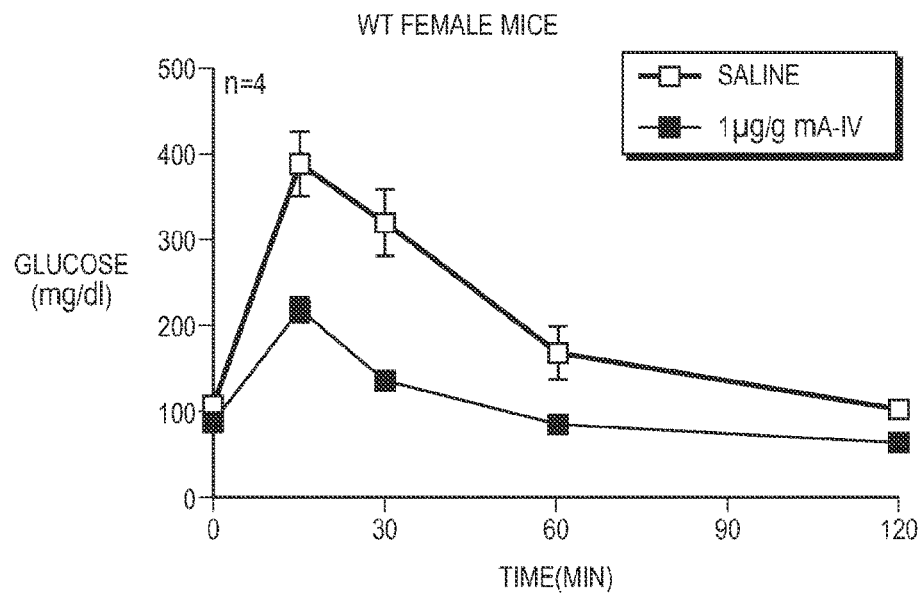
FIG. 13 is a graph of plasma glucose (mg/dL) with respect to time (min) in female wild type mice following the intraperitoneal administration of 1.0 µg/g recombinant mouse apoA-IV or saline solution during an intraperitoneal glucose tolerance test.

As shown in FIG. 13, mouse apoA-IV was effective in lowering blood glucose in wild type female mice undergoing glucose tolerance testing.

Example 11: Human ApoA-IV Stimulates Insulin Release in Human Islets

High purity human islets were provided by University of Virginia, Axon Cells. Islets were cultured in RPMI 1640, containing 10% FBS and 11 mM glucose at 37° C. in a humidified atmosphere of 95% air and 5% $CO_2$ for 48 hours. Four Groups of 50 IEQ islets were then pre-incubated at 37° C. for 1 h in regular KRB (129 mM NaCl, 4.8 mM KCl, 2.5 mM $CaCl_2$, 1.2 mM $MgSO_4$, 1.2 mM $KH_2PO_4$, 5 mM $NaHCO_3$, 10 mM HEPES and 0.2% BSA) containing 3.0 mM glucose. Islets in the first two groups were then incubated in regular KRB containing 3.0 mM glucose for an hour in the presence or absence of 10 µg/ml human A-IV and were further incubated with 20 mM glucose for an additional hour in the presence or absence of 10 µg/ml human A-IV. Islets in the last two groups were incubated in 30 mM KCl KRB (103.8 mM NaCl, 30 mM KCl, 2.5 mM $CaCl_2$, 1.2 mM $MgSO_4$, 1.2 mM $KH_2PO_4$, 5 mM $NaHCO_3$, 10 mM HEPES and 0.2% BSA) plus 250 µmol/l diazoxide containing 3.0 mM glucose for an hour in the presence or absence of 10 µg/ml human A-IV and were further incubated with 20 mM glucose for an additional hour in the presence or absence of 10 µg/ml human A-IV. Media were collected at the end of each one-hour incubation. Insulin levels were measured by ELISA kit (Millipore).

Figure 14:
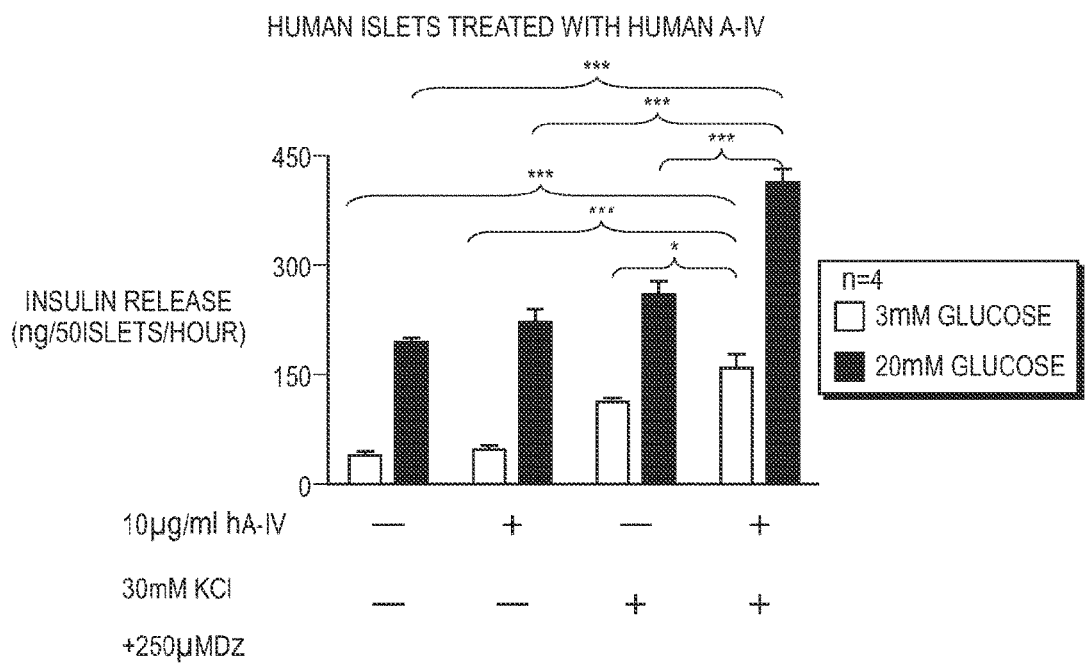
FIG. 14 is a bar graph showing the effect of 10 µg/g human apoA-IV on human islets depolarized by 30 mM KCl and 250 µM diazoxide in the presence of 3 mM or 20 mM glucose.

As can be seen from FIG. 14, when the human islets were maximally depolarized by 30 mM KCl plus 250 µM diazoxide, 10 µg/ml hA-IV showed a significant stimulatory effect on insulin secretion.

Example 12: Preparation of Non-Glycosylated ApoA-IV

Human and mouse apoA-IV cDNA was contained in a pSP65 maintenance vector, and an Afl III restriction site was engineered immediately 5' of the coding sequence for the mature apoA-IV protein. The gene was excised from the maintenance vector and ligated into the pET30 expression vector. The construct was transfected into *E. Coli* BL-21 (DE3) cells and grown in Luria-Bertani cultures supplemented with kanamycin (30 μg/ml) at 37° C. After induction of apoA-IV protein synthesis in the cells, the cells were harvested and sonicated. ApoA-IV protein from the lysate was purified by His-bind affinity column chromatography and dialysis. The resultant apoA-IV protein was diluted to a final concentration of 1.0 mg/ml in saline.

Example 13: Absence of N- and O-Glycosylation in Human ApoA-IV

Figure 25A:
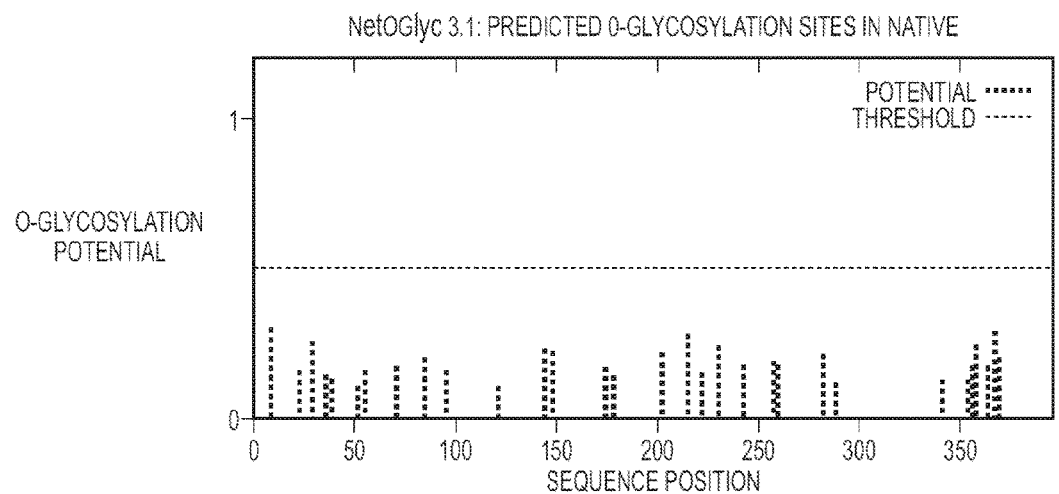
FIGS. 25A and B shows O-glycosylation prediction results for the human wild type apoA-IV (FIG. 25A) and variant P393H (FIG. 25B).
Figure 25B:
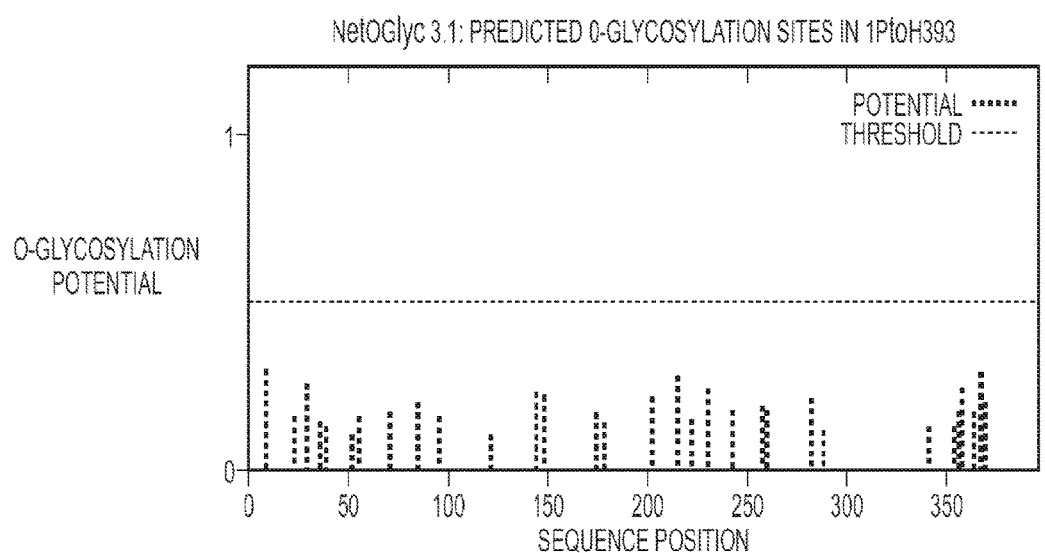

Using the NetNGlyc 1.0 server, human apoA-IV and 45 missense variants were analyzed in silico. Details regarding the missense variants are provided in Table 1. The 0- and N-linked glycosylation analyses are exemplified in FIGS. 24 and 25 by the native apoA-IV and an exemplary variant, i.e., P393H. The results show that human apoA-IV and the missense variants do not possess any N-linked or N-linked glycosylation sites. Notably, the variants described in Table 1 (represented by the amino acid sequences described in SEQ ID NOs: 20-64; SEQ ID NO 65 represents ApoAIV with the signal sequence) had glycosylation profiles identical to those presented in FIGS. 24 and 25. These results are unexpected in view of common knowledge in the art, e.g., Weinberg, et al., J Lipid Res. 1983, 24(1):52-9, that apoA-IV is glycosylated by mannose, galactose, N-acetyl glucosamine, and sialic acid.

TABLE 1

ApoAIV variants (APOA4 gene (mRNA accession no. NM_000482.3))

| SNP Pos | rs ID | Alleles | EA Allele # | AA Allele # | All Allele # | Avg. Sample Read Depth | GVS Function | Amino Acid | Protein Pos. | cDNA Pos. |
|---|---|---|---|---|---|---|---|---|---|---|
| 11:11669 1554 | unknown | A/G | A = 6/ G = 7014 | A = 0/ G = 3738 | A = 6/ G = 10752 | 51 | utr-3 | none | NA | NA |
| 11:11669 1557 | unknown | A/G | A = 0/ G = 7020 | A = 2/ G = 3736 | A = 2/ G = 10756 | 51 | utr-3 | none | NA | NA |
| 11:11669 1562 | unknown | A/G | A = 1/ G = 7019 | A = 0/ G = 3738 | A = 1/ G = 10757 | 51 | utr-3 | none | NA | NA |
| 11:11669 1596 | unknown | T/G | T = 0/ G = 7020 | T = 1/ G = 3737 | T = 1/ G = 10757 | 46 | missense mutation | HIS, PRO | 393/397 | 1178 |
| 11:11669 1610 | unknown | T/C | T = 2/ C = 7016 | T = 0/ C = 3738 | T = 2/ C = 10754 | 46 | silent mutation | none | 388/397 | 1164 |
| 11:11669 1621 | rs140878274 | T/G | T = 0/ G = 7016 | T = 13/ G = 3725 | T = 13/ G = 10741 | 47 | missense mutation | LYS, GLN | 385/397 | 1153 |
| 11:11669 1628 | rs143392864 | T/C | T = 1/ C = 7015 | T = 54/ C = 3684 | T = 55/ C = 10699 | 48 | silent mutation | none | 382/397 | 1146 |
| 11:11669 1633 | unknown | T/G | T = 0/ G = 7016 | T = 1/ G = 3737 | T = 1/ G = 10753 | 49 | missense mutation | LYS, GLN | 381/397 | 1141 |
| 11:11669 1634 | rs5110 | A/C | A = 559/ C = 6457 | A = 66/ C = 3672 | A = 625/ C = 10129 | 49 | missense mutation | HIS, GLN | 380/397 | 1140 |
| 11:11669 1644 | unknown | G/T | G = 0/ T = 7016 | G = 1/ T = 3737 | G = 1/ T = 10753 | 52 | missense mutation | PRO, GLN | 377/397 | 1130 |
| 11:11669 1645 | unknown | A/G | A = 1/ G = 7015 | A = 0/ G = 3738 | A = 1/ G = 10753 | 52 | stop-gained | stop, GLN | 377/397 | 1129 |
| 11:11669 1655 | unknown | T/C | T = 0/ C = 7016 | T = 1/ C = 3737 | T = 1/ C = 10753 | 55 | silent mutation | none | 373/397 | 1119 |
| 11:11669 1675 | rs675 | A/T | A = 1403/ T = 5611 | A = 416/ T = 3322 | A = 1819/ T = 8933 | 66 | missense mutation | SER, THR | 367/397 | 1099 |
| 11:11669 1703 | unknown | A/G | A = 1/ G = 7011 | A = 0/ G = 3738 | A = 1/ G = 10749 | 78 | silent mutation | none | 357/397 | 1071 |
| 11:11669 1717 | rs146353487 | C/A | C = 3/ A = 7009 | C = 96/ A = 3642 | C = 99/ A = 10651 | 83 | missense mutation | ALA, SER | 353/397 | 1057 |
| 11:11669 1720 | rs747577451 | A/T | A = 2/ T = 7010 | A = 1/ T = 3737 | A = 3/ T = 10747 | 84 | missense mutation | TYR, ASN | 352/397 | 1054 |
| 11:11669 1754 | unknown | T/C | T = 0/ C = 7012 | T = 1/ C = 3737 | T = 1/ C = 10749 | 78 | silent mutation | none | 340/397 | 1020 |
| 11:11669 1766 | rs5109 | A/C | A = 1/ C = 7011 | A = 284/ C = 3454 | A = 285/ C = 10465 | 76 | silent mutation | none | 336/397 | 1008 |
| 11:11669 1768 | rs145761354 | T/C | T = 8/ C = 7004 | T = 1/ C = 3737 | T = 9/ C = 10741 | 76 | missense mutation | MET, VAL | 336/397 | 1006 |
| 11:11669 1771 | rs148203811 | G/C | G = 1/ C = 7011 | G = 0/ C = 3738 | G = 1/ C = 10749 | 75 | missense mutation | HIS, ASP | 335/397 | 1003 |
| 11:11669 1843 | unknown | T/C | T = 1/ C = 7011 | T = 0/ C = 3738 | T = 1/ C = 10749 | 60 | missense mutation | ARG, GLY | 311/397 | 931 |
| 11:11669 1844 | unknown | A/G | A = 2/ G = 7010 | A = 0/ G = 3738 | A = 2/ G = 10748 | 59 | silent mutation | none | 310/397 | 930 |
| 11:11669 1855 | rs5108 | G/C | G = 0/ C = 7012 | G = 4/ C = 3734 | G = 4/ C = 10746 | 53 | missense mutation | LEU, VAL | 307/397 | 919 |
| 11:11669 1861 | rs150264487 | A/G | A = 1/ G = 7011 | A = 0/ G = 3738 | A = 1/ G = 10749 | 49 | missense mutation | CYS, ARG | 305/397 | 913 |
| 11:11669 1863 | rs150624574 | T/C | T = 1/ C = 7011 | T = 0/ C = 3738 | T = 1/ C = 10749 | 48 | missense mutation | GLN, ARG | 304/397 | 911 |
| 11:11669 1886 | rs5107 | T/C | T = 0/ C = 7008 | T = 11/ C = 3727 | T = 11/ C = 10735 | 41 | silent mutation | none | 296/397 | 888 |
| 11:11669 1902 | unknown | C/T | C = 2/ T = 6998 | C = 0/ T = 3736 | C = 2/ T = 10734 | 40 | missense mutation | GLY, GLU | 291/397 | 872 |
| 11:11669 1928 | rs5106 | A/G | A = 2/ G = 7004 | A = 148/ G = 3586 | A = 150/ G = 10590 | 37 | silent mutation | none | 282/397 | 846 |

TABLE 1-continued

ApoAIV variants (APOA4 gene (mRNA accession no. NM_000482.3))

| SNP Pos | rs ID | Alleles | EA Allele # | AA Allele # | All Allele # | Avg. Sample Read Depth | GVS Function | Amino Acid | Protein Pos. | cDNA Pos. |
|---|---|---|---|---|---|---|---|---|---|---|
| 11:116691937 | unknown | G/C | G = 1/ C = 7011 | G = 1/ C = 3737 | G = 2/ C = 10748 | 36 | missense mutation | SER, ARG | 279/397 | 837 |
| 11:116691953 | unknown | G/A | G = 0/ A = 7010 | G = 1/ A = 3733 | G = 1/ A = 10743 | 36 | missense mutation | ALA, VAL | 274/397 | 821 |
| 11:116691954 | unknown | T/C | T = 1/ C = 7011 | T = 0/ C = 3734 | T = 1/ C = 10745 | 36 | missense mutation | MET, VAL | 274/397 | 820 |
| 11:116691955 | rs146365840 | A/G | A = 1/ G = 7009 | A = 2/ G = 3736 | A = 3/ G = 10745 | 36 | silent mutation | none | 273/397 | 819 |
| 11:116691983 | rs2238008 | T/C | T = 1/ C = 7009 | T = 6/ C = 3732 | T = 7/ C = 10741 | 46 | missense mutation | GLN, ARG | 264/397 | 791 |
| 11:116691994 | rs5105 | A/G | A = 0/ G = 7012 | A = 67/ G = 3671 | A = 67/ G = 10683 | 50 | silent mutation | none | 260/397 | 780 |
| 11:116691996 | rs144225488 | T/C | T = 1/ C = 7011 | T = 0/ C = 3738 | T = 1/ C = 10749 | 50 | missense mutation | THR, ALA | 260/397 | 778 |
| 11:116692026 | rs121909576 | T/C | T = 2/ C = 7010 | T = 0/ C = 3738 | T = 2/ C = 10748 | 70 | missense mutation | LYS, GLU | 250/397 | 748 |
| 11:116692070 | rs148724513 | C/T | C = 0/ T = 7012 | C = 2/ T = 3736 | C = 2/ T = 10748 | 116 | missense mutation | SER, ASN | 235/397 | 704 |
| 11:116692083 | rs142283748 | T/G | T = 0/ G = 7012 | T = 1/ G = 3737 | T = 1/ G = 10749 | 127 | missense mutation | LYS, GLN | 231/397 | 691 |
| 11:116692116 | unknown | A/G | A = 0/ G = 7012 | A = 1/ G = 3737 | A = 1/ G = 10749 | 160 | missense mutation | CYS, ARG | 220/397 | 658 |
| 11:116692120 | rs151212572 | T/C | T = 0/ C = 7012 | T = 1/ C = 3737 | T = 1/ C = 10749 | 169 | silent mutation | none | 218/397 | 654 |
| 11:116692132 | unknown | G/C | G = 0/ C = 7012 | G = 1/ C = 3737 | G = 1/ C = 10749 | 189 | missense mutation | HIS, GLN | 214/397 | 642 |
| 11:116692153 | rs139204483 | C/T | C = 0/ T = 7014 | C = 1/ T = 3737 | C = 1/ T = 10751 | 227 | silent mutation | none | 207/397 | 621 |
| 11:116692155 | rs145184607 | T/C | T = 1/ C = 7015 | T = 0/ C = 3738 | T = 1/ C = 10753 | 230 | missense mutation | LYS, GLU | 207/397 | 619 |
| 11:116692169 | rs147626624 | A/G | A = 1/ G = 7019 | A = 1/ G = 3737 | A = 2/ G = 10756 | 245 | missense mutation | MET, THR | 202/397 | 605 |
| 11:116692176 | rs142050734 | A/G | A = 1/ G = 7019 | A = 0/ G = 3738 | A = 1/ G = 10757 | 251 | missense mutation | CYS, ARG | 200/397 | 598 |
| 11:116692195 | unknown | A/G | A = 0/ G = 7020 | A = 1/ G = 3737 | A = 1/ G = 10757 | 239 | silent mutation | none | 193/397 | 579 |
| 11:116692203 | rs145898188 | T/C | T = 1/ C = 7019 | T = 0/ C = 3738 | T = 1/ C = 10757 | 228 | missense mutation | ASN, ASP | 191/397 | 571 |
| 11:116692204 | rs145525856 | T/G | T = 0/ G = 7020 | T = 9/ G = 3729 | T = 9/ G = 10749 | 225 | silent mutation | none | 190/397 | 570 |
| 11:116692224 | rs148815297 | T/C | T = 0/ C = 7020 | T = 1/ C = 3737 | T = 1/ C = 10757 | 185 | missense mutation | ASN, ASP | 184/397 | 550 |
| 11:116692232 | unknown | A/G | A = 1/ G = 7019 | A = 0/ G = 3738 | A = 1/ G = 10757 | 166 | missense mutation | LEU, PRO | 181/397 | 542 |
| 11:116692240 | unknown | T/C | T = 1/ C = 7019 | T = 0/ C = 3738 | T = 1/ C = 10757 | 150 | silent mutation | none | 178/397 | 534 |
| 11:116692258 | rs143451944 | C/G | C = 1/ G = 7019 | C = 0/ G = 3738 | C = 1/ G = 10757 | 112 | silent mutation | none | 172/397 | 516 |
| 11:116692260 | rs148364897 | T/C | T = 1/ C = 7019 | T = 0/ C = 3738 | T = 1/ C = 10757 | 107 | missense mutation | THR, ALA | 172/397 | 514 |
| 11:116692269 | rs142295954 | A/G | A = 0/ G = 7020 | A = 1/ G = 3737 | A = 1/ G = 10757 | 92 | missense mutation | TRP, ARG | 169/397 | 505 |
| 11:116692277 | rs145786821 | T/C | T = 1/ C = 7019 | T = 0/ C = 3738 | T = 1/ C = 10757 | 83 | missense mutation | LYS, ARG | 166/397 | 497 |
| 11:116692291 | unknown | C/T | C = 1/ T = 7017 | C = 0/ T = 3738 | C = 1/ T = 10755 | 65 | silent mutation | none | 161/397 | 483 |
| 11:116692293 | rs12721043 | A/C | A = 77/ C = 6941 | A = 9/ C = 3729 | A = 86/ C = 10670 | 62 | missense mutation | SER, ALA | 161/397 | 481 |
| 11:116692294 | unknown | A/G | A = 1/ G = 7017 | A = 0/ G = 3738 | A = 1/ G = 10755 | 61 | silent mutation | none | 160/397 | 480 |
| 11:116692312 | rs142835053 | T/C | T = 2/ C = 7016 | T = 0/ C = 3736 | T = 2/ C = 10752 | 46 | silent mutation | none | 154/397 | 462 |
| 11:116692314 | rs150633651 | A/G | A = 2/ G = 7016 | A = 0/ G = 3736 | A = 2/ G = 10752 | 45 | missense mutation | TRP, ARG | 154/397 | 460 |
| 11:116692324 | rs2234668 | A/G | A = 358/ G = 6660 | A = 37/ G = 3699 | A = 395/ G = 10359 | 40 | silent mutation | none | 150/397 | 450 |
| 11:116692331 | rs149339479 | A/G | A = 1/ G = 7015 | A = 0/ G = 3738 | A = 1/ G = 10753 | 39 | missense mutation | MET, THR | 148/397 | 443 |
| 11:116692334 | rs5104 | T/C | T = 6133/ C = 885 | T = 3299/ C = 439 | T = 9432/ C = 1324 | 38 | missense mutation | ASN, SER | 147/397 | 440 |
| 11:116692358 | rs139762470 | T/G | T = 0/ G = 7012 | T = 1/ G = 3737 | T = 1/ G = 10749 | 34 | missense mutation | GLU, ALA | 139/397 | 416 |
| 11:116692360 | rs145317065 | A/G | A = 0/ G = 7014 | A = 1/ G = 3737 | A = 1/ G = 10751 | 34 | silent mutation | none | 138/397 | 414 |
| 11:11669 | rs147610191 | T/G | T = 27/ | T = 0/ | T = 27/ | 34 | missense | LYS, | 127/397 | 381 |

TABLE 1-continued

ApoAIV variants (APOA4 gene (mRNA accession no. NM_000482.3))

| SNP Pos | rs ID | Alleles | EA Allele # | AA Allele # | All Allele # | Avg. Sample Read Depth | GVS Function | Amino Acid | Protein Pos. | cDNA Pos. |
|---|---|---|---|---|---|---|---|---|---|---|
| 2393 | | | G = 6971 | G = 3732 | G = 10703 | | mutation | ASN | | |
| 11:11669 2449 | rs6413456 | A/G | A = 1/ G = 7013 | A = 3/ G = 3731 | A = 4/ G = 10744 | 33 | silent mutation | none | 109/397 | 325 |
| 11:11669 2490 | rs142176503 | A/G | A = 0/ G = 7018 | A = 2/ G = 3736 | A = 2/ G = 10754 | 48 | missense mutation | LEU, SER | 95/397 | 284 |
| 11:11669 2506 | unknown | A/G | A = 0/ G = 7016 | A = 1/ G = 3737 | A = 1/ G = 10753 | 64 | missense mutation | CYS, ARG | 90/397 | 268 |
| 11:11669 2521 | rs151159258 | C/T | C = 0/ T = 7016 | C = 2/ T = 3736 | C = 2/ T = 10752 | 78 | missense mutation | ALA, THR | 85/397 | 253 |
| 11:11669 2543 | rs12721042 | A/C | A = 0/ C = 7018 | A = 1/ C = 3737 | A = 1/ C = 10755 | 101 | missense mutation | HIS, GLN | 77/397 | 231 |
| 11:11669 2552 | rs5103 | G/A | G = 251/ A = 6767 | G = 26/ A = 3712 | G = 277/ A = 10479 | 116 | silent mutation | none | 74/397 | 222 |
| 11:11669 2554 | rs5102 | T/C | T = 0/ C = 7018 | T = 5/ C = 3733 | T = 5/ C = 10751 | 120 | missense mutation | SER, GLY | 74/397 | 220 |
| 11:11669 2558 | rs5101 | A/G | A = 7/ G = 7013 | A = 1001/ G = 2737 | A = 1008/ G = 9750 | 129 | silent mutation | none | 72/397 | 216 |
| 11:11669 2594 | rs140708655 | T/G | T = 1/ G = 7019 | T = 0/ G = 3738 | T = 1/ G = 10757 | 199 | silent mutation | none | 60/397 | 180 |
| 11:11669 2600 | unknown | A/G | A = 1/ G = 7019 | A = 0/ G = 3738 | A = 1/ G = 10757 | 207 | intron | none | NA | NA |
| 11:11669 2625 | unknown | A/G | A = 1/ G = 7017 | A = 0/ G = 3738 | A = 1/ G = 10755 | 219 | intron | none | NA | NA |
| 11:11669 2634 | unknown | A/G | A = 0/ G = 7020 | A = 48/ G = 3690 | A = 48/ G = 10710 | 206 | intron | none | NA | NA |
| 11:11669 2645 | unknown | A/G | A = 0/ G = 7020 | A = 1/ G = 3737 | A = 1/ G = 10757 | 186 | intron | none | NA | NA |
| 11:11669 3353 | rs2239013 | T/C | T = 423/ C = 6597 | T = 175/ C = 3563 | T = 598/ C = 10160 | 257 | intron | none | NA | NA |
| 11:11669 3354 | rs5093 | A/G | A = 171/ G = 6849 | A = 91/ G = 3647 | A = 262/ G = 10496 | 261 | intron | none | NA | NA |
| 11:11669 3377 | unknown | C/G | C = 0/ G = 7020 | C = 1/ G = 3737 | C = 1/ G = 10757 | 281 | silent mutation | none | 58/397 | 174 |
| 11:11669 3398 | rs145911376 | C/T | C = 1/ T = 7019 | C = 0/ T = 3738 | C = 1/ T = 10757 | 261 | silent mutation | none | 51/397 | 153 |
| 11:11669 3416 | rs138490533 | A/G | A = 0/ G = 7020 | A = 2/ G = 3736 | A = 2/ G = 10756 | 229 | silent mutation | none | 45/397 | 135 |
| 11:11669 3464 | rs5092 | T/C | T = 5880/ C = 1140 | T = 3179/ C = 559 | T = 9059/ C = 1699 | 127 | silent mutation | none | 29/397 | 87 |
| 11:11669 3536 | unknown | A/G | A = 1/ G = 7019 | A = 0/ G = 3738 | A = 1/ G = 10757 | 127 | intron | none | NA | NA |
| 11:11669 3871 | rs12721041 | T/C | T = 125/ C = 6887 | T = 14/ C = 3724 | T = 139/ C = 10611 | 160 | missense mutation | MET, VAL | 13/397 | 37 |
| 11:11669 3875 | unknown | A/G | A = 1/ G = 7011 | A = 0/ G = 3738 | A = 1/ G = 10749 | 162 | silent mutation | none | 11/397 | 33 |
| 11:11669 3892 | rs148312574 | T/C | T = 5/ C = 7007 | T = 2/ C = 3736 | T = 7/ C = 10743 | 168 | missense mutation | MET, VAL | 6/397 | 16 |
| 11:11669 3893 | unknown | A/G | A = 1/ G = 7011 | A = 0/ G = 3738 | A = 1/ G = 10749 | 167 | silent mutation | none | 5/397 | 15 |

Note:
the filter status is pass for all entries of Table 1.

Example 14: Optimization of ApoA-IV for Bacterial Expression

To facilitate periplasmic expression of apoA-IV in *E. coli*, constructs were prepared using various signal peptides. These signal peptides (i.e. OmpA, PelB, and ENX) were each fused to the N-terminal of apoA-IV. The amino acid and nucleic acid sequences of each these signal sequences are provided as follows:

OmpA signal peptide (SEQ ID NO: 6)

M K K T A I A I A V A L A G F T A V A Q A (SEQ ID NO: 7)
ATG AAA AAG ACA GCT ATC GCG ATT GCA GTG GCA CTG
GCT GGT TTC GCT ACC GTA GCG CAG GCC

PelB signal peptide (SEQ ID NO: 8)

M K Y L L P T A A A G L L L L A A Q P A M A (SEQ ID NO: 9)
ATG AAA TAC CTG CTG CCG ACC GCT GCT GCT GGT CTG
CTG CTC CTC GCT GCC CAG CCG GCG ATG GCC

ENX signal peptide (SEQ ID NO: 10)

M F K F K K N F L V G L S A A L M S I S L F S A T A S A

-continued (SEQ ID NO: 11)
ATG TTT AAG TTT AAA AAG AAT TTC TTA GTT GGA TTA
TCG GCA GCT TTA ATG AGT ATT AGC TTG TTT TCG GCA
ACC GCC TCT GCA To improve protein yield in E. coli, the codon usage for apoA-IV was optimized. Optimization was performed using DNA2.0's algorithm (DNA2.0 Inc.) or other algorithms based on experimental data and the tRNA chargeability (amino acetylation). The apoA-IV coding sequence with optimized codons was then fused at the 5' end to the 3' end of the nucleotide sequence of a signal peptide. In addition, the codon-optimized sequence can be linked at its 3' end to a double stop codon. Constructs with the optimized codons and cloning sites are exemplified in FIGS. 20-23. The optimized DNA sequences are described in SEQ ID NOs: 13, 15, 17, and 19, with the resulting amino acid sequences set forth in SEQ ID NOs: 12, 14, 16, and 18, respectively. Notably, the optimized sequences (SEQ ID NOs: 12-19) may also be used in the methods and compositions of the invention.

The apoA-IV-constructs can then be synthesized by DNA2.0, Inc. and subcloned into a pJexpress vector (e.g., pJexpress401) using NdeI-XhoI restriction sites. These constructs can be transformed into BL21 E. coli strain (Novagen) (F⁻ OmpT hsdS$_B$(r$_B^-$m$_B^-$) gal dcm) and clones containing these constructs can be selected with Kanamycin. A pre-culture in 125 ml of YES medium containing Kanamycin (e.g., 50 μg/ml) can be inoculated starting from one isolated colony and incubated at 37° C. with agitation at 270 rpm for about 16 hours. A fresh culture in 500 ml of Kanamycin-containing YES medium can be inoculated with 10 mL of the pre-culture and incubated at 37° C. with agitation at 270 rpm until the OD$_{600}$ reaches 0.5 to 1.0 (optimum=0.6). The resultant culture will then be induced with IPTG (e.g., with a final concentration of 1 mM) and incubated at 37° C. for 1 hour, 2 hours, 4 hours, or 22 hours.

ApoA-IV protein can be isolated from periplasmic and cytoplasmic fractions of the culture prepared above. More specifically, the culture can be pelleted. The resultant culture pellet can be suspended in hypertonic TES buffer (sucrose 20%)/OD$_{600}$/mL and incubated for 5 min at room temperature before dilution in 4 volumes of purified water at 4° C. The diluted suspension can be further incubated for 10 min on ice and centrifuged for 5 min at 13,000 rpm. The resultant supernatant is periplasmic fraction (P) and the pellet is the cytoplasmic fraction. Expression of apoA-IV can be analyzed by SDS-PAGE or Western analysis. ApoA-IV in these fractions can then be purified by conventional and/or affinity chromatography, and formulated for delivery to humans for treatment of type II diabetes.

INCORPORATION BY REFERENCE

The contents of all references and patents cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 65

<210> SEQ ID NO 1
<211> LENGTH: 376
<212> TYPE: PRT
<213> ORGANISM: Homo sapiens

<400> SEQUENCE: 1

Glu Val Ser Ala Asp Gln Val Ala Thr Val Met Trp Asp Tyr Phe Ser
1               5                   10                  15

Gln Leu Ser Asn Asn Ala Lys Glu Ala Val Glu His Leu Gln Lys Ser
            20                  25                  30

Glu Leu Thr Gln Gln Leu Asn Ala Leu Phe Gln Asp Lys Leu Gly Glu
        35                  40                  45

Val Asn Thr Tyr Ala Gly Asp Leu Gln Lys Lys Leu Val Pro Phe Ala
    50                  55                  60

Thr Glu Leu His Glu Arg Leu Ala Lys Asp Ser Glu Lys Leu Lys Glu
65                  70                  75                  80

Glu Ile Gly Lys Glu Leu Glu Glu Leu Arg Ala Arg Leu Leu Pro His
                85                  90                  95

Ala Asn Glu Val Ser Gln Lys Ile Gly Asp Asn Leu Arg Glu Leu Gln
            100                 105                 110

Gln Arg Leu Glu Pro Tyr Ala Asp Gln Leu Arg Thr Gln Val Asn Thr
        115                 120                 125

Gln Ala Glu Gln Leu Arg Arg Gln Leu Thr Pro Tyr Ala Gln Arg Met
    130                 135                 140

Glu Arg Val Leu Arg Glu Asn Ala Asp Ser Leu Gln Ala Ser Leu Arg

```
                145                 150                 155                 160
        Pro His Ala Asp Glu Leu Lys Ala Lys Ile Asp Gln Asn Val Glu Glu
                        165                 170                 175

Leu Lys Gly Arg Leu Thr Pro Tyr Ala Asp Glu Phe Lys Val Lys Ile
                        180                 185                 190

Asp Gln Thr Val Glu Glu Leu Arg Arg Ser Leu Ala Pro Tyr Ala Gln
                        195                 200                 205

Asp Thr Gln Glu Lys Leu Asn His Gln Leu Gly Leu Thr Phe Gln
                        210                 215                 220

Met Lys Lys Asn Ala Glu Glu Leu Lys Ala Arg Ile Ser Ala Ser Ala
        225                 230                 235                 240

Glu Glu Leu Arg Gln Arg Leu Ala Pro Leu Ala Glu Asp Val Arg Gly
                        245                 250                 255

Asn Leu Arg Gly Asn Thr Glu Gly Leu Gln Lys Ser Leu Ala Glu Leu
                        260                 265                 270

Gly Gly His Leu Asp Gln Gln Val Glu Glu Phe Arg Arg Val Glu
                        275                 280                 285

Pro Tyr Gly Glu Asn Phe Asn Lys Ala Leu Val Gln Gln Met Glu Gln
                        290                 295                 300

Leu Arg Gln Lys Leu Gly Pro His Ala Gly Asp Val Glu Gly His Leu
        305                 310                 315                 320

Ser Phe Leu Glu Lys Asp Leu Arg Asp Lys Val Asn Ser Phe Phe Ser
                        325                 330                 335

Thr Phe Lys Glu Lys Glu Ser Gln Asp Lys Thr Leu Ser Leu Pro Glu
                        340                 345                 350

Leu Glu Gln Gln Gln Glu Gln Gln Gln Glu Gln Gln Gln Glu Gln Val
                        355                 360                 365

Gln Met Leu Ala Pro Leu Glu Ser
                        370                 375

<210> SEQ ID NO 2
<211> LENGTH: 361
<212> TYPE: PRT
<213> ORGANISM: Mus musculus

<400> SEQUENCE: 2

Glu Val Thr Ser Asp Gln Val Ala Asn Val Val Trp Asp Tyr Phe Thr
        1               5                   10                  15

Gln Leu Ser Asn Asn Ala Lys Glu Ala Val Glu Gln Phe Gln Lys Thr
                        20                  25                  30

Asp Val Gln Gln Leu Ser Thr Leu Phe Ala Ser Thr Tyr Ala Asp Gly
                        35                  40                  45

Val His Asn Lys Leu Val Pro Phe Val Val Gln Leu Ser Gly His Leu
                50                  55                  60

Ala Gln Glu Thr Glu Arg Val Lys Glu Ile Lys Lys Glu Leu Glu
        65                  70                  75                  80

Asp Leu Arg Asp Arg Lys Thr Gln Thr Phe Gly Glu Asn Met Gln Lys
                        85                  90                  95

Leu Gln Glu His Leu Lys Pro Tyr Ala Val Asp Leu Gln Asp Gln Ile
                        100                 105                 110

Asn Thr Gln Thr Gln Glu Met Lys Leu Gln Leu Thr Pro Tyr Ile Gln
                        115                 120                 125

Arg Met Gln Thr Thr Ile Lys Glu Asn Val Asp Asn Leu His Thr Ser
                        130                 135                 140
```

```
Met Met Pro Leu Ala Thr Asn Leu Lys Asp Lys Phe Asn Arg Asn Met
145                 150                 155                 160

Glu Glu Leu Lys Gly His Leu Thr Pro Arg Ala Asn Glu Leu Lys Ala
                165                 170                 175

Thr Ile Asp Gln Asn Leu Glu Asp Leu Arg Arg Ser Leu Ala Pro Leu
            180                 185                 190

Thr Val Gly Val Gln Glu Lys Leu Asn His Gln Met Glu Gly Leu Ala
        195                 200                 205

Phe Gln Met Lys Lys Asn Ala Glu Glu Leu Gln Thr Lys Val Ser Ala
    210                 215                 220

Lys Ile Asp Gln Leu Gln Lys Asn Leu Ala Pro Leu Val Glu Asp Val
225                 230                 235                 240

Gln Ser Lys Val Lys Gly Asn Thr Glu Gly Leu Gln Lys Ser Leu Glu
                245                 250                 255

Asp Leu Asn Arg Gln Leu Glu Gln Gln Val Glu Glu Phe Arg Arg Thr
            260                 265                 270

Val Glu Pro Met Gly Glu Met Phe Asn Lys Ala Leu Val Gln Gln Leu
        275                 280                 285

Glu Gln Phe Arg Gln Gln Leu Gly Pro Asn Ser Gly Glu Val Glu Ser
    290                 295                 300

His Leu Ser Phe Leu Glu Lys Ser Leu Arg Glu Lys Val Asn Ser Phe
305                 310                 315                 320

Met Ser Thr Leu Glu Lys Lys Gly Ser Pro Asp Gln Pro Gln Ala Leu
                325                 330                 335

Pro Leu Pro Glu Gln Ala Gln Glu Gln Ala Gln Glu Gln Ala Gln Glu
            340                 345                 350

Gln Val Gln Pro Lys Pro Leu Glu Ser
        355                 360

<210> SEQ ID NO 3
<211> LENGTH: 377
<212> TYPE: PRT
<213> ORGANISM: Artificial Sequence
<220> FEATURE:
<223> OTHER INFORMATION: Synthetic Polypeptide

<400> SEQUENCE: 3

Gly Glu Val Ser Ala Asp Gln Val Ala Thr Val Met Trp Asp Tyr Phe
1               5                   10                  15

Ser Gln Leu Ser Asn Asn Ala Lys Glu Ala Val Glu His Leu Gln Lys
                20                  25                  30

Ser Glu Leu Thr Gln Gln Leu Asn Ala Leu Phe Gln Asp Lys Leu Gly
            35                  40                  45

Glu Val Asn Thr Tyr Ala Gly Asp Leu Gln Lys Lys Leu Val Pro Phe
        50                  55                  60

Ala Thr Glu Leu His Glu Arg Leu Ala Lys Asp Ser Glu Lys Leu Lys
65                  70                  75                  80

Glu Glu Ile Gly Lys Glu Leu Glu Glu Leu Arg Ala Arg Leu Leu Pro
                85                  90                  95

His Ala Asn Glu Val Ser Gln Lys Ile Gly Asp Asn Leu Arg Glu Leu
            100                 105                 110

Gln Gln Arg Leu Glu Pro Tyr Ala Asp Gln Leu Arg Thr Gln Val Asn
        115                 120                 125

Thr Gln Ala Glu Gln Leu Arg Arg Gln Leu Thr Pro Tyr Ala Gln Arg
    130                 135                 140
```

```
Met Glu Arg Val Leu Arg Glu Asn Ala Asp Ser Leu Gln Ala Ser Leu
145                 150                 155                 160

Arg Pro His Ala Asp Glu Leu Lys Ala Lys Ile Asp Gln Asn Val Glu
            165                 170                 175

Glu Leu Lys Gly Arg Leu Thr Pro Tyr Ala Asp Glu Phe Lys Val Lys
        180                 185                 190

Ile Asp Gln Thr Val Glu Glu Leu Arg Arg Ser Leu Ala Pro Tyr Ala
    195                 200                 205

Gln Asp Thr Gln Glu Lys Leu Asn His Gln Leu Glu Gly Leu Thr Phe
    210                 215                 220

Gln Met Lys Lys Asn Ala Glu Glu Leu Lys Ala Arg Ile Ser Ala Ser
225                 230                 235                 240

Ala Glu Glu Leu Arg Gln Arg Leu Ala Pro Leu Ala Glu Asp Val Arg
            245                 250                 255

Gly Asn Leu Arg Gly Asn Thr Glu Gly Leu Gln Lys Ser Leu Ala Glu
            260                 265                 270

Leu Gly Gly His Leu Asp Gln Gln Val Glu Glu Phe Arg Arg Arg Val
        275                 280                 285

Glu Pro Tyr Gly Glu Asn Phe Asn Lys Ala Leu Val Gln Gln Met Glu
290                 295                 300

Gln Leu Arg Gln Lys Leu Gly Pro His Ala Gly Asp Val Glu Gly His
305                 310                 315                 320

Leu Ser Phe Leu Glu Lys Asp Leu Arg Asp Lys Val Asn Ser Phe Phe
            325                 330                 335

Ser Thr Phe Lys Glu Lys Glu Ser Gln Asp Lys Thr Leu Ser Leu Pro
            340                 345                 350

Glu Leu Glu Gln Gln Gln Glu Gln Gln Glu Gln Gln Gln Gln Glu Gln
        355                 360                 365

Val Gln Met Leu Ala Pro Leu Glu Ser
        370                 375

<210> SEQ ID NO 4
<211> LENGTH: 377
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is G, A, V or absent
<220> FEATURE:
<221> NAME/KEY: VARIANT
<222> LOCATION: (166)..(166)
<223> OTHER INFORMATION: X is E or K
<220> FEATURE:
<221> NAME/KEY: VARIANT
<222> LOCATION: (348)..(348)
<223> OTHER INFORMATION: X is T or S
<220> FEATURE:
<221> NAME/KEY: VARIANT
<222> LOCATION: (361)..(361)
<223> OTHER INFORMATION: X is Q or H

<400> SEQUENCE: 4

Xaa Glu Val Ser Ala Asp Gln Val Ala Thr Val Met Trp Asp Tyr Phe
1               5                   10                  15

Ser Gln Leu Ser Asn Asn Ala Lys Glu Ala Val Glu His Leu Gln Lys
            20                  25                  30

Ser Glu Leu Thr Gln Gln Leu Asn Ala Leu Phe Gln Asp Lys Leu Gly
        35                  40                  45

Glu Val Asn Thr Tyr Ala Gly Asp Leu Gln Lys Lys Leu Val Pro Phe
```

```
                    50                  55                  60
Ala Thr Glu Leu His Glu Arg Leu Ala Lys Asp Ser Glu Lys Leu Lys
 65                  70                  75                  80

Glu Glu Ile Gly Lys Glu Leu Glu Glu Leu Arg Ala Arg Leu Leu Pro
                 85                  90                  95

His Ala Asn Glu Val Ser Gln Lys Ile Gly Asp Asn Leu Arg Glu Leu
            100                 105                 110

Gln Gln Arg Leu Glu Pro Tyr Ala Asp Gln Leu Arg Thr Gln Val Asn
        115                 120                 125

Thr Gln Ala Glu Gln Leu Arg Arg Gln Leu Thr Pro Tyr Ala Gln Arg
    130                 135                 140

Met Glu Arg Val Leu Arg Glu Asn Ala Asp Ser Leu Gln Ala Ser Leu
145                 150                 155                 160

Arg Pro His Ala Asp Xaa Leu Lys Ala Lys Ile Asp Gln Asn Val Glu
                165                 170                 175

Glu Leu Lys Gly Arg Leu Thr Pro Tyr Ala Asp Glu Phe Lys Val Lys
            180                 185                 190

Ile Asp Gln Thr Val Glu Glu Leu Arg Arg Ser Leu Ala Pro Tyr Ala
        195                 200                 205

Gln Asp Thr Gln Glu Lys Leu Asn His Gln Leu Glu Gly Leu Thr Phe
    210                 215                 220

Gln Met Lys Lys Asn Ala Glu Glu Leu Lys Ala Arg Ile Ser Ala Ser
225                 230                 235                 240

Ala Glu Glu Leu Arg Gln Arg Leu Ala Pro Leu Ala Glu Asp Val Arg
                245                 250                 255

Gly Asn Leu Arg Gly Asn Thr Glu Gly Leu Gln Lys Ser Leu Ala Glu
            260                 265                 270

Leu Gly Gly His Leu Asp Gln Gln Val Glu Glu Phe Arg Arg Arg Val
        275                 280                 285

Glu Pro Tyr Gly Glu Asn Phe Asn Lys Ala Leu Val Gln Gln Met Glu
    290                 295                 300

Gln Leu Arg Gln Lys Leu Gly Pro His Ala Gly Asp Val Glu Gly His
305                 310                 315                 320

Leu Ser Phe Leu Glu Lys Asp Leu Arg Asp Lys Val Asn Ser Phe Phe
                325                 330                 335

Ser Thr Phe Lys Glu Lys Glu Ser Gln Asp Lys Xaa Leu Ser Leu Pro
            340                 345                 350

Glu Leu Glu Gln Gln Gln Glu Gln Xaa Gln Glu Gln Gln Glu Gln
        355                 360                 365

Val Gln Met Leu Ala Pro Leu Glu Ser
    370                 375

<210> SEQ ID NO 5
<211> LENGTH: 1125
<212> TYPE: DNA
<213> ORGANISM: Homo sapiens

<400> SEQUENCE: 5
gtcagtgctg accaggtggc cacagtgatg tgggactact tcagccagct gagcaacaat      60
gccaaggagg ccgtggaaca tctccagaaa tctgaactca cccagcaact caatgccctc     120
ttccaggaca aacttggaga agtgaacact tacgcaggtg acctgcagaa gaagctggtg     180
ccctttgcca ccgagctgca tgaacgcctg gccaaggact cggagaaact gaaggaggag     240
attgggaagg agctggagga gctgagggcc cggctgctgc cccatgccaa tgaggtgagc     300
```

```
cagaagatcg gggacaacct gcgagagctt cagcagcgcc tggagcccta cgcggaccag    360
ctgcgcaccc aggtcaacac gcaggccgag cagctgcggc gccagctgac ccctacgca    420 cagcgcatgg agagagtgct gcgggagaac gccgacagcc tgcaggcctc gctgaggccc    480
cacgccgacg agctcaaggc caagatcgac cagaacgtgg aggagctcaa gggacgcctt    540
acgccctacg ctgacgaatt caaagtcaag attgaccaga ccgtggagga gctgcgccgc    600
agcctggctc cctatgctca ggacacgcag gagaagctca accaccagct gagggcctg    660 accttccaga tgaagaagaa cgccgaggag ctcaaggcca ggatctcggc cagtgccgag    720
gagctgcggc agaggctggc gcccttggcc gaggacgtgc gtggcaacct gaggggcaac    780 accgagggc tgcagaagtc actggcagag ctgggtgggc acctggacca gcaggtggag    840
gagttccgac gccgggtgga gccctacggg gaaaacttca caaagccct ggtgcagcag    900 atggaacagc tcaggcagaa actgggcccc catgcggggg acgtggaagg ccacctgagc    960
ttcctggaga aggacctgag ggacaaggtc aactccttct tcagcacctt caaggagaaa    1020
gagagccagg acaagactct ctccctccct gagctcgagc aacagcagga acagcagcag    1080
gagcagcagc aggagcaggt gcagatgctg gccccttttgg agagc    1125
```

<210> SEQ ID NO 6
<211> LENGTH: 21
<212> TYPE: PRT
<213> ORGANISM: Artificial Sequence
<220> FEATURE:
<223> OTHER INFORMATION: Synthetic peptide

<400> SEQUENCE: 6

Met Lys Lys Thr Ala Ile Ala Ile Ala Val Ala Leu Ala Gly Phe Thr
1               5                   10                  15

Ala Val Ala Gln Ala
            20

<210> SEQ ID NO 7
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 7
atgaaaaaga cagctatcgc gattgcagtg gcactggctg gtttcgctac cgtagcgcag    60
gcc                                                                 63

<210> SEQ ID NO 8
<211> LENGTH: 22
<212> TYPE: PRT
<213> ORGANISM: Artificial Sequence
<220> FEATURE:
<223> OTHER INFORMATION: Synthetic peptide

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 9
<211> LENGTH: 66
<212> TYPE: DNA

```
<213> ORGANISM: Artificial Sequence
<220> FEATURE:
<223> OTHER INFORMATION: Synthetic polynucleotide

<400> SEQUENCE: 9
atgaaatacc tgctgccgac cgctgctgct ggtctgctgc tcctcgctgc ccagccggcg      60
atggcc                                                                66

<210> SEQ ID NO 10
<211> LENGTH: 28
<212> TYPE: PRT
<213> ORGANISM: Artificial Sequence
<220> FEATURE:
<223> OTHER INFORMATION: Synthetic peptide

<400> SEQUENCE: 10

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala
            20                  25

<210> SEQ ID NO 11
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 11
atgtttaagt ttaaaaagaa tttcttagtt ggattatcgg cagctttaat gagtattagc      60
ttgttttcgg caaccgcctc tgca                                             84

<210> SEQ ID NO 12
<211> LENGTH: 397
<212> TYPE: PRT
<213> ORGANISM: Artificial Sequence
<220> FEATURE:
<223> OTHER INFORMATION: Synthetic polypeptide

<400> SEQUENCE: 12

Met Lys Lys Thr Ala Ile Ala Ile Ala Val Ala Leu Ala Gly Phe Ala
1               5                   10                  15

Thr Val Ala Gln Ala Glu Val Ser Ala Asp Gln Val Ala Thr Val Met
            20                  25                  30

Trp Asp Tyr Phe Ser Gln Leu Ser Asn Asn Ala Lys Glu Ala Val Glu
        35                  40                  45

His Leu Gln Lys Ser Glu Leu Thr Gln Gln Leu Asn Ala Leu Phe Gln
    50                  55                  60

Asp Lys Leu Gly Glu Val Asn Thr Tyr Ala Gly Asp Leu Gln Lys Lys
65                  70                  75                  80

Leu Val Pro Phe Ala Thr Glu Leu His Glu Arg Leu Ala Lys Asp Ser
                85                  90                  95

Glu Lys Leu Lys Glu Glu Ile Gly Lys Glu Leu Glu Glu Leu Arg Ala
            100                 105                 110

Arg Leu Leu Pro His Ala Asn Glu Val Ser Gln Lys Ile Gly Asp Asn
        115                 120                 125

Leu Arg Glu Leu Gln Gln Arg Leu Glu Pro Tyr Ala Asp Gln Leu Arg
    130                 135                 140

Thr Gln Val Asn Thr Gln Ala Glu Gln Leu Arg Arg Gln Leu Thr Pro
145                 150                 155                 160
```

Tyr Ala Gln Arg Met Glu Arg Val Leu Arg Glu Asn Ala Asp Ser Leu
            165                 170                 175

Gln Ala Ser Leu Arg Pro His Ala Asp Glu Leu Lys Ala Lys Ile Asp
        180                 185                 190

Gln Asn Val Glu Glu Leu Lys Gly Arg Leu Thr Pro Tyr Ala Asp Glu
    195                 200                 205

Phe Lys Val Lys Ile Asp Gln Thr Val Glu Glu Leu Arg Arg Ser Leu
210                 215                 220

Ala Pro Tyr Ala Gln Asp Thr Gln Glu Lys Leu Asn His Gln Leu Glu
225                 230                 235                 240

Gly Leu Thr Phe Gln Met Lys Lys Asn Ala Glu Glu Leu Lys Ala Arg
            245                 250                 255

Ile Ser Ala Ser Ala Glu Glu Leu Arg Gln Arg Leu Ala Pro Leu Ala
            260                 265                 270

Glu Asp Val Arg Gly Asn Leu Arg Gly Asn Thr Glu Gly Leu Gln Lys
        275                 280                 285

Ser Leu Ala Glu Leu Gly Gly His Leu Asp Gln Gln Val Glu Glu Phe
    290                 295                 300

Arg Arg Arg Val Glu Pro Tyr Gly Glu Asn Phe Asn Lys Ala Leu Val
305                 310                 315                 320

Gln Gln Met Glu Gln Leu Arg Gln Lys Leu Gly Pro His Ala Gly Asp
                325                 330                 335

Val Glu Gly His Leu Ser Phe Leu Glu Lys Asp Leu Arg Asp Lys Val
            340                 345                 350

Asn Ser Phe Phe Ser Thr Phe Lys Glu Lys Glu Ser Gln Asp Lys Thr
        355                 360                 365

Leu Ser Leu Pro Glu Leu Glu Gln Gln Gln Gln Gln Gln Gln Glu Gln
    370                 375                 380

Gln Gln Glu Gln Val Gln Met Leu Ala Pro Leu Glu Ser
385                 390                 395

<210> SEQ ID NO 13
<211> LENGTH: 1217
<212> TYPE: DNA
<213> ORGANISM: Artificial Sequence
<220> FEATURE:
<223> OTHER INFORMATION: Synthetic polynucleotide

<400> SEQUENCE: 13
aggaggtaaa acatatgaaa aagacagcta tcgcgattgc agtggcactg gctggtttcg      60
ctaccgtagc gcaggccgaa gtaagcgcag atcaggtagc aacggtaatg tgggattatt     120
ttagccaatt aagcaacaac gcaaaagagg ccgtggagca cttgcagaag agcgagctga     180
cccagcaact gaacgctctg ttccaggaca agttgggtga ggttaacacg tatgcgggcg     240
atctgcagaa gaaactggtg ccgttcgcga ccgaactgca cgagcgcctg gcgaaggata     300
gcgagaaact gaaagaagag atcggcaaag agctggaaga gctgcgtgcg cgcctgctgc     360
cacatgcgaa cgaggtgagc caaaagatcg tgacaatctc gcgagctg cagcagcgcc     420 tggagccgta cgctgaccag ctgcgtaccc aagttaacac gcaagccgag caattgcgtc     480
gtcaactgac tccgtacgcg cagcgtatgg agcgtgtcct gcgtgagaat gcggacagcc     540
tgcaagcatc cctgcgtcct cacgcggatg agctgaaggc aaaaatcgac cagaatgttg     600
aagaactgaa aggtcgtctg accccgtacg cagacgagtt caaagtcaaa attgaccaaa     660
cggttgaaga gttgcgccgc agcctggcgc cgtatgccca ggatacccaa gaaaagctga     720

-continued

```
atcatcagct ggaaggcctg accttccaga tgaagaagaa tgccgaagag ttgaaagctc      780
gtatttcggc gtctgcggaa gaactgcgcc aacgtctggc cccgttggcg aagatgtgc       840 gcggtaatct gcgtggcaac accgaaggtc tgcaaaagag cctggccgag ttgggtggcc      900
atctggatca acaggttgaa gaatttcgtc gtcgtgtgga accgtacggc gagaacttca      960
ataaggcgct ggtgcagcaa atggagcagc tgcgccagaa gctgggtccg cacgctggtg     1020
acgtcgaagg tcacctgtcc tttctggaga agacttgcg tgataaagtc aatagcttct      1080
tttctacgtt taagagaaa gagagccaag acaagaccct gtccctgccg agctggaac       1140 agcaacagga gcagcagcag gagcaacagc aagaacaagt tcagatgttg caccgctgg     1200 aaagctaatg actcgag                                                    1217
```

<210> SEQ ID NO 14
<211> LENGTH: 398
<212> TYPE: PRT
<213> ORGANISM: Artificial Sequence
<220> FEATURE:
<223> OTHER INFORMATION: Synthetic polypeptide

<400> SEQUENCE: 14

```
Met Lys Tyr Leu Leu Pro Thr Ala Ala Ala Gly Leu Leu Leu Leu Ala
1               5                   10                  15

Ala Gln Pro Ala Met Ala Glu Val Ser Ala Asp Gln Val Ala Thr Val
            20                  25                  30

Met Trp Asp Tyr Phe Ser Gln Leu Ser Asn Asn Ala Lys Glu Ala Val
        35                  40                  45

Glu His Leu Gln Lys Ser Glu Leu Thr Gln Gln Leu Asn Ala Leu Phe
    50                  55                  60

Gln Asp Lys Leu Gly Glu Val Asn Thr Tyr Ala Gly Asp Leu Gln Lys
65                  70                  75                  80

Lys Leu Val Pro Phe Ala Thr Glu Leu His Glu Arg Leu Ala Lys Asp
                85                  90                  95

Ser Glu Lys Leu Lys Glu Glu Ile Gly Lys Glu Leu Glu Glu Leu Arg
            100                 105                 110

Ala Arg Leu Leu Pro His Ala Asn Glu Val Ser Gln Lys Ile Gly Asp
        115                 120                 125

Asn Leu Arg Glu Leu Gln Gln Arg Leu Glu Pro Tyr Ala Asp Gln Leu
    130                 135                 140

Arg Thr Gln Val Asn Thr Gln Ala Glu Gln Leu Arg Arg Gln Leu Thr
145                 150                 155                 160

Pro Tyr Ala Gln Arg Met Glu Arg Val Leu Arg Glu Asn Ala Asp Ser
                165                 170                 175

Leu Gln Ala Ser Leu Arg Pro His Ala Asp Glu Leu Lys Ala Lys Ile
            180                 185                 190

Asp Gln Asn Val Glu Glu Leu Lys Gly Arg Leu Thr Pro Tyr Ala Asp
        195                 200                 205

Glu Phe Lys Val Lys Ile Asp Gln Thr Val Glu Glu Leu Arg Arg Ser
    210                 215                 220

Leu Ala Pro Tyr Ala Gln Asp Thr Gln Glu Lys Leu Asn His Gln Leu
225                 230                 235                 240

Glu Gly Leu Thr Phe Gln Met Lys Lys Asn Ala Glu Glu Leu Lys Ala
                245                 250                 255

Arg Ile Ser Ala Ser Ala Glu Glu Leu Arg Gln Arg Leu Ala Pro Leu
            260                 265                 270
```

Ala Glu Asp Val Arg Gly Asn Leu Arg Gly Asn Thr Glu Gly Leu Gln
            275                 280                 285

Lys Ser Leu Ala Glu Leu Gly Gly His Leu Asp Gln Gln Val Glu Glu
        290                 295                 300

Phe Arg Arg Val Glu Pro Tyr Gly Glu Asn Phe Asn Lys Ala Leu
305                 310                 315                 320

Val Gln Gln Met Glu Gln Leu Arg Gln Lys Leu Gly Pro His Ala Gly
                325                 330                 335

Asp Val Glu Gly His Leu Ser Phe Leu Glu Lys Asp Leu Arg Asp Lys
            340                 345                 350

Val Asn Ser Phe Phe Ser Thr Phe Lys Glu Lys Glu Ser Gln Asp Lys
        355                 360                 365

Thr Leu Ser Leu Pro Glu Leu Glu Gln Gln Gln Glu Gln Gln Gln Glu
    370                 375                 380

Gln Gln Gln Glu Gln Val Gln Met Leu Ala Pro Leu Glu Ser
385                 390                 395

<210> SEQ ID NO 15
<211> LENGTH: 1221
<212> TYPE: DNA
<213> ORGANISM: Artificial Sequence
<220> FEATURE:
<223> OTHER INFORMATION: Synthetic polynucleotide

<400> SEQUENCE: 15
gaaggagata tacatatgaa atacctgctg ccgaccgctg ctgctggtct gctgctcctc        60
gctgcccagc cggcgatggc cgaagtaagc gcagatcagg tagcaacggt aatgtgggat       120
tattttagcc aattaagcaa caacgcaaaa gaggccgtgg agcacttgca aagagcgag        180 ctgacccagc aactgaacgc tctgttccag gacaagttgg gtgaggttaa cacgtatgcg       240
ggcgatctgc agaagaaact ggtgccgttc cgcaccgaac tgcacgagcg cctggcgaag       300
gatagcgaga aactgaaaga agagatcggc aaagagctgg aagagctgcg tgcgcgcctg       360
ctgccacatg cgaacgaggt gagccaaaag atcggtgaca atctgcgcga gctgcagcag       420
cgcctggagc cgtacgctga ccagctgcgt acccaagtta acacgcaagc cgagcaattg       480
cgtcgtcaac tgactccgta cgcgcagcgt atggagcgtg tcctgcgtga gaatgcggac       540
agcctgcaag catccctgcg tcctcacgcg gatgagctga aggcaaaaat cgaccagaat       600
gttgaagaac tgaaaggtcg tctgaccccg tacgcagacg agttcaaagt caaaattgac       660
caaacggttg aagagttgcg ccgcagcctg gcgccgtatg cccaggatac ccaagaaaag       720
ctgaatcatc agctggaagg cctgaccttc cagatgaaga gaatgccga agagttgaaa       780 gctcgtattt cggcgtctgc ggaagaactg cgccaacgtc tggccccgtt ggcggaagat       840
gtgcgcggta atctgcgtgg caacaccgaa ggtctgcaaa agagcctggc cgagttgggt       900
ggccatctgg atcaacaggt tgaagaattt cgtcgtcgtg tggaaccgta cggcgagaac       960
ttcaataagg cgctggtgca gcaaatggag cagctgcgcc agaagctggg tccgcacgct      1020
ggtgacgtcg aaggtcacct gtcctttctg gagaaagact tgcgtgataa agtcaatagc      1080
ttcttttcta cgtttaaaga aaagagagc caagacaaga ccctgtccct gccgagctg       1140 gaacagcaac aggagcagca gcaggagcaa cagcaagaac aagttcagat gttggcaccg      1200
ctggaaagct aatgactcga g                                                1221

<210> SEQ ID NO 16

<211> LENGTH: 404
<212> TYPE: PRT
<213> ORGANISM: Artificial Sequence
<220> FEATURE:
<223> OTHER INFORMATION: Synthetic polypeptide

<400> SEQUENCE: 16

```
Met Phe Lys Phe Lys Lys Asn Phe Leu Val Gly Leu Ser Ala Ala Leu
1               5                   10                  15
Met Ser Ile Ser Leu Phe Ser Ala Thr Ala Ser Ala Glu Val Ser Ala
            20                  25                  30
Asp Gln Val Ala Thr Val Met Trp Asp Tyr Phe Ser Gln Leu Ser Asn
        35                  40                  45
Asn Ala Lys Glu Ala Val Glu His Leu Gln Lys Ser Glu Leu Thr Gln
    50                  55                  60
Gln Leu Asn Ala Leu Phe Gln Asp Lys Leu Gly Glu Val Asn Thr Tyr
65                  70                  75                  80
Ala Gly Asp Leu Gln Lys Lys Leu Val Pro Phe Ala Thr Glu Leu His
                85                  90                  95
Glu Arg Leu Ala Lys Asp Ser Glu Lys Leu Lys Glu Ile Gly Lys
            100                 105                 110
Glu Leu Glu Glu Leu Arg Ala Arg Leu Leu Pro His Ala Asn Glu Val
        115                 120                 125
Ser Gln Lys Ile Gly Asp Asn Leu Arg Glu Leu Gln Gln Arg Leu Glu
    130                 135                 140
Pro Tyr Ala Asp Gln Leu Arg Thr Gln Val Asn Thr Gln Ala Glu Gln
145                 150                 155                 160
Leu Arg Arg Gln Leu Thr Pro Tyr Ala Gln Arg Met Glu Arg Val Leu
                165                 170                 175
Arg Glu Asn Ala Asp Ser Leu Gln Ala Ser Leu Arg Pro His Ala Asp
            180                 185                 190
Glu Leu Lys Ala Lys Ile Asp Gln Asn Val Glu Glu Leu Lys Gly Arg
        195                 200                 205
Leu Thr Pro Tyr Ala Asp Glu Phe Lys Val Lys Ile Asp Gln Thr Val
    210                 215                 220
Glu Glu Leu Arg Arg Ser Leu Ala Pro Tyr Ala Gln Asp Thr Gln Glu
225                 230                 235                 240
Lys Leu Asn His Gln Leu Glu Gly Leu Thr Phe Gln Met Lys Lys Asn
                245                 250                 255
Ala Glu Glu Leu Lys Ala Arg Ile Ser Ala Ser Ala Glu Glu Leu Arg
            260                 265                 270
Gln Arg Leu Ala Pro Leu Ala Glu Asp Val Arg Gly Asn Leu Arg Gly
        275                 280                 285
Asn Thr Glu Gly Leu Gln Lys Ser Leu Ala Glu Leu Gly Gly His Leu
    290                 295                 300
Asp Gln Gln Val Glu Glu Phe Arg Arg Val Glu Pro Tyr Gly Glu
305                 310                 315                 320
Asn Phe Asn Lys Ala Leu Val Gln Gln Met Glu Gln Leu Arg Gln Lys
                325                 330                 335
Leu Gly Pro His Ala Gly Asp Val Glu Gly His Leu Ser Phe Leu Glu
            340                 345                 350
Lys Asp Leu Arg Asp Lys Val Asn Ser Phe Phe Ser Thr Phe Lys Glu
        355                 360                 365
Lys Glu Ser Gln Asp Lys Thr Leu Ser Leu Pro Glu Leu Glu Gln Gln
    370                 375                 380
```

Gln Glu Gln Gln Gln Glu Gln Gln Glu Gln Val Gln Met Leu Ala
385                 390                 395                 400

Pro Leu Glu Ser

<210> SEQ ID NO 17
<211> LENGTH: 1239
<212> TYPE: DNA
<213> ORGANISM: Artificial Sequence
<220> FEATURE:
<223> OTHER INFORMATION: Synthetic polynucleotide

<400> SEQUENCE: 17

| | | | | | |
|---|---|---|---|---|---|
| gaaggagata | tacatatgtt | taagtttaaa | aagaatttct | tagttggatt | atcggcagct | 60 |
| ttaatgagta | ttagcttgtt | ttcggcaacc | gcctctgcag | aagtaagcgc | agatcaggta | 120 |
| gcaacggtaa | tgtgggatta | ttttagccaa | ttaagcaaca | acgcaaaaga | ggccgtggag | 180 |
| cacttgcaga | agagcgagct | gacccagcaa | ctgaacgctc | tgttccagga | caagttgggt | 240 |
| gaggttaaca | cgtatgcggg | cgatctgcag | aagaaactgg | tgccgttcgc | gaccgaactg | 300 |
| cacgagcgcc | tggcgaagga | tagcgagaaa | ctgaaagaag | agatcggcaa | agagctggaa | 360 |
| gagctgcgtg | cgcgcctgct | gccacatgcg | aacgaggtga | gccaaaagat | cggtgacaat | 420 |
| ctgcgcgagc | tgcagcagcg | cctggagccg | tacgctgacc | agctgcgtac | ccaagttaac | 480 |
| acgcaagccg | agcaattgcg | tcgtcaactg | actccgtacg | cgcagcgtat | ggagcgtgtc | 540 |
| ctgcgtgaga | atgcggacag | cctgcaagca | tccctgcgtc | ctcacgcgga | tgagctgaag | 600 |
| gcaaaaatcg | accagaatgt | tgaagaactg | aaaggtcgtc | tgaccccgta | cgcagacgag | 660 |
| ttcaaagtca | aaattgacca | aacggttgaa | gagttgcgcc | gcagcctggc | gccgtatgcc | 720 |
| caggataccc | aagaaaagct | gaatcatcag | ctggaaggcc | tgaccttcca | gatgaagaag | 780 |
| aatgccgaag | agttgaaagc | tcgtatttcg | gcgtctgcgg | aagaactgcg | ccaacgtctg | 840 |
| gccccgttgg | cggaagatgt | gcgcggtaat | ctgcgtggca | acaccgaagg | tctgcaaaag | 900 |
| agcctggccg | agttgggtgg | ccatctggat | caacaggttg | aagaatttcg | tcgtcgtgtg | 960 |
| gaaccgtacg | gcgagaactt | caataaggcg | ctggtgcagc | aaatggagca | gctgcgccag | 1020 |
| aagctgggtc | cgcacgctgg | tgacgtcgaa | ggtcacctgt | cctttctgga | aaagacttg | 1080 |
| cgtgataaag | tcaatagctt | cttttctacg | tttaaagaga | aagagagcca | agacaagacc | 1140 |
| ctgtccctgc | cggagctgga | acagcaacag | gagcagcagc | aggagcaaca | gcaagaacaa | 1200 |
| gttcagatgt | tggcaccgct | ggaaagctaa | tgactcgag | | | 1239 |

<210> SEQ ID NO 18
<211> LENGTH: 377
<212> TYPE: PRT
<213> ORGANISM: Artificial Sequence
<220> FEATURE:
<223> OTHER INFORMATION: Synthetic polypeptide

<400> SEQUENCE: 18

Met Glu Val Ser Ala Asp Gln Val Ala Thr Val Met Trp Asp Tyr Phe
1               5                   10                  15

Ser Gln Leu Ser Asn Asn Ala Lys Glu Ala Val Glu His Leu Gln Lys
                20                  25                  30

Ser Glu Leu Thr Gln Gln Leu Asn Ala Leu Phe Gln Asp Lys Leu Gly
            35                  40                  45

Glu Val Asn Thr Tyr Ala Gly Asp Leu Gln Lys Lys Leu Val Pro Phe
        50                  55                  60

Ala Thr Glu Leu His Glu Arg Leu Ala Lys Asp Ser Glu Lys Leu Lys
65                  70                  75                  80

Glu Glu Ile Gly Lys Glu Leu Glu Gln Leu Arg Ala Arg Leu Leu Pro
                85                  90                  95

His Ala Asn Glu Val Ser Gln Lys Ile Gly Asp Asn Leu Arg Glu Leu
            100                 105                 110

Gln Gln Arg Leu Glu Pro Tyr Ala Asp Gln Leu Arg Thr Gln Val Asn
        115                 120                 125

Thr Gln Ala Glu Gln Leu Arg Arg Gln Leu Thr Pro Tyr Ala Gln Arg
130                 135                 140

Met Glu Arg Val Leu Arg Glu Asn Ala Asp Ser Leu Gln Ala Ser Leu
145                 150                 155                 160

Arg Pro His Ala Asp Glu Leu Lys Ala Lys Ile Asp Gln Asn Val Glu
                165                 170                 175

Glu Leu Lys Gly Arg Leu Thr Pro Tyr Ala Asp Glu Phe Lys Val Lys
            180                 185                 190

Ile Asp Gln Thr Val Glu Glu Leu Arg Arg Ser Leu Ala Pro Tyr Ala
        195                 200                 205

Gln Asp Thr Gln Glu Lys Leu Asn His Gln Leu Glu Gly Leu Thr Phe
    210                 215                 220

Gln Met Lys Lys Asn Ala Glu Glu Leu Lys Ala Arg Ile Ser Ala Ser
225                 230                 235                 240

Ala Glu Glu Leu Arg Gln Arg Leu Ala Pro Leu Ala Glu Asp Val Arg
                245                 250                 255

Gly Asn Leu Arg Gly Asn Thr Glu Gly Leu Gln Lys Ser Leu Ala Glu
            260                 265                 270

Leu Gly Gly His Leu Asp Gln Gln Val Glu Glu Phe Arg Arg Arg Val
        275                 280                 285

Glu Pro Tyr Gly Glu Asn Phe Asn Lys Ala Leu Val Gln Gln Met Glu
290                 295                 300

Gln Leu Arg Gln Lys Leu Gly Pro His Ala Gly Asp Val Glu Gly His
305                 310                 315                 320

Leu Ser Phe Leu Glu Lys Asp Leu Arg Asp Lys Val Asn Ser Phe Phe
                325                 330                 335

Ser Thr Phe Lys Glu Lys Glu Ser Gln Asp Lys Thr Leu Ser Leu Pro
            340                 345                 350

Glu Leu Glu Gln Gln Gln Glu Gln Gln Gln Glu Gln Gln Gln Glu Gln
        355                 360                 365

Val Gln Met Leu Ala Pro Leu Glu Ser
    370                 375

<210> SEQ ID NO 19
<211> LENGTH: 1157
<212> TYPE: DNA
<213> ORGANISM: Artificial Sequence
<220> FEATURE:
<223> OTHER INFORMATION: Synthetic polynucleotide

<400> SEQUENCE: 19
aggaggtaaa acatatggaa gtaagcgcag atcaggtagc aacggtaatg tgggattatt      60
ttagccaatt aagcaacaac gcaaaagagg ccgtggagca cttgcagaag agcgagctga     120
cccagcaact gaacgctctg ttccaggaca agttgggtga ggttaacacg tatgcgggcg     180
atctgcagaa gaaactggtg ccgttcgcga ccgaactgca cgagcgcctg gcgaaggata     240

```
gcgagaaact gaaagaagag atcggcaaag agctggaaga gctgcgtgcg cgcctgctgc      300
cacatgcgaa cgaggtgagc caaaagatcg gtgacaatct gcgcgagctg cagcagcgcc      360
tggagccgta cgctgaccag ctgcgtaccc aagttaacac gcaagccgag caattgcgtc      420
gtcaactgac tccgtacgcg cagcgtatgg agcgtgtcct gcgtgagaat gcggacagcc      480
tgcaagcatc cctgcgtcct cacgcggatg agctgaaggc aaaaatcgac cagaatgttg      540
aagaactgaa aggtcgtctg accccgtacg cagacgagtt caaagtcaaa attgaccaaa      600
cggttgaaga gttgcgccgc agcctggcgc cgtatgccca ggatacccaa gaaaagctga      660
atcatcagct ggaaggcctg accttccaga tgaagaagaa tgccgaagag ttgaaagctc      720
gtatttcggc gtctgcggaa gaactgcgcc aacgtctggc cccgttggcg aagatgtgc       780 gcggtaatct gcgtggcaac accgaaggtc tgcaaaagag cctggccgag ttgggtggcc      840
atctggatca acaggttgaa gaatttcgtc gtcgtgtgga accgtacggc gagaacttca      900
ataaggcgct ggtgcagcaa atggagcagc tgcgccagaa gctgggtccg cacgctggtg      960
acgtcgaagg tcacctgtcc tttctggaga aagacttgcg tgataaagtc aatagcttct     1020
tttctacgtt taaagagaaa gagagccaag acaagaccct gtccctgccg gagctggaac     1080
agcaacagga gcagcagcag gagcaacagc aagaacaagt tcagatgttg gcaccgctgg     1140
aaagctaatg actcgag                                                   1157
```

<210> SEQ ID NO 20
<211> LENGTH: 396
<212> TYPE: PRT
<213> ORGANISM: Homo sapiens

<400> SEQUENCE: 20

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

```
Lys Val Lys Ile Asp Gln Thr Val Glu Glu Leu Arg Arg Ser Leu Ala
    210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                    245                 250                 255
Ser Ala Ser Ala Glu Glu Leu Arg Gln Arg Leu Ala Pro Leu Ala Glu
                260                 265                 270
Asp Val Arg Gly Asn Leu Lys Gly Asn Thr Glu Gly Leu Gln Lys Ser
                275                 280                 285
Leu Ala Glu Leu Gly Gly His Leu Asp Gln Gln Val Glu Glu Phe Arg
290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                    325                 330                 335
Glu Gly His Leu Ser Phe Leu Glu Lys Asp Leu Arg Asp Lys Val Asn
                340                 345                 350
Ser Phe Phe Ser Thr Phe Lys Glu Lys Glu Ser Gln Asp Lys Thr Leu
                355                 360                 365
Ser Leu Pro Glu Leu Glu Gln Gln Glu Gln Gln Gln Glu Gln Gln
370                 375                 380
Gln Glu Gln Val Gln Met Leu Ala His Leu Glu Ser
385                 390                 395

<210> SEQ ID NO 21
<211> LENGTH: 396
<212> TYPE: PRT
<213> ORGANISM: Homo sapiens

<400> SEQUENCE: 21

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
                20                  25                  30
Asp Tyr Phe Ser Gln Leu Ser Asn Asn Ala Lys Glu Ala Val Glu His
            35                  40                  45
Leu Gln Lys Ser Glu Leu Thr Gln Gln Leu Asn Ala Leu Phe Gln Asp
        50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                85                  90                  95
Lys Leu Lys Glu Glu Ile Gly Lys Glu Leu Glu Glu Leu Arg Ala Arg
                100                 105                 110
Leu Leu Pro His Ala Asn Glu Val Ser Gln Lys Ile Gly Asp Asn Leu
            115                 120                 125
Arg Glu Leu Gln Gln Arg Leu Glu Pro Tyr Ala Asp Gln Leu Arg Thr
        130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asp Gln
                180                 185                 190
```

```
Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Lys Glu Gln Val Gln Met Leu Ala Pro Leu Glu Ser
385                 390                 395

<210> SEQ ID NO 22
<211> LENGTH: 396
<212> TYPE: PRT
<213> ORGANISM: Homo sapiens

<400> SEQUENCE: 22

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
```

```
                    165                 170                 175
Ala Ser Leu Arg Pro His Ala Asp Glu Leu Lys Ala Lys Ile Asp Gln
                180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Leu Arg Arg Ser Leu Ala
        210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
                290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Gln Glu Gln Gln Lys Glu Gln Gln
            370                 375                 380

Gln Glu Gln Val Gln Met Leu Ala Pro Leu Glu Ser
385                 390                 395

<210> SEQ ID NO 23
<211> LENGTH: 396
<212> TYPE: PRT
<213> ORGANISM: Homo sapiens

<400> SEQUENCE: 23

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140
```

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 24
<211> LENGTH: 396
<212> TYPE: PRT
<213> ORGANISM: Homo sapiens

<400> SEQUENCE: 24

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
            50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
            85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

```
Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
                180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Pro Glu Gln Gln Glu Gln Gln
370                 375                 380

Gln Glu Gln Val Gln Met Leu Ala Pro Leu Glu Ser
385                 390                 395

<210> SEQ ID NO 25
<211> LENGTH: 396
<212> TYPE: PRT
<213> ORGANISM: Homo sapiens

<400> SEQUENCE: 25

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
```

```
                100             105             110
Leu Leu Pro His Ala Asn Glu Val Ser Gln Lys Ile Gly Asp Asn Leu
            115                 120                 125
Arg Glu Leu Gln Gln Arg Leu Glu Pro Tyr Ala Asp Gln Leu Arg Thr
130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asp Gln
            180                 185                 190
Asn Val Glu Glu Leu Lys Gly Arg Leu Thr Pro Tyr Ala Asp Glu Phe
        195                 200                 205
Lys Val Lys Ile Asp Gln Thr Val Glu Glu Leu Arg Arg Ser Leu Ala
    210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Val Arg Gly Asn Leu Lys Gly Asn Thr Glu Gly Leu Gln Lys Ser
        275                 280                 285
Leu Ala Glu Leu Gly Gly His Leu Asp Gln Gln Val Glu Glu Phe Arg
    290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Lys Ser Leu
        355                 360                 365
Ser Leu Pro Glu Leu Glu Gln Gln Gln Glu Gln Gln Gln Glu Gln Gln
    370                 375                 380
Gln Glu Gln Val Gln Met Leu Ala Pro Leu Glu Ser
385                 390                 395

<210> SEQ ID NO 26
<211> LENGTH: 396
<212> TYPE: PRT
<213> ORGANISM: Homo sapiens

<400> SEQUENCE: 26

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
            20                  25                  30
Asp Tyr Phe Ser Gln Leu Ser Asn Asn Ala Lys Glu Ala Val Glu His
        35                  40                  45
Leu Gln Lys Ser Glu Leu Thr Gln Gln Leu Asn Ala Leu Phe Gln Asp
    50                  55                  60
Lys Leu Gly Glu Val Asn Thr Tyr Ala Gly Asp Leu Gln Lys Lys Leu
65                  70                  75                  80
```

-continued

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ala Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Glu Gln Gln
    370                 375                 380

Gln Glu Gln Val Gln Met Leu Ala Pro Leu Glu Ser
385                 390                 395

<210> SEQ ID NO 27
<211> LENGTH: 396
<212> TYPE: PRT
<213> ORGANISM: Homo sapiens

<400> SEQUENCE: 27

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Tyr
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Glu Gln Gln Gln Glu Gln Gln Gln
370                 375                 380

Gln Glu Gln Val Gln Met Leu Ala Pro Leu Glu Ser
385                 390                 395

<210> SEQ ID NO 28
<211> LENGTH: 396
<212> TYPE: PRT
<213> ORGANISM: Homo sapiens

<400> SEQUENCE: 28

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His

```
            35                  40                  45
Leu Gln Lys Ser Glu Leu Thr Gln Gln Leu Asn Ala Leu Phe Gln Asp
 50                  55                  60

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Met
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Glu Gln Gln Glu Gln Gln
370                 375                 380

Gln Glu Gln Val Gln Met Leu Ala Pro Leu Glu Ser
385                 390                 395

<210> SEQ ID NO 29
<211> LENGTH: 396
<212> TYPE: PRT
<213> ORGANISM: Homo sapiens

<400> SEQUENCE: 29

Met Phe Leu Lys Ala Val Val Leu Thr Leu Ala Leu Val Ala Val Ala
 1               5                  10                  15
```

```
Gly Ala Arg Ala Glu Val Ser Ala Asp Gln Val Ala Thr Val Met Trp
             20                  25                  30

Asp Tyr Phe Ser Gln Leu Ser Asn Asn Ala Lys Glu Ala Val Glu His
         35                  40                  45

Leu Gln Lys Ser Glu Leu Thr Gln Gln Leu Asn Ala Leu Phe Gln Asp
 50                  55                  60

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly His Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395
```

<210> SEQ ID NO 30
<211> LENGTH: 396
<212> TYPE: PRT
<213> ORGANISM: Homo sapiens

<400> SEQUENCE: 30

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Arg Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 31
<211> LENGTH: 396
```

<212> TYPE: PRT
<213> ORGANISM: Homo sapiens

<400> SEQUENCE: 31

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Leu Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

```
<210> SEQ ID NO 32
<211> LENGTH: 396
<212> TYPE: PRT
<213> ORGANISM: Homo sapiens

<400> SEQUENCE: 32

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Cys Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
```

```
              370                 375                 380
Gln Glu Gln Val Gln Met Leu Ala Pro Leu Glu Ser
385                 390                 395

<210> SEQ ID NO 33
<211> LENGTH: 396
<212> TYPE: PRT
<213> ORGANISM: Homo sapiens

<400> SEQUENCE: 33

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Gln
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350
```

```
Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Glu Gln Gln
370                 375                 380

Gln Glu Gln Val Gln Met Leu Ala Pro Leu Glu Ser
385                 390                 395

<210> SEQ ID NO 34
<211> LENGTH: 396
<212> TYPE: PRT
<213> ORGANISM: Homo sapiens

<400> SEQUENCE: 34

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Gly Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335
```

-continued

```
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Lys Thr Leu
        355                 360                 365
Ser Leu Pro Glu Leu Glu Gln Gln Gln Glu Gln Gln Gln Glu Gln Gln
    370                 375                 380
Gln Glu Gln Val Gln Met Leu Ala Pro Leu Glu Ser
385                 390                 395

<210> SEQ ID NO 35
<211> LENGTH: 396
<212> TYPE: PRT
<213> ORGANISM: Homo sapiens

<400> SEQUENCE: 35

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
            20                  25                  30
Asp Tyr Phe Ser Gln Leu Ser Asn Asn Ala Lys Glu Ala Val Glu His
        35                  40                  45
Leu Gln Lys Ser Glu Leu Thr Gln Gln Leu Asn Ala Leu Phe Gln Asp
    50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                85                  90                  95
Lys Leu Lys Glu Glu Ile Gly Lys Glu Leu Glu Glu Leu Arg Ala Arg
            100                 105                 110
Leu Leu Pro His Ala Asn Glu Val Ser Gln Lys Ile Gly Asp Asn Leu
        115                 120                 125
Arg Glu Leu Gln Gln Arg Leu Glu Pro Tyr Ala Asp Gln Leu Arg Thr
    130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asp Gln
            180                 185                 190
Asn Val Glu Glu Leu Lys Gly Arg Leu Thr Pro Tyr Ala Asp Glu Phe
        195                 200                 205
Lys Val Lys Ile Asp Gln Thr Val Glu Glu Leu Arg Arg Ser Leu Ala
    210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Met Arg Gly Asn Leu Lys Gly Asn Thr Glu Gly Leu Gln Lys Ser
        275                 280                 285
Leu Ala Glu Leu Gly Gly His Leu Asp Gln Gln Val Glu Glu Phe Arg
    290                 295                 300
Arg Arg Val Glu Pro Tyr Gly Glu Asn Phe Asn Lys Ala Leu Val Gln
```

```
                    305                 310                 315                 320
    Gln Met Glu Gln Leu Arg Gln Lys Leu Gly Pro His Ala Gly Asp Val
                    325                 330                 335

Glu Gly His Leu Ser Phe Leu Glu Lys Asp Leu Arg Asp Lys Val Asn
                    340                 345                 350

Ser Phe Phe Ser Thr Phe Lys Glu Lys Glu Ser Gln Asp Lys Thr Leu
                    355                 360                 365

Ser Leu Pro Glu Leu Glu Gln Gln Gln Glu Gln Gln Gln Glu Gln Gln
                    370                 375                 380

Gln Glu Gln Val Gln Met Leu Ala Pro Leu Glu Ser
    385                 390                 395

<210> SEQ ID NO 36
<211> LENGTH: 396
<212> TYPE: PRT
<213> ORGANISM: Homo sapiens

<400> SEQUENCE: 36

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Ala Arg Gly Asn Leu Lys Gly Asn Thr Glu Gly Leu Gln Lys Ser
        275                 280                 285
```

```
Leu Ala Glu Leu Gly Gly His Leu Asp Gln Gln Val Glu Phe Arg
290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
            325                 330                 335
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Lys Thr Leu
            355                 360                 365
Ser Leu Pro Glu Leu Glu Gln Gln Gln Glu Gln Gln Gln Gln Gln Gln
370                 375                 380
Gln Glu Gln Val Gln Met Leu Ala Pro Leu Glu Ser
385                 390                 395

<210> SEQ ID NO 37
<211> LENGTH: 396
<212> TYPE: PRT
<213> ORGANISM: Homo sapiens

<400> SEQUENCE: 37

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
            20                  25                  30
Asp Tyr Phe Ser Gln Leu Ser Asn Asn Ala Lys Glu Ala Val Glu His
            35                  40                  45
Leu Gln Lys Ser Glu Leu Thr Gln Gln Leu Asn Ala Leu Phe Gln Asp
50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                85                  90                  95
Lys Leu Lys Glu Glu Ile Gly Lys Glu Leu Glu Glu Leu Arg Ala Arg
            100                 105                 110
Leu Leu Pro His Ala Asn Glu Val Ser Gln Lys Ile Gly Asp Asn Leu
            115                 120                 125
Arg Glu Leu Gln Gln Arg Leu Glu Pro Tyr Ala Asp Gln Leu Arg Thr
130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asp Gln
            180                 185                 190
Asn Val Glu Glu Leu Lys Gly Arg Leu Thr Pro Tyr Ala Asp Glu Phe
            195                 200                 205
Lys Val Lys Ile Asp Gln Thr Val Glu Glu Leu Arg Arg Ser Leu Ala
210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Gln Gln Arg Leu Ala Pro Leu Ala Glu
            260                 265                 270
```

```
Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
        290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Gln Gln Gln
    370                 375                 380

Gln Glu Gln Val Gln Met Leu Ala Pro Leu Glu Ser
385                 390                 395

<210> SEQ ID NO 38
<211> LENGTH: 396
<212> TYPE: PRT
<213> ORGANISM: Homo sapiens

<400> SEQUENCE: 38

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
```

```
                    245                 250                 255
Ser Ala Ser Thr Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Gln Gln Gln
            370                 375                 380

Gln Glu Gln Val Gln Met Leu Ala Pro Leu Glu Ser
385                 390                 395

<210> SEQ ID NO 39
<211> LENGTH: 396
<212> TYPE: PRT
<213> ORGANISM: Homo sapiens

<400> SEQUENCE: 39

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
            210                 215                 220
```

-continued

```
Pro Tyr Ala Gln Asp Thr Gln Glu Lys Leu Asn His Gln Leu Glu Gly
225                 230                 235                 240

Leu Thr Phe Gln Met Lys Lys Asn Ala Lys Glu Leu Lys Ala Arg Ile
            245                 250                 255

Ser Ala Ser Ala Glu Glu Leu Arg Gln Arg Leu Ala Pro Leu Ala Glu
        260                 265                 270

Asp Val Arg Gly Asn Leu Lys Gly Asn Thr Glu Gly Leu Gln Lys Ser
    275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
        340                 345                 350

Ser Phe Phe Ser Thr Phe Lys Glu Lys Glu Ser Gln Asp Lys Thr Leu
    355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 40
<211> LENGTH: 396
<212> TYPE: PRT
<213> ORGANISM: Homo sapiens

<400> SEQUENCE: 40

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205
```

```
Lys Val Lys Ile Asp Gln Thr Val Glu Glu Leu Arg Arg Ser Leu Ala
        210                 215                 220

Pro Tyr Ala Gln Asp Thr Gln Glu Lys Leu Ser His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 41
<211> LENGTH: 396
<212> TYPE: PRT
<213> ORGANISM: Homo sapiens

<400> SEQUENCE: 41

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
```

```
            180                 185                 190
Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
            210                 215                 220

Pro Tyr Ala Gln Asp Thr Lys Glu Lys Leu Asn His Gln Leu Glu Gly
225                 230                 235                 240

Leu Thr Phe Gln Met Lys Lys Asn Ala Glu Glu Leu Lys Ala Arg Ile
                    245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                    325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Gln Gln Gln
370                 375                 380

Gln Glu Gln Val Gln Met Leu Ala Pro Leu Glu Ser
385                 390                 395

<210> SEQ ID NO 42
<211> LENGTH: 396
<212> TYPE: PRT
<213> ORGANISM: Homo sapiens

<400> SEQUENCE: 42

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160
```

Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln
        180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Cys Arg Ser Leu Ala
        210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
        290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
        370                 375                 380

Gln Glu Gln Val Gln Met Leu Ala Pro Leu Glu Ser
385                 390                 395

<210> SEQ ID NO 43
<211> LENGTH: 396
<212> TYPE: PRT
<213> ORGANISM: Homo sapiens

<400> SEQUENCE: 43

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
            85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

```
Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp His Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 44
<211> LENGTH: 396
<212> TYPE: PRT
<213> ORGANISM: Homo sapiens

<400> SEQUENCE: 44

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
```

```
                115                 120                 125
Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Lys Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 45
<211> LENGTH: 396
<212> TYPE: PRT
<213> ORGANISM: Homo sapiens

<400> SEQUENCE: 45

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95
```

```
Lys Leu Lys Glu Glu Ile Gly Lys Glu Leu Glu Leu Arg Ala Arg
                100                 105                 110
Leu Leu Pro His Ala Asn Glu Val Ser Gln Lys Ile Gly Asp Asn Leu
            115                 120                 125
Arg Glu Leu Gln Gln Arg Leu Glu Pro Tyr Ala Asp Gln Leu Arg Thr
        130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asp Gln
            180                 185                 190
Asn Val Glu Glu Leu Lys Gly Arg Leu Met Pro Tyr Ala Asp Glu Phe
        195                 200                 205
Lys Val Lys Ile Asp Gln Thr Val Glu Glu Leu Arg Arg Ser Leu Ala
210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Val Arg Gly Asn Leu Lys Gly Asn Thr Glu Gly Leu Gln Lys Ser
        275                 280                 285
Leu Ala Glu Leu Gly Gly His Leu Asp Gln Gln Val Glu Glu Phe Arg
    290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Lys Thr Leu
        355                 360                 365
Ser Leu Pro Glu Leu Glu Gln Gln Gln Glu Gln Gln Gln Glu Gln Gln
    370                 375                 380
Gln Glu Gln Val Gln Met Leu Ala Pro Leu Glu Ser
385                 390                 395

<210> SEQ ID NO 46
<211> LENGTH: 396
<212> TYPE: PRT
<213> ORGANISM: Homo sapiens

<400> SEQUENCE: 46

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
                20                  25                  30
Asp Tyr Phe Ser Gln Leu Ser Asn Asn Ala Lys Glu Ala Val Glu His
            35                  40                  45
Leu Gln Lys Ser Glu Leu Thr Gln Gln Leu Asn Ala Leu Phe Gln Asp
        50                  55                  60
Lys Leu Gly Glu Val Asn Thr Tyr Ala Gly Asp Leu Gln Lys Lys Leu
65                  70                  75                  80
```

```
Val Pro Phe Ala Thr Glu Leu His Glu Arg Leu Ala Lys Asp Ser Glu
            85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln
            180                 185                 190

Asn Val Glu Glu Leu Lys Gly Cys Leu Thr Pro Tyr Ala Asp Glu Phe
            195                 200                 205

Lys Val Lys Ile Asp Gln Thr Val Glu Glu Leu Arg Arg Ser Leu Ala
            210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395

<210> SEQ ID NO 47
<211> LENGTH: 396
<212> TYPE: PRT
<213> ORGANISM: Homo sapiens

<400> SEQUENCE: 47

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
```

```
            50                  55                  60
Lys Leu Gly Glu Val Asn Thr Tyr Ala Gly Asp Leu Gln Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
                115                 120                 125

Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asn Gln
                180                 185                 190

Asn Val Glu Glu Leu Lys Gly Arg Leu Thr Pro Tyr Ala Asp Glu Phe
                195                 200                 205

Lys Val Lys Ile Asp Gln Thr Val Glu Glu Leu Arg Arg Ser Leu Ala
                210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395

<210> SEQ ID NO 48
<211> LENGTH: 396
<212> TYPE: PRT
<213> ORGANISM: Homo sapiens

<400> SEQUENCE: 48

Met Phe Leu Lys Ala Val Val Leu Thr Leu Ala Leu Val Ala Val Ala
 1               5                  10                  15

Gly Ala Arg Ala Glu Val Ser Ala Asp Gln Val Ala Thr Val Met Trp
                20                  25                  30
```

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
 50                  55                  60

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Leu Arg Ala Arg
                100                 105                 110

Leu Leu Pro His Ala Asn Glu Val Ser Gln Lys Ile Gly Asp Asn Leu
                115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asn Glu Leu Lys Ala Lys Ile Asp Gln
                180                 185                 190

Asn Val Glu Glu Leu Lys Gly Arg Leu Thr Pro Tyr Ala Asp Glu Phe
                195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Gln Glu Gln Gln Glu Gln Gln
370                 375                 380

Gln Glu Gln Val Gln Met Leu Ala Pro Leu Glu Ser
385                 390                 395

<210> SEQ ID NO 49
<211> LENGTH: 396
<212> TYPE: PRT
<213> ORGANISM: Homo sapiens

<400> SEQUENCE: 49

Met Phe Leu Lys Ala Val Val Leu Thr Leu Ala Leu Val Ala Val Ala
 1               5                  10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
 50                  55                  60

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Leu His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 50
<211> LENGTH: 396
<212> TYPE: PRT
<213> ORGANISM: Homo sapiens

<400> SEQUENCE: 50

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Thr Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395
```

<210> SEQ ID NO 51

-continued

```
<211> LENGTH: 396
<212> TYPE: PRT
<213> ORGANISM: Homo sapiens

<400> SEQUENCE: 51

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Trp Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
```

-continued

```
            385                 390                 395

<210> SEQ ID NO 52
<211> LENGTH: 396
<212> TYPE: PRT
<213> ORGANISM: Homo sapiens

<400> SEQUENCE: 52

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
                150                 155                 160
145

Ser Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365
```

Ser Leu Pro Glu Leu Glu Gln Gln Glu Gln Gln Glu Gln Gln
    370             375             380

Gln Glu Gln Val Gln Met Leu Ala Pro Leu Glu Ser
385             390             395

<210> SEQ ID NO 53
<211> LENGTH: 396
<212> TYPE: PRT
<213> ORGANISM: Homo sapiens

<400> SEQUENCE: 53

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Trp Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

```
Ser Phe Phe Ser Thr Phe Lys Glu Lys Glu Ser Gln Asp Lys Thr Leu
            355                 360                 365

Ser Leu Pro Glu Leu Glu Gln Gln Glu Gln Gln Glu Gln Gln
370                 375                 380

Gln Glu Gln Val Gln Met Leu Ala Pro Leu Glu Ser
385                 390                 395

<210> SEQ ID NO 54
<211> LENGTH: 396
<212> TYPE: PRT
<213> ORGANISM: Homo sapiens

<400> SEQUENCE: 54

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
            85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Met Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
```

```
                    325                 330                 335
Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 55
<211> LENGTH: 396
<212> TYPE: PRT
<213> ORGANISM: Homo sapiens

<400> SEQUENCE: 55

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Ser Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300
```

```
Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Glu Gln Gln Gln Glu Gln Gln Gln
            370                 375                 380

Gln Glu Gln Val Gln Met Leu Ala Pro Leu Glu Ser
385                 390                 395
```

<210> SEQ ID NO 56
<211> LENGTH: 396
<212> TYPE: PRT
<213> ORGANISM: Homo sapiens

<400> SEQUENCE: 56

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Glu Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285
```

```
Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Gly Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395
```

<210> SEQ ID NO 57
<211> LENGTH: 396
<212> TYPE: PRT
<213> ORGANISM: Homo sapiens

<400> SEQUENCE: 57

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Lys Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
```

```
                260                 265                 270
Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
        290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
        370                 375                 380

Gln Glu Gln Val Gln Met Leu Ala Pro Leu Glu Ser
385                 390                 395

<210> SEQ ID NO 58
<211> LENGTH: 396
<212> TYPE: PRT
<213> ORGANISM: Homo sapiens

<400> SEQUENCE: 58

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Leu Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240
```

```
Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Gln Gln Gln Gln Glu Gln Gln
    370                 375                 380

Gln Glu Gln Val Gln Met Leu Ala Pro Leu Glu Ser
385                 390                 395

<210> SEQ ID NO 59
<211> LENGTH: 396
<212> TYPE: PRT
<213> ORGANISM: Homo sapiens

<400> SEQUENCE: 59

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Cys Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220
```

```
Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395

<210> SEQ ID NO 60
<211> LENGTH: 396
<212> TYPE: PRT
<213> ORGANISM: Homo sapiens

<400> SEQUENCE: 60

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Ala Glu Leu His Glu Arg Leu Ala Lys Asp Ser Glu
            85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
```

```
            195                 200                 205
Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Leu Lys Ala Arg Ile
                    245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
        290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                    325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
        370                 375                 380

Gln Glu Gln Val Gln Met Leu Ala Pro Leu Glu Ser
385                 390                 395

<210> SEQ ID NO 61
<211> LENGTH: 396
<212> TYPE: PRT
<213> ORGANISM: Homo sapiens

<400> SEQUENCE: 61

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu His Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175
```

```
Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 62
<211> LENGTH: 396
<212> TYPE: PRT
<213> ORGANISM: Homo sapiens

<400> SEQUENCE: 62

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Ser Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160
```

```
Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 63
<211> LENGTH: 396
<212> TYPE: PRT
<213> ORGANISM: Homo sapiens

<400> SEQUENCE: 63

Met Phe Leu Lys Ala Val Val Leu Thr Leu Ala Leu Met Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
```

```
                130                 135                 140
Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 64
<211> LENGTH: 396
<212> TYPE: PRT
<213> ORGANISM: Homo sapiens

<400> SEQUENCE: 64

Met Phe Leu Lys Ala Met Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110
```

```
Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395

<210> SEQ ID NO 65
<211> LENGTH: 396
<212> TYPE: PRT
<213> ORGANISM: Homo sapiens

<400> SEQUENCE: 65

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95
```

```
Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
            210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395
```

What is claimed is:

1. A method of lowering blood glucose level in a subject in need thereof, the method comprising administering to the subject an effective amount of a non-glycosylated apolipoprotein A-IV protein (apoA-IV protein) produced using a bacterial expression system such that the blood glucose level of the subject is lowered, wherein the amino acid sequence of the apoA-IV protein is (SEQ ID NO: 3)
GEVSADQVATVMWDYFSQLSNNAKEAVEHLQKSELTQQLNALFQDKLGEV

NTYAGDLQKKLVPFATELHERLAKDSEKLKEEIGKELEELRARLLLPHANE

VSQKIGDNLRELQQRLEPYADQLRTQVNTQAEQLRRQLTPYAQRMERVLR

ENADSLQASLRPHADELKAKIDQNVEELKGRLTPYADEFKVKIDQTVEEL

RRSLAPYAQDTQEKLNHQLEGLTFQMKKNAEELKARISASAEELRQRLAP

LAEDVRGNLRGNTEGLQKSLAELGGHLDQQVEEFRRRVEPYGENFNKALV

QQMEQLRQKLGPHAGDVEGHLSFLEKDLRDKVNSFFSTFKEKESQDKTLS

LPELEQQQEQQQEQQQEQVQMLAPLES.

2. The method of claim 1, wherein the bacterial expression system is *Escherichia coli*.

3. The method according to claim 1, wherein the apolipoprotein A-IV protein is administered systemically.

4. The method according to claim 3, wherein the systemic administration is selected from the group consisting of oral, subcutaneous, intravenous, intramuscular, and intraperitoneal administration.

5. The method according to claim 3, wherein the apolipoprotein A-IV protein is administered in a dose of about 1 to about 10 µg/g.

6. The method according to claim 3, wherein the apolipoprotein A-IV protein is administered in a dose of about 0.25 to about 2 µg/g.

7. The method according to claim 3, wherein the apolipoprotein A-IV protein is administered in a dose of about 1 µg/g.

8. The method according to claim 3, wherein the apolipoprotein A-IV protein is administered once daily.

9. The method according to claim 3, wherein the apolipoprotein A-IV protein is administered 2 times per day.

\* \* \* \* \*